(12) United States Patent
Fife et al.

(10) Patent No.: US 11,560,432 B2
(45) Date of Patent: Jan. 24, 2023

(54) MONOCLONAL ANTIBODIES DIRECTED TO PEPTIDE IN THE CONTEXT OF MHC AND METHODS OF MAKING AND USING MONOCLONAL ANTIBODIES

(71) Applicant: REGENTS OF THE UNIVERSITY OF MINNESOTA, Minneapolis, MN (US)

(72) Inventors: Brian T. Fife, Minneapolis, MN (US); Justin A. Spanier, Minneapolis, MN (US); Marc K. Jenkins, Minneapolis, MN (US); Justin J. Taylor, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 691 days.

(21) Appl. No.: 15/952,965

(22) Filed: Apr. 13, 2018

(65) Prior Publication Data
US 2018/0298103 A1   Oct. 18, 2018

Related U.S. Application Data

(60) Provisional application No. 62/485,762, filed on Apr. 14, 2017.

(51) Int. Cl.
| C12N 5/16 | (2006.01) |
| C07K 16/28 | (2006.01) |
| C07K 16/14 | (2006.01) |
| C07K 16/26 | (2006.01) |

(52) U.S. Cl.
CPC .......... *C07K 16/2833* (2013.01); *C07K 16/14* (2013.01); *C07K 16/26* (2013.01); *C07K 2317/10* (2013.01); *C07K 2317/32* (2013.01); *C07K 2317/34* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| 7,718,777 | B2 | 5/2010 | Hoogenboom |
| 2006/0034850 | A1 | 2/2006 | Weidanz |
| 2011/0293623 | A1* | 12/2011 | Weidanz ................ C07K 16/18 424/139.1 |
| 2012/0294874 | A1 | 11/2012 | Macary |

OTHER PUBLICATIONS

Alanio et al (Blood, 2010, 115(18): 3718-3725) (Year: 2010).*
Scriba et al (J. Immuno. 2005, 175: 6334-6343) (Year: 2005).*
Hansen et al (Trends in Immunol. 2010, 31(10): 363-369) (Year: 2010).*
Mitaksov et al (Chem. Biol. 2007 14(8): 909-922) (Year: 2007).*
HLA Nomenclature (2015) (Year: 2015).*
Tam et al (PNAS 1606050113, published online Oct. 4, 2016, pp. E6639-E6648) (Year: 2016).*
Ali-Khan et al (Current Protocols in Protein Science, 2002: 22.1.-22.1.19) (Year: 2002).*
Schumacher and Schrieber (Science, 2015, 384 (6230): 69-74) (Year: 2015).*
Wieczorek et al (Front. Immunol. 2017, vol. 8, article 292: 1-16) (Year: 2017).*
Baldwin, "T cell receptor-specific blockade of positive selection" 1999 *J Exp Med*, 189:13-23.
BioLegend, "Mouse Alloantigens" [retrieved on Apr. 14, 2017], Retrieved from the Internet: biolegend.com/media_assets/support_resource/BioLegend_Mouse_Alloantigens.pdf; 3 pgs.
Chothia, "Canonical Structures for the Hypervariable Regions of Immunoglobulins" 1987 *J. Mol. Biol.*, 196: 901-917.
Dadaglio, "Characterization and quantitation of peptide-MHC complexes produced from hen egg lysozyme using a monoclonal antibody" 1997 *Immunity*, 6:727-738.
Day, "Ex vivo analysis of human memory CD4 T cells specific for hepatitis C virus using MHC class II tetramers" 2003 *J. Clin. Invest.*, 112, 831-842.
Ertelt, "Selective priming and expansion of antigen-specific Foxp3-CD4+ T cells during Listeria monocytogenes infection" 2009 *J. Immunol.*, 182:3032-3038.
Fife, "Insulin-induced remission in new-onset NOD mice is maintained by the PD-1-PD-L1 pathway" 2006 *J Exp Med.*, 203:2737-2747.
Fife, "Control of peripheral T-cell tolerance and autoimmunity via the CTLA-4 and PD-1 pathways" 2008 *Immunol Rev.*, 224:166-182.
Fife, Interactions between PD-1 and PD-L1 promote tolerance by blocking the TCR-induced stop signal. 2009 *Nat. Immunol.*, 10(11):1185-1192.
Fife, First Name "Mechanisms of Immune Tolerance in Autoimmune Diabetes," Grant Abstracts, Project No. 5R01AI106791 [online]. National Institute of Allergy and Infectious Diseases, project dates Dec. 15, 2013 to Nov. 30, 2019 [retrieved on May 30, 2019], Retrieved from the Internet: https://projectreporter.nih.gov/; 10 pgs.
Goldsby, "Chapter 7" *Kuby Immunology, 4th Ed.* New York, NY: W.H. Freeman; 2000. Cover page, publisher page, Chapter 7; 29 pgs.
Haskins, "T-lymphocyte clone specific for pancreatic islet antigen" 1988 *Diabetes*, 37:1444-1448.
Janeway, "Monoclonal antibodies specific for Ia glycoproteins raised by immunization with activated T cells: possible role of T cellbound Ia antigens as targets of immunoregulatory T cells" 1984 *J. Immunol.*, 132:662-667.
Jones, "Replacing the complementarity-determining regions in a human antibody with those from a mouse" 1986 *Nature*, 321(6069):522-525.

(Continued)

*Primary Examiner* — G. R. Ewoldt
*Assistant Examiner* — Marianne DiBrino
(74) *Attorney, Agent, or Firm* — Marshall, Gerstein & Borun LLP

(57) ABSTRACT

Phycoerythrin (PE) and peptide:MHCII (p:MHCII) reactive monoclonal antibodies; methods to generate monoclonal antibodies including, for example, peptide:MHC (p:MHC) reactive monoclonal antibodies; compositions including monoclonal antibodies; and uses thereof.

20 Claims, 29 Drawing Sheets

Specification includes a Sequence Listing.

(56) References Cited

OTHER PUBLICATIONS

Judkowski, "Identification of MHC class II-restricted peptide ligands, including a glutamic acid decarboxylase 65 sequence, that stimulate diabetogenic T cells from transgenic BDC2.5 nonobese diabetic mice" 2001 *J. Immunol.*, 166:908-917.
Kabat, Sequences of Proteins of Immunological Interest, Fifth Edition, U.S. Department of Health and Human Services, NIH Publication No. 91-3242. 1991. Cover page, table of contents.
Katz, Following a diabetogenic T cell from genesis through pathogenesis. 1993 *Cell*, 74:1089-1100.
Kohler, "Continuous cultures of fused cells secreting antibody of predefined specificity" 1975 *Nature*, 256:495-497.
Lee, "Temporal expression of bacterial proteins instructs host CD4 T cell expansion and Th17 development" 2012 *PLoS Pathogens*, 8:e1002499; 14 pgs.
Lorber, "I-A antigens on cloned alloreactive murine T lymphocytes are acquired passively" 1982 *J. Immunol.*, 128:2798-2803.
Marrack, "Do MHCII-presented neoantigens drive type 1 diabetes and other autoimmune diseases?" 2012 *Cold Spring Harb. Perspect. Med.*, 2(9):a007765; 17 pgs.
Moon, "Naive CD4(+) T cell frequency varies for different epitopes and predicts repertoire diversity and response magnitude" 2007 *Immunity*, 27:203-213.
Moon, "Tracking epitope-specific T cells" 2009 *Nat. Protoc.*, 4:565-581.
Muraille, "Direct visualization of peptide/MHC complexes at the surface and in the intracellular compartments of cells infected in vivo by *Leishmania major*" 2010 *PLoS pathogens*, 6:e1001154; 16 pgs.
Murphy, "A novel MHC class II epitope expressed in thymic medulla but not cortex" 1989 *Nature*, 338:765-768.
Murphy, "Monoclonal antibody detection of a major self peptide MHC class II complex" 1992 *J. Immunol.*, 148:3483-3491.
National Center for Biotechnology Information, National Library of Medicine, National Institutes of Health, GenBank Accession No. / Locus No. KU955585, "Mus musculus isolate FS1 immunoglobulin gamma heavy chain mRNA, partial cds," [online]. Bethesda, MD [retrieved on Apr. 16, 2019], Retrieved from the Internet: ncbi.nlm.nih.gov/nuccore/KU955585; 1 pg.
National Center for Biotechnology Information, National Library of Medicine, National Institutes of Health, GenBank Accession No. / Locus No. KU955586, "Mus musculus isolate FS1 immunoglobulin gamma kappa light chain mRNA, partial cds," [online]. Bethesda, MD [retrieved on Apr. 16, 2019], Retrieved from the Internet: ncbi.nlm.nih.gov/nuccore/KU955586; 1 pg.
National Center for Biotechnology Information, National Library of Medicine, National Institutes of Health, GenBank Accession No. / Locus No. KU955587, "Mus musculus isolate W6 immunoglobulin gamma heavy chain mRNA, partial cds," [online]. Bethesda, MD [retrieved on Apr. 16, 2019], Retrieved from the Internet: ncbi.nlm.nih.gov/nuccore/KU955587; 1 pg.
National Center for Biotechnology Information, National Library of Medicine, National Institutes of Health, GenBank Accession No. / Locus No. KU955588, Mus musculus isolate W6 immunoglobulin gamma kappa light chain mRNA, partial cds, [online]. Bethesda, MD [retrieved on Apr. 16, 2019], Retrieved from the Internet: ncbi.nlm.nih.gov/nuccore/KU955588; 1 pg.
Nelson, "CD4+ T cell persistence and function after infection are maintained by low-level peptide:MHC class II presentation" 2013 *J. Immunol.*, 190:2828-2834.
Nelson, "T cell receptor cross-reactivity between similar foreign and self peptides influences naive cell population size and autoimmunity" 2015 *Immunity*, 42:95-107.
Newman, "Identification of an antigen-specific B cell population" 2003 *J. Immunol. Methods*, 272:177-187.
Norton, "The novel adjuvant dmLT promotes dose sparing, mucosal immunity and longevity of antibody responses to the inactivated polio vaccine in a murine model" 2015 *Vaccine*, 33:1909-1915.
Oi, "Properties of monoclonal antibodies to mouse Ig allotypes, H-2, and Ia antigens" 1978 *Curr. Top. Microbiol. Immunol.*, 81:115-129.
Pape, "Different B cell populations mediate early and late memory during an endogenous immune response" 2011 *Science*, 331:1203-1207.
Pauken, "PD-1, but not PD-L1, expressed by islet-reactive CD4+ T cells suppresses infiltration of the pancreas during type 1 diabetes" 2013 *Diabetes*, 62:2859-2869.
Pauken, "Cutting edge: type 1 diabetes occurs despite robust anergy among endogenous insulin-specific CD4 T cells in NOD mice" 2013 *J. Immunol.*, 191:4913-4917.
Pauken, "Identification of autoreactive CD4+ and CD8+ T cell subsets resistant to PD-1 pathway blockade" 2015 *J. Immunol.*, 194:3551-3555.
Rees, "An inverse relationship between T cell receptor affinity and antigen dose during $CD4^+$ T cell responses in vivo and in vitro" 1999 *Proc. Natl. Acad. Sci. USA*, 96:9781-9786.
Rudensky, "On the complexity of self" 1991 *Nature*, 353:660-662.
Singer, "Optimal humanization of 1B4, an anti-CD18 murine monoclonal antibody, is achieved by correct choice of human V-region framework sequences" 1993 *J. Immunol.*, 150(7):2844-57.
Smith, "Comparison of Biosequences" 1981 *Advances in Applied Mathematics*, 2:482-489.
Spanier, "Efficient generation of monoclonal antibodies against peptide in the context of MHCII using magnetic enrichment" Jun. 13, 2016 *Nat. Communications*, 7:11804; 11 pgs.
Stadinski, "Chromogranin A is an autoantigen in type 1 diabetes" 2010 *Nat. Immunol*, 11(3):225-31.
Swanson, "Generation of a Cross Reactive Antibody Against BDC2.5 CD4 T cell Mimotopes", Poster, American Physician Scientists Association Meeting, Apr. 1, 2016, Chicago, IL.
Swanson, "A Novel Cross Reactive Monoclonal Antibody Recognizing Insulin Peptides in MHC Class II Blocks Diabetogenic CD4 T Cells" Poster, University of Chicago & University of Minnesota Immunology Retreat, Apr. 12, 2017, Madison, WI.
Tam, "Sustained antigen availability during germinal center initiation enhances antibody responses to vaccination" Oct. 4, 2016 *PNAS*, 113(43):E6639-E6648.
Taylor, "Deletion and anergy of polyclonal B cells specific for ubiquitous membrane-bound self-antigen" 2012 *J. Exp. Med.*, 209:2065-2077.
Tubo, "Single Naive CD4+ T Cells from a Diverse Repertoire Produce Different Effector Cell Types during Infection" 2013 *Cell*, 153:785-796.
Uzzau, "Epitope tagging of chromosomal genes in *Salmonella*" 2001 *Proc. Natl. Acad. Sci. USA*, 98:15264-15269.
Wolpl, "Human monoclonal antibody with T-cell-like specificity recognizes MHC class I self-peptide presented by HLA-DR1 on activated cells" 1998 *Tissue Antigens*, 51:258-269.
Yokoyama, "Production of monoclonal antibodies" 2013 *Curr. Protoc. Immunol.*, 102:Unit 2.5.
Zhang, "Monoclonal antibody blocking the recognition of an insulin peptide-MHC complex modulates type 1 diabetes" 2014 *Proc. Natl. Acad. Sci. USA*, 111(7):2656-2661.
Zhong, "Production, specificity, and functionality of monoclonal antibodies to specific peptide-major histocompatibility complex class II complexes formed by processing of exogenous protein" 1997 *Proc. Natl. Acad. Sci. USA*, 94:13856-13861.

\* cited by examiner

FIG. 1
| MHCII IA$^{g7}$ groove position | -1 1 2 3 4 5 6 7 8 9 10 11 12 13 14 15 16 17 18 |
|---|---|
| BDC2.5 p31 | Y V R P L W V R M E |
| BDC2.5 p63 | R T R P L W V R M E |
| WE14 (AA 359-372) | W S R M D Q L A K E L T A E |
FIG. 2A
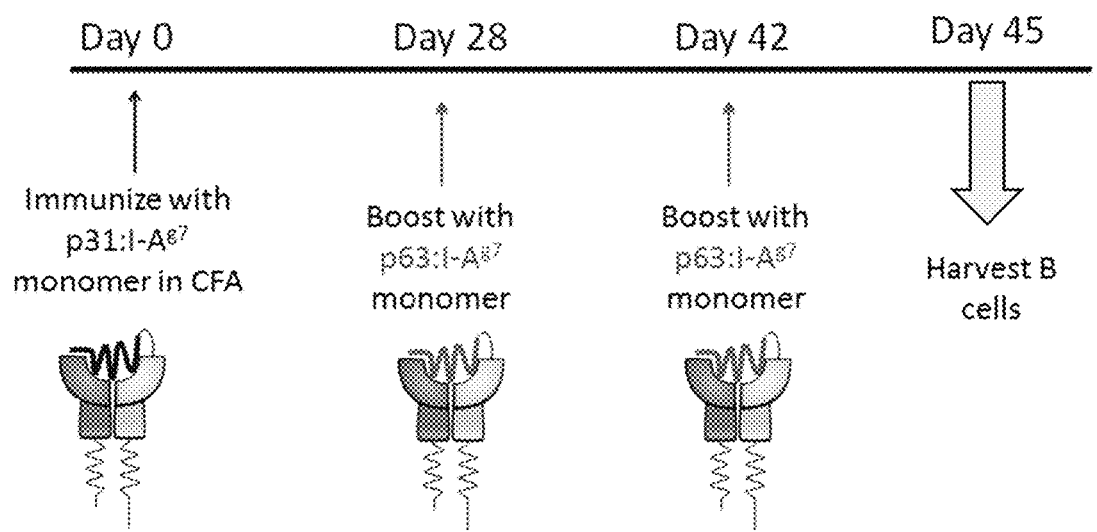
FIG. 2B
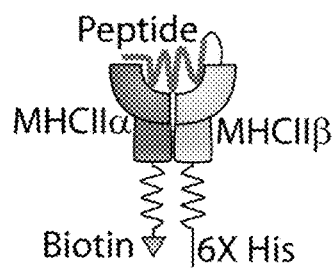

| native insulin B<sub>9-23</sub> | S H L V E A L Y L V C G E R G |
|---|---|
| (residue position) | 9 10 11 12 13 14 15 16 17 18 19 20 21 22 23 |
| IA<sup>g7</sup> groove position | -4 -3 -2 -1 1 2 3 4 5 6 7 8 9 10 |
| InsB<sub>9-23</sub> P8E | H L V E R L Y L V C G E E G |
| InsB<sub>9-23</sub> P8G | H L V E R L Y L V C G G E G |

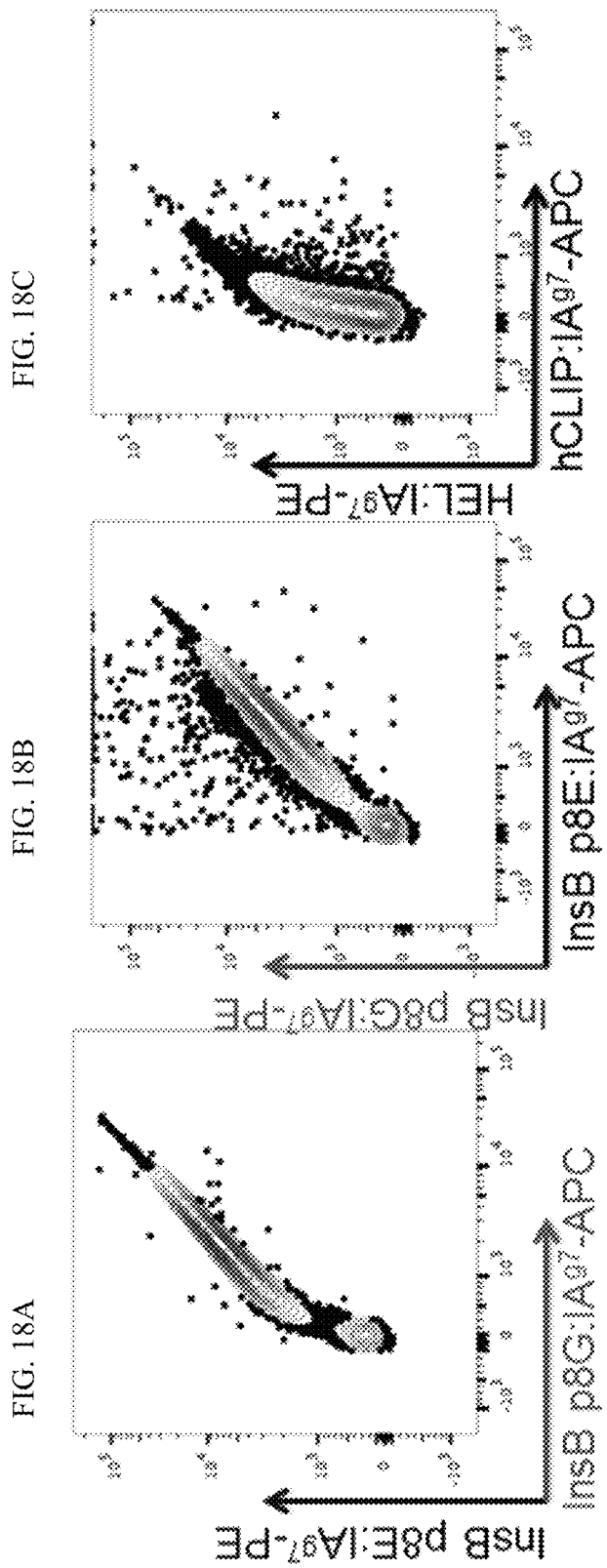

FIG. 21

4G8 Heavy Chain

Universal Primer
CTAATACGACTCACTATAGGGCAAGCAGTGGTATCAACGCAGAGTACATGGGGAGCTCTCTGACAGAGGAGGCCGG

TCCTGGATTCGATTCCCAGTTCCTCACATTCAGTCAGCACTGAACACAGACACCTCACC

Signal Peptide
ATGAACTTCGGGCTCAGC

V region
TTGATTTTCCTTGTCCTTATTTTAAAAGGTGTCCAGTGTGAAGTGCAGCTGGTGGAGTCTGGGGGAGGCTTAGTGA

AGCCTGGAGGGTCCCTGAAACTCTCCTGTGCAGCCTCTGGATTCACTTTCAGTAGCTATGCCATGTCTTGGGTTCGC

CAGTCTCCAGAGAAGAGGCTGGAGTGGGTCGCAGAAATTAGTAGTGGTGGTAATTACACCTACTATCCAGACACT

GTGACGGGCCGATTCACCATCTCCAGAGACAATGCCAAGAACACCCTGTACCTGGAAATGAGCAGTCTGAGGTCT

GAGGACACGGCCATGTATTACTGTACAAGGGATGAGGGTGGCATTACTTCGACTAGGGCCTGGTTTGCTTACTGG

GGCCAAGGGACTCTGGTCACTGTCTCTGCAGCCAAAACGACACCCCCATCTGTCTATCCACTGGCCCCTGGATCTG

CTGCCCAAACTAACTCCATGGTGACCCTGGGATGCCTGGTCAAGGGCTATTTCCCTGAGCCAGTGACAGTGACCTG

GAACTCTGGATCCCTGTCCAGCGGTGTGCACACCTTCCCAGCTGTCCTGCAGTCTGACCTCTACACTCTGAGCAGCT

CAGTGACTGTCCCCTCCAGCACCTGGCCCAGCGAGACCGTCACCTGCAACGTTGCCCACCCGGCCAGCAGCACCAA

Gene specific primer
GGTGGACAAGAAAATTGTGCCCAGGGATTGTGGTTGTAAGCCTTGCATAAAGCTTGGCGTAATC 4G8HC Translation

| Signal Peptide | FR1 | | CDR1 | FR2 |

M N F G L S L I F L V L I L K G V Q C E V Q L V E S G G G L V K P G G S L K L S C A A S G F T F S S Y A M S W V

CDR2    FR3
R Q S P E K R L E W V A E S S G G N Y T Y Y P D T V T G R F T I S R D N A K N T L Y L E M S S L R S E D T A M

Y Y C T R D E G G I T S T R A W F A Y W G Q G T L V T V S A A K T T P P S V Y P L A P G S A A Q T N S M V T L
    CDR3

4G8 Light Chain

| Universal Primer | Signal Peptide |
| --- | --- |
| GCAGTGGTATCAACGCAGAGT | ACATGGGGAATTAGCCAGGGAACAAAATTCAAATACACAATGGATTTTCTGGTG |

CAGATTTTCAGCTTCTTGCTAATCAGTGCCTCAGTTGCAATGTCCAGAGGA GAAAATGTGCTCACCCAGTCTCCAGC

AATCATGTCTGCATCTCCAGGGGAAAAGGTCACCATGACCTGCAGGGCCAGCTCAAGTGTAAGTTCCAGTTACTTG

CACTGGTACCAGCAGAAGTCAGGTGCCTCCCCCAAACTCTGGATTTATAGCACATCCAACTTGCCTTCTGGAGTCCC

TGCTCGCTTCAGTGGCGGTGGGTCTGGGACCTCTTACTCTCTCACAATCAGCAGTGTGGAGGCTGAAGATGCTGCC

ACTTATTACTGCCAGCAGTACAGTGGTTACCCACTCATGTACACGTTCGGAGGGGGGACCAAGCTGGAAATAAAA

CGGGCTGATGCTGCACCAACTGTATCCATCTTCCCACCATCCAGTGAGCAGTTAACATCTGGAGGTGCCTCAGTCG

TGTGCTTCTTGAACAACTTCTACCCCAAAGACATCAATGTCAAGTGGAAGATTGATGGCAGTGAACGACAAAATGG

CGTCCTGAACAGTTGGACTGATCAGGACAGCAAAGACAGCACCTACAGCATGAGCAGCACCCTCACGTTGACCAA

GGACGAGTATGAACGACATAACAGCTATACCTGTGAGGCCACTCACAAGACATCAACTTCACCC ATTGTCAAGAGC

TTCAACAGGAATGAGAAGCTTGGCGTAATCATGGT

4G8LC Translation

| Signal Peptide | FR1 | CDR1 | FR2 |
| --- | --- | --- | --- |
| M D F L V Q I F S F L L I S A S V A M S R G | E N V L T Q S P A I M S A S P G E K V T M T C R A S | S S V S S S Y | L |

| | CDR2 | FR3 |
| --- | --- | --- |
| H W Y Q Q K S G A S P K L W I Y | S T S | N L P S G V P A R F S G G G S G T S Y S L T I S S V E A E D A A T Y Y C |

| Q Q Y S G Y P L M Y T | F G G G T K L E I K R A D A A P T V S I F P P S S E Q L T S G G A S V V C F L N N F Y P K D |
| --- | --- |
| CDR3 | |

Anti-PE Clone 1 Light Chain

Signal Peptide
ATGGAGTTTCAGACCCAGGTCTTTGTATTCGTGTTGCTCTGGTTGTCTGGTGTTGATGGA

V region
GACATTGTGATGACCCAGTCTCAAAAATTCATGTCCACATCAGTAGGAGACAGGGTCAG
CATCACCTGCAAGGCCAGTCAGAATGTTCGTACTGCTGTAGCCTGGTATCAACAAAAAC
CAGGGCAGTCTCCTAAAGCACTGATTTACTTGGCATCCAACCGGCACACTGGAGTCCCT
GATCGCTTCACAGGCAGTGGATCTGGGACAGATTTCACTCTCACCGTTAGCTATGTGCA
ATCTGAAGACCTGGCAGATTATTTCTGTCTGCAACATTGGAATTATCCTCTCACGTTCGG
AGGGGGGACCAAGCTGGAAATAAAAC Anti-PE Clone 1 Light Chain Translation

| Signal Peptide | FR1 | CDR1 | FR2 | CDR2 |
| MEFQTQVFVFVLLWLSGVDG | DIVMTQSQKFMSTSVGDRVSITCKAS | QNVRTA | VAWYQQKPGQSPKALIY | LAS |

FR3
NRHTGVPDRFTGSGSGTDFTLTVSYVQSEDLADYFC | CDR3
LQHWNYPLT | FGGGTKLEIK

Anti-PE Clone 1 Heavy Chain

Signal Peptide
ATGGAATGGAGCTGGGTCTCTCTCTTCTTCCTGTCAGTAACTACAGGTGTCCACTCC

V region
CAGGTTCAGCTGCAACAGTCTGACGCTGAGTTGGTGAAACCTGGAACTTCAGTGAAC
ATTTCCTGCAAGGTTTCTGGCTACACCTTCACTGACCATACTTTTCACTGGATGAAACA
GAGGCCTGAAGAGGGCCTGGAATGGATTGGATATATTTTTATCCTAGAGATGGTACTACTA
AGTACAATGAGAAGTTCAAGGGCAAGGCCACATTGACTGCAGACAAATCCTCCAACA
CAGCCTACATGCAGTTCAACAGCCTGACATCTGAGGACTCTGCAGTCTATTTCTGTGCA
AGGACTACTAACTGGGACGCCCAGTTTACTTACTGGGGCCAAGGGACTCTGGTCACTG
TCTCTGCAG Anti-PE Clone 1 Heavy Chain Translation

| Signal Peptide | FR1 | CDR1 | FR2 | CDR2 |
| MEWSWVSLFFLSVTTGVHS | QVQLQQSDAELVKPGTSVNISCKVS | GYTFTDHT | FHWMKQRPEEGLEWIGY | FYPRDGTT |

FR3
KYNEKFKGKATLTADKSSNTAYMQFNSLTSEDSAVYFC | CDR3
ARTTNWDAQFTY | WGQGTLVTVSA

FIG. 23B

Anti-PE Clone 4 Light Chain

Signal Peptide
ATGGAGACAGACACACTCCTGCTATGGGTGCTGCTGCTCTGGGTTCCAGGTTCCACTGGT

V region
GACATTGTGCTGACACAGTCTCCTACTTCCTTAGCAATATCTCTGGGGCAGAGGGCCAC
CATCTCATGCAGGGCCAGCCAAAGTGTCAGTACATCTGCCTATGCTTATATGCACTGGTA
CCAACAGAAACCAGGACAGCCACCCAAACTCCTCATCAAGTATGCATCCAACCTAGAA
TCTGGGGTCCCTGCCAGGTTCAGTGGCAGTGGGTCTGGGACAGACTTCACCCTCAACA
TCCATCCTGTGGAGGAGGAGGATACTGCAACATATTACTGTCAGCACAGTTGGGAGATT
CCGTACACGTTCGGAGGGGGGACCAAGCTGGAAATTAAAC Anti-PE Clone 4 Light Chain Translation

| Signal Peptide | FR1 | CDR1 | FR2 | CDR2 |
| METDTLLLWVLLLWVPGSTG | DIVLTQSPTSLAISLGQRATISCRAS | QSVSTSAYAY | MHWYQQKPGQPPKLLIK | YAS |

FR3
NLESGVPARFSGSGSGTDFTLNIHPVEEEDTATYYC | CDR3: QHSWEIPYT | FGGGTKLEIK

Anti-PE Clone 4 Heavy Chain

Signal Peptide
ATGGGATGGAGCTGGATCTTTCTCCTCTTCCTGTCAGGAACTGCAGGTGTCCTCTCT

V region
GAGGTCCAGCTGCAACAGTCTGGACCTGAGCTGGTGAAGCCTGGGGCTTCAGTGAAG
ATACCCTGCAAGGCTTCTGGATACACATTCACTGACTACAACATGGACTGGGTGAAGCA
GAGCCATGGAAAGAGCCTTGAGTGGATTGGACATATTAATCCTAACAATGGTGGTACTA
TCTACAACCAGAAATTTAAGGGCAAGGCCACATTGACTGTAGACAAGTCCTCCAGCAC
AGCCTACATGGAGCTCCGCAGCCTGACATCTGAGGACACTGCAGTCTATTACTGTGCAA
GAACATATTACTACGGTAGTAGGACGAGGTACTTTGACTACTGGGGCCAAGGCACCAC
TCTCGCAGTCTCCTCAG Anti-PE Clone 4 Heavy Chain Translation

| Signal Peptide | FR1 | CDR1 | FR2 | CDR2 |
| MGWSWIFLFLSGTAGVLS | EVQLQQSGPELVKPGASVKIPCKAS | GYTFTDYN | MDWVKQSHGKSLEWIGH | INPNNGGT |

FR3
IYNQKFKGKATLTVDKSSSTAYMELRSLTSEDTAVYYC | CDR3: ARTYYYGSRTRYFDY | WGQGTTLAVSS

FIG. 23C

Anti-PE Clone 5 Light Chain

| Signal Peptide |
|---|
| ATGGATTCACAGGCCCAGGTTCTTATGTTACTGCTGCTATGGGTATCTGGTACCTGTGGG |

| V region |
|---|
| GACATTGTGATGTCACAGTCTCCATCCTCCCTAGTTGTGTCAGTTGGAGAGAAGGTTAC
TATGAGCTGCAAGTCCAGTCAGAGCCTTTTATATAGTAGCAATCAAAAGAACTACTTGG
CCTGGTACCAGCAGAAACCAGGGCAGTCTCCTAAAGTGCTGATTTACTGGGCATCCAC
TAGGGAATCTGGGGTCCCTGATCGCTTCACAGGCACTGGATCTGGGACAGATTTCACT
CTCACCATCAGCAGTGTGAAGGCTGAAGACCTGGCAGTTTATTCCTGTCAGCAATATTA
TAGTTCTCCGTGGACGTTCGGAGGAGGCACCACGCTGGAAATCAAAC |

Anti-PE Clone 5 Light Chain Translation

| Signal Peptide | FR1 | CDR1 | FR2 | CDR2 |
|---|---|---|---|---|
| MDSQAQVLMLLLWVSGTCG | DIVMSQSPSSLVVSVGEKVTMSCKSS | QSLLYSSNQKNY | LAWYQQKPGQSPKVLIY | WAS |

| FR3 | CDR3 | |
|---|---|---|
| TRESGVPDRFTGTGSGTDFTLTISSVKAEDLAVYSC | QQYYSSPWT | FGGGTTLEIK |

Anti-PE Clone 5 Heavy Chain

| Signal Peptide |
|---|
| ATGGGATGGAGCTGGATCTTTCTCTTTCTCCTGTCAGGAACTGCAGGTGTCCTCTCT |

| V region |
|---|
| GAGGTCCAGCTGCAACAATCTGGACCTGAGCTGGTGAAGCCTGGGGCTTCAGTGAAG
ATATCCTGTAAGGCTTCTGGATACACGTTCACTGACTACTACATGAACTGGGTGAAGCA
GAGCCATGGAAAGAGCCTTGAGTGGATTGGAGATATTAATCCTAACAATGATGTTACTA
GCTACAACCGGAAGTTCAAGGGCAAGGCCACATTGACTATAGACAAGTCCTCCACCAC
AGCCTACATGGAGCTCCGCAGCCTGACATCTGAGGACTCTACAGTCTATTACTGTGCAA
GAGGGGGGAGGATCTACTATGACCACGACGGGTTTGCTTACTGGGGCCAAGGGACTC
TGGTCACTGTCTCTGCAG |

Anti-PE Clone 5 Heavy Chain Translation

| Signal Peptide | FR1 | CDR1 | FR2 | CDR2 |
|---|---|---|---|---|
| MGWSWIFLFLLSGTAGVLS | EVQLQQSGPELVKPGASVKISCKAS | GYTFTDYY | MNWVKQSHGKSLEWIGD | INPNNDVT |

| FR3 | CDR3 | |
|---|---|---|
| SYNRKFKGKATLTIDKSSTTAYMELRSLTSEDSTVYYC | ARGGRIYYDHDGFAY | WGQGTLVTVSA |

SEQUENCE LISTING

```
<160> NUMBER OF SEQ ID NOS: 30

<210> SEQ ID NO 1
<211> LENGTH: 898
<212> TYPE: DNA
<213> ORGANISM: artificial
<220> FEATURE:
<223> OTHER INFORMATION: heavy chain XRI1

<400> SEQUENCE: 1
ctaatacgac tcactatagg gcaagcagtg gtatcaacgc agagtacatg gggagctctg      60
acagaggagg ccggtcctgg attcgattcc cagttcctca cattcagtca gcactgaaca     120
cagacacctc accatgaact tcgggctcag cttgattttc cttgtcctta ttttaaaagg     180
tgtccagtgt gaagtgcagc tggtggagtc tggggggaggc ttagtgaagc ctggagggtc    240
cctgaaactc tcctgtgcag cctctggatt cactttcagt agctatgcca tgtcttgggt    300
tcgccagtct ccagagaaga gctggagtg gtcgcagaa attagtagtg gtggtaatta     360
cacctactat ccagacactg tgacgggccg attcaccatc tccagagaca atgccaagaa    420
caccctgtac ctggaaatga gcagtctgag gtctgaggac acggccatgt attactgtac    480
aagggatgag ggtggcatta cttcgactag ggcctggttt gcttactggg gccaagggac    540
tctggtcact gtctctgcag ccaaaacgac accccatct gtctatccac tggcccctgg    600
atctgctgcc caaactaact ccatggtgac cctgggatgc ctggtcaagg ctatttccc    660 tgagccagtg acagtgacct ggaactctgg atccctgtcc agcggtgtgc acaccttccc    720
agctgtcctg cagtctgacc tctacactct gagcagctca gtgactgtcc cctccagcac    780
ctggcccagc gagaccgtca cctgcaacgt tgccacccg gccagcagca ccaaggtgga    840
caagaaaatt gtgcccaggg attgtggttg taagccttgc ataaagcttg gcgtaatc     898

<210> SEQ ID NO 2
<211> LENGTH: 243
<212> TYPE: PRT
<213> ORGANISM: artificial
<220> FEATURE:
<223> OTHER INFORMATION: heavy chain XRI1

<400> SEQUENCE: 2

Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Ser Pro Glu Lys Arg Leu
    50                  55                  60

Glu Trp Val Ala Glu Ile Ser Ser Gly Gly Asn Tyr Thr Tyr Tyr Pro
65                  70                  75                  80

Asp Thr Val Thr Gly Arg Phe Thr Ile Ser Arg Asp Asn Ala Lys Asn
                85                  90                  95

Thr Leu Tyr Leu Glu Met Ser Ser Leu Arg Ser Glu Asp Thr Ala Met
            100                 105                 110
```

Tyr Tyr Cys Thr Arg Asp Glu Gly Gly Ile Thr Ser Thr Arg Ala Trp
        115                 120                 125

Phe Ala Tyr Trp Gly Gln Gly Thr Leu Val Thr Val Ser Ala Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp

<210> SEQ ID NO 3
<211> LENGTH: 794
<212> TYPE: DNA
<213> ORGANISM: artificial
<220> FEATURE:
<223> OTHER INFORMATION: light chain XRI1

<400> SEQUENCE: 3
gcagtggtat caacgcagag tacatgggga attagccagg gaacaaaatt caaatacaca      60
atggattttc tggtgcagat tttcagcttc ttgctaatca gtgcctcagt tgcaatgtcc     120
agaggagaaa atgtgctcac ccagtctcca gcaatcatgt ctgcatctcc aggggaaaag     180
gtcaccatga cctgcagggc cagctcaagt gtaagttcca gttacttgca ctggtaccag     240
cagaagtcag gtgcctcccc caaactctgg atttatagca catccaactt gccttctgga     300
gtccctgctc gcttcagtgg cggtgggtct gggacctctt actctctcac aatcagcagt     360
gtggaggctg aagatgctgc cacttattac tgccagcagt acagtggtta cccactcatg     420
tacacgttcg gagggggac caagctggaa ataaaacggg ctgatgctgc accaactgta     480
tccatcttcc caccatccag tgagcagtta acatctggag gtgcctcagt cgtgtgcttc     540
ttgaacaact tctaccccaa agacatcaat gtcaagtgga gattgatgg cagtgaacga     600 caaaatggcg tcctgaacag ttggactgat caggacagca agacagcac ctacagcatg     660 agcagcaccc tcacgttgac caaggacgag tatgaacgac ataacagcta cctgtgag     720 gccactcaca agacatcaac ttcacccatt gtcaagagct caacaggaa tgagaagctt     780 ggcgtaatca tggt                                                         794

<210> SEQ ID NO 4
<211> LENGTH: 216
<212> TYPE: PRT
<213> ORGANISM: artificial
<220> FEATURE:
<223> OTHER INFORMATION: light chain XRI1

<400> SEQUENCE: 4

Met Asp Phe Leu Val Gln Ile Phe Ser Phe Leu Leu Ile Ser Ala Ser
1               5                   10                  15

Val Ala Met Ser Arg Gly Glu Asn Val Leu Thr Gln Ser Pro Ala Ile
        20                  25                  30

Met Ser Ala Ser Pro Gly Glu Lys Val Thr Met Thr Cys Arg Ala Ser
        35                  40                  45

Ser Ser Val Ser Ser Ser Tyr Leu His Trp Tyr Gln Gln Lys Ser Gly
    50                  55                  60

Ala Ser Pro Lys Leu Trp Ile Tyr Ser Thr Ser Asn Leu Pro Ser Gly
65                  70                  75                  80

Val Pro Ala Arg Phe Ser Gly Gly Ser Gly Thr Ser Tyr Ser Leu
                85                  90                  95

Thr Ile Ser Ser Val Glu Ala Glu Asp Ala Ala Thr Tyr Tyr Cys Gln
                100                 105                 110

Gln Tyr Ser Gly Tyr Pro Leu Met Tyr Thr Phe Gly Gly Gly Thr Lys
            115                 120                 125

Leu Glu Ile Lys Arg Ala Asp Ala Ala Pro Thr Val Ser Ile Phe Pro
130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser
        210                 215

<210> SEQ ID NO 5
<211> LENGTH: 10
<212> TYPE: PRT
<213> ORGANISM: artificial
<220> FEATURE:
<223> OTHER INFORMATION: p63 peptide

<400> SEQUENCE: 5

Arg Thr Arg Pro Leu Trp Val Arg Met Glu
1               5                   10

<210> SEQ ID NO 6
<211> LENGTH: 10
<212> TYPE: PRT
<213> ORGANISM: artificial
<220> FEATURE:
<223> OTHER INFORMATION: p31 peptide

<400> SEQUENCE: 6

Tyr Val Arg Pro Leu Trp Val Arg Met Glu
1               5                   10

<210> SEQ ID NO 7
<211> LENGTH: 20
<212> TYPE: PRT
<213> ORGANISM: artificial
<220> FEATURE:
<223> OTHER INFORMATION: OVA141-160 peptide

<400> SEQUENCE: 7

Cys Ala Arg Glu Leu Ile Asn Ser Trp Val Glu Ser Gln Thr Asn Gly
1               5                   10                  15

Ile Ile Arg Asn
        20

<210> SEQ ID NO 8
<211> LENGTH: 14
<212> TYPE: PRT
<213> ORGANISM: artificial
<220> FEATURE:
<223> OTHER INFORMATION: 2W peptide

<400> SEQUENCE: 8

Glu Ala Trp Gly Ala Leu Ala Asn Trp Ala Val Asp Ser Ala
1               5                   10

<210> SEQ ID NO 9
<211> LENGTH: 14
<212> TYPE: PRT
<213> ORGANISM: artificial
<220> FEATURE:
<223> OTHER INFORMATION: antigenic peptide

<400> SEQUENCE: 9

His Leu Val Glu Arg Leu Tyr Leu Val Cys Gly Glu Glu Gly
1               5                   10

<210> SEQ ID NO 10
<211> LENGTH: 12
<212> TYPE: PRT
<213> ORGANISM: artificial
<220> FEATURE:
<223> OTHER INFORMATION: antigenic peptide

<400> SEQUENCE: 10

Asn Glu Lys Tyr Ala Gln Ala Tyr Pro Asn Val Ser
1               5                   10

<210> SEQ ID NO 11
<211> LENGTH: 36
<212> TYPE: DNA
<213> ORGANISM: artificial
<220> FEATURE:
<223> OTHER INFORMATION: primer

<400> SEQUENCE: 11
gattacgcca agctttatgc aaggcttaca accaca                         36

<210> SEQ ID NO 12
<211> LENGTH: 41
<212> TYPE: DNA
<213> ORGANISM: artificial
<220> FEATURE:
<223> OTHER INFORMATION: primer

<400> SEQUENCE: 12
gattacgcca agcttcacaa ttttcttgtc caccttggtg c                   41

<210> SEQ ID NO 13
<211> LENGTH: 42
<212> TYPE: DNA
<213> ORGANISM: artificial
<220> FEATURE:
<223> OTHER INFORMATION: primer

<400> SEQUENCE: 13
gattacgcca agcttctcat tcctgttgaa gctcttgaca at                  42

```
<210> SEQ ID NO 14
<211> LENGTH: 42
<212> TYPE: DNA
<213> ORGANISM: artificial
<220> FEATURE:
<223> OTHER INFORMATION: primer

<400> SEQUENCE: 14
gattacgcca agcttacact cagcacggga caaactcttc tc                42

<210> SEQ ID NO 15
<211> LENGTH: 42
<212> TYPE: DNA
<213> ORGANISM: artificial
<220> FEATURE:
<223> OTHER INFORMATION: primer

<400> SEQUENCE: 15
gattacgcca agcttacact ctgcaggaga cagactcttt tc                42

<210> SEQ ID NO 16
<211> LENGTH: 14
<212> TYPE: PRT
<213> ORGANISM: artificial
<220> FEATURE:
<223> OTHER INFORMATION: WE14, a cleavage product of Chromogranin A

<400> SEQUENCE: 16

Trp Ser Arg Met Asp Gln Leu Ala Lys Glu Leu Thr Ala Glu
1               5                   10

<210> SEQ ID NO 17
<211> LENGTH: 15
<212> TYPE: PRT
<213> ORGANISM: artificial
<220> FEATURE:
<223> OTHER INFORMATION: antigenic peptide

<400> SEQUENCE: 17

Ser His Leu Val Glu Ala Leu Tyr Leu Val Cys Gly Glu Arg Gly
1               5                   10                  15

<210> SEQ ID NO 18
<211> LENGTH: 14
<212> TYPE: PRT
<213> ORGANISM: artificial
<220> FEATURE:
<223> OTHER INFORMATION: antigenic peptide

<400> SEQUENCE: 18

His Leu Val Glu Arg Leu Tyr Leu Val Cys Gly Gly Glu Gly
1               5                   10

<210> SEQ ID NO 19
<211> LENGTH: 382
<212> TYPE: DNA
<213> ORGANISM: artificial
<220> FEATURE:
<223> OTHER INFORMATION: light chain sequence

<400> SEQUENCE: 19
atggagtttc agacccaggt ctttgtattc gtgttgctct ggttgtctgg tgttgatgga    60
gacattgtga tgacccagtc tcaaaaattc atgtccacat cagtaggaga cagggtcagc    120
atcacctgca aggccagtca gaatgttcgt actgctgtag cctggtatca acaaaaacca    180
gggcagtctc ctaaagcact gatttacttg gcatccaacc ggcacactgg agtccctgat    240
```

```
cgcttcacag gcagtggatc tgggacagat tcactctca ccgttagcta tgtgcaatct    300
gaagacctgg cagattattt ctgtctgcaa cattggaatt atcctctcac gttcggaggg    360
gggaccaagc tggaaataaa ac                                              382
```

<210> SEQ ID NO 20
<211> LENGTH: 127
<212> TYPE: PRT
<213> ORGANISM: artificial
<220> FEATURE:
<223> OTHER INFORMATION: light chain sequence

<400> SEQUENCE: 20

```
Met Glu Phe Gln Thr Gln Val Phe Val Phe Val Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Ile Thr Cys Lys Ala Ser Gln Asn
        35                  40                  45

Val Arg Thr Ala Val Ala Trp Tyr Gln Gln Lys Pro Gly Gln Ser Pro
    50                  55                  60

Lys Ala Leu Ile Tyr Leu Ala Ser Asn Arg His Thr Gly Val Pro Asp
65                  70                  75                  80

Arg Phe Thr Gly Ser Gly Ser Gly Thr Asp Phe Thr Leu Thr Val Ser
                85                  90                  95

Tyr Val Gln Ser Glu Asp Leu Ala Asp Tyr Phe Cys Leu Gln His Trp
            100                 105                 110

Asn Tyr Pro Leu Thr Phe Gly Gly Gly Thr Lys Leu Glu Ile Lys
        115                 120                 125
```

<210> SEQ ID NO 21
<211> LENGTH: 415
<212> TYPE: DNA
<213> ORGANISM: artificial
<220> FEATURE:
<223> OTHER INFORMATION: heavy chain sequence

<400> SEQUENCE: 21

```
atggaatgga gctgggtctc tctcttcttc ctgtcagtaa ctacaggtgt ccactcccag     60
gttcagctgc aacagtctga cgctgagttg gtgaaacctg aacttcagt gaacatttcc    120 tgcaaggttt ctggctacac cttcactgac atactttc actggatgaa acagaggcct    180
gaagagggcc tggaatggat tggatatttt tatcctagag atggtactac taagtacaat    240
gagaagttca gggcaaggc cacattgact gcagacaaat cctccaacac agcctacatg    300
cagttcaaca gcctgacatc tgaggactct gcagtctatt tctgtgcaag gactactaac    360
tgggacgccc agtttactta ctggggccaa gggactctgg tcactgtctc tgcag        415
```

<210> SEQ ID NO 22
<211> LENGTH: 138
<212> TYPE: PRT
<213> ORGANISM: artificial
<220> FEATURE:
<223> OTHER INFORMATION: heavy chain sequence

<400> SEQUENCE: 22

```
Met Glu Trp Ser Trp Val Ser Leu Phe Phe Leu Ser Val Thr Thr Gly
1               5                   10                  15
```

```
Val His Ser Gln Val Gln Leu Gln Gln Ser Asp Ala Glu Leu Val Lys
            20                  25                  30

Pro Gly Thr Ser Val Asn Ile Ser Cys Lys Val Ser Gly Tyr Thr Phe
        35                  40                  45

Thr Asp His Thr Phe His Trp Met Lys Gln Arg Pro Glu Glu Gly Leu
    50                  55                  60

Glu Trp Ile Gly Tyr Phe Tyr Pro Arg Asp Gly Thr Thr Lys Tyr Asn
65                  70                  75                  80

Glu Lys Phe Lys Gly Lys Ala Thr Leu Thr Ala Asp Lys Ser Ser Asn
                85                  90                  95

Thr Ala Tyr Met Gln Phe Asn Ser Leu Thr Ser Glu Asp Ser Ala Val
            100                 105                 110

Tyr Phe Cys Ala Arg Thr Thr Asn Trp Asp Ala Gln Phe Thr Tyr Trp
        115                 120                 125

Gly Gln Gly Thr Leu Val Thr Val Ser Ala
    130                 135
```

```
<210> SEQ ID NO 23
<211> LENGTH: 394
<212> TYPE: DNA
<213> ORGANISM: artificial
<220> FEATURE:
<223> OTHER INFORMATION: light chain sequence

<400> SEQUENCE: 23
atggagacag acacactcct gctatgggtg ctgctgctct ggttccagg  ttccactggt        60 gacattgtgc tgacacagtc tcctacttcc ttagcaatat ctctgggca  gagggccacc       120 atctcatgca gggccagcca aagtgtcagt acatctgcct atgcttatat gcactggtac       180
caacagaaac aggacagcc  acccaaactc ctcatcaagt atgcatccaa cctagaatct       240
ggggtccctg ccaggttcag tgcagtgggt ctgggacag  acttcaccct caacatccat       300
cctgtggagg aggaggatac tgcaacatat tactgtcagc acagtgggga gattccgtac       360
acgttcggag gggggaccaa gctggaaatt aaac                                   394
```

```
<210> SEQ ID NO 24
<211> LENGTH: 131
<212> TYPE: PRT
<213> ORGANISM: artificial
<220> FEATURE:
<223> OTHER INFORMATION: light chain sequence

<400> SEQUENCE: 24

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Thr Ser Leu Ala
            20                  25                  30

Ile Ser Leu Gly Gln Arg Ala Thr Ile Ser Cys Arg Ala Ser Gln Ser
        35                  40                  45

Val Ser Thr Ser Ala Tyr Ala Tyr Met His Trp Tyr Gln Gln Lys Pro
    50                  55                  60

Gly Gln Pro Pro Lys Leu Leu Ile Lys Tyr Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Thr Ala Thr Tyr Tyr Cys
            100                 105                 110
```

Gln His Ser Trp Glu Ile Pro Tyr Thr Phe Gly Gly Gly Thr Lys Leu
         115                 120                 125

Glu Ile Lys
    130

<210> SEQ ID NO 25
<211> LENGTH: 424
<212> TYPE: DNA
<213> ORGANISM: artificial
<220> FEATURE:
<223> OTHER INFORMATION: heavy chain sequence

<400> SEQUENCE: 25
atgggatgga gctggatctt tctcctcttc ctgtcaggaa ctgcaggtgt cctctctgag      60
gtccagctgc aacagtctgg acctgagctg gtgaagcctg gggcttcagt gaagataccc     120
tgcaaggctt ctggatacac attcactgac tacaacatgg actgggtgaa gcagagccat     180
ggaaagagcc ttgagtggat tggacatatt aatcctaaca atggtggtac tatctacaac     240
cagaaattta agggcaaggc cacattgact gtagacaagt cctccagcac agcctacatg     300
gagctccgca gcctgacatc tgaggacact gcagtctatt actgtgcaag aacatattac     360
tacggtagta ggacgaggta ctttgactac tggggccaag gcaccactct cgcagtctcc     420
tcag                                                                  424

<210> SEQ ID NO 26
<211> LENGTH: 141
<212> TYPE: PRT
<213> ORGANISM: artificial
<220> FEATURE:
<223> OTHER INFORMATION: heavy chain sequence

<400> SEQUENCE: 26

Met Gly Trp Ser Trp Ile Phe Leu Leu Phe Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Pro Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly His Ile Asn Pro Asn Asn Gly Gly Thr Ile Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Thr Tyr Tyr Gly Ser Arg Thr Arg Tyr Phe
        115                 120                 125

Asp Tyr Trp Gly Gln Gly Thr Thr Leu Ala Val Ser Ser
    130                 135                 140

<210> SEQ ID NO 27
<211> LENGTH: 400
<212> TYPE: DNA
<213> ORGANISM: artificial
<220> FEATURE:
<223> OTHER INFORMATION: light chain sequence

<400> SEQUENCE: 27

| | | | |
|---|---|---|---|
| atggattcac aggcccaggt tcttatgtta ctgctgctat gggtatctgg tacctgtggg | 60 |
| gacattgtga tgtcacagtc tccatcctcc ctagttgtgt cagttggaga gaaggttact | 120 |
| atgagctgca agtccagtca gagccttttta tatagtagca atcaaaagaa ctacttggcc | 180 |
| tggtaccagc agaaaccagg gcagtctcct aaagtgctga tttactgggc atccactagg | 240 |
| gaatctgggg tccctgatcg cttcacaggc actggatctg ggacagattt cactctcacc | 300 |
| atcagcagtg tgaaggctga agacctggca gtttattcct gtcagcaata ttatagttct | 360 |
| ccgtggacgt tcggaggagg caccacgctg gaaatcaaac | 400 |

<210> SEQ ID NO 28
<211> LENGTH: 133
<212> TYPE: PRT
<213> ORGANISM: artificial
<220> FEATURE:
<223> OTHER INFORMATION: light chain sequence

<400> SEQUENCE: 28

Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Val
            20                  25                  30

Val Ser Val Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Val Leu Ile Tyr Trp Ala Ser Thr Arg
65                  70                  75                  80

Glu Ser Gly Val Pro Asp Arg Phe Thr Gly Thr Gly Ser Gly Thr Asp
                85                  90                  95

Phe Thr Leu Thr Ile Ser Ser Val Lys Ala Glu Asp Leu Ala Val Tyr
            100                 105                 110

Ser Cys Gln Gln Tyr Tyr Ser Ser Pro Trp Thr Phe Gly Gly Gly Thr
        115                 120                 125

Thr Leu Glu Ile Lys
    130

<210> SEQ ID NO 29
<211> LENGTH: 424
<212> TYPE: DNA
<213> ORGANISM: artificial
<220> FEATURE:
<223> OTHER INFORMATION: heavy chain sequence

<400> SEQUENCE: 29

| | | | |
|---|---|---|---|
| atgggatgga gctggatctt tctctttctc ctgtcaggaa ctgcaggtgt cctctctgag | 60 |
| gtccagctgc aacaatctgg acctgagctg gtgaagcctg ggcttcagt gaagatatcc | 120 |
| tgtaaggctt ctggatacac gttcactgac tactacatga actgggtgaa gcagagccat | 180 |
| ggaaagagcc ttgagtggat tggagatatt aatcctaaca atgatgttac tagctacaac | 240 |
| cggaagttca aggcaaggc cacattgact atagacaagt cctccaccac agcctacatg | 300 |
| gagctccgca gcctgacatc tgaggactct acagtctatt actgtgcaag agggggagg | 360 |
| atctactatg accacgacgg gtttgcttac tggggccaag ggactctggt cactgtctct | 420 |
| gcag | 424 |

```
<210> SEQ ID NO 30
<211> LENGTH: 141
<212> TYPE: PRT
<213> ORGANISM: artificial
<220> FEATURE:
<223> OTHER INFORMATION: heavy chain sequence

<400> SEQUENCE: 30

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Tyr Met Asn Trp Val Lys Gln Ser His Gly Lys Ser Leu
    50                  55                  60

Glu Trp Ile Gly Asp Ile Asn Pro Asn Asn Asp Val Thr Ser Tyr Asn
65                  70                  75                  80

Arg Lys Phe Lys Gly Lys Ala Thr Leu Thr Ile Asp Lys Ser Ser Thr
                85                  90                  95

Thr Ala Tyr Met Glu Leu Arg Ser Leu Thr Ser Glu Asp Ser Thr Val
                100                 105                 110

Tyr Tyr Cys Ala Arg Gly Gly Arg Ile Tyr Tyr Asp His Asp Gly Phe
            115                 120                 125

Ala Tyr Trp Gly Gln Gly Thr Leu Val Thr Val Ser Ala
    130                 135                 140
```

MONOCLONAL ANTIBODIES DIRECTED TO PEPTIDE IN THE CONTEXT OF MHC AND METHODS OF MAKING AND USING MONOCLONAL ANTIBODIES

CONTINUING APPLICATION DATA

This application claims the benefit of U.S. Provisional Application Ser. No. 62/485,762, filed Apr. 14, 2017, which is incorporated by reference herein in its entirety.

GOVERNMENT FUNDING

This invention was made with government support under AI106791, AI118635 and AI035296 awarded by the National Institutes of Health. The government has certain rights in the invention.

SEQUENCE LISTING

This application contains a Sequence Listing electronically submitted to the United States Patent and Trademark Office via EFS-Web as an ASCII text file entitled "110-05770101_ST25.txt" having a size of 21 kilobytes and created on Apr. 13, 2018. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

BACKGROUND

The first monoclonal antibody (MAb) reactive to a defined protein antigen was reported in 1975 (Kohler and Milstein, *Nature* 256, 495-497 (1975)). The utility and broad use of MAbs in biological systems earned Kohler and Milstein the Nobel Prize for medicine in 1984. But the generation of MAbs that target peptide in the context of MHCII has only occurred a few times since 1975. (Murphy et al. *Nature* 338:765-768 (1989); Zhang et al. *Proc Natl Acad Sci USA* 111:2656-2661 (2014); Wolpl et al. *Tissue Antigens* 51, 258-269 (1998); Muraille et al. *PLoS pathogens* 6:e1001154 (2010); Baldwin et al. J Exp Med 189, 13-24 (1999); Zhong et al. *Proc Natl Acad Sci USA* 94:13856-13861 (1997); Dadaglio et al. *Immunity* 6, 727-738 (1997).)

To generate a MAb using the traditional approach, mice are immunized, the responding B cells are isolated, fused to myeloma cells with hypoxanthine-aminopterin-thymidine (HAT) based selection, screened and sub-cloned to isolate monoclonal hybridomas (Yokoyama et al. *Curr Protoc Immunol* 102, Unit 2 5 (2013)). Screening requires the examination of hundreds or even thousands of clones for one MAb, creating a major bottleneck. This approach typically yields fewer than 1 percent (%) hybridomas specific for a protein target antigen causing a prominent hurdle, both in time and resources. Moreover, this traditional approach is not specifically designed to generate peptide:MHC (p:MHC) reactive MAbs, and B cell tolerance against self-MHC adds to the difficulty of generating p:MHC reactive MAbs.

SUMMARY OF THE INVENTION

This disclosure describes phycoerythrin (PE) and peptide:MHCII (p:MHCII) reactive MAbs and methods to generate monoclonal antibodies including, for example, peptide:MHC (p:MHC) reactive MAbs.

In one aspect, this disclosure describes a method including: immunizing a subject with a composition including an antigen; isolating a population of cells from the subject; enriching a subpopulation of cells from the population of cells; and forming a hybridoma from a cell selected from the subpopulation of cells.

In some embodiments, the antigen includes a peptide-MHC complex (p:MHC), and enriching a subpopulation of cells includes excluding cells that do not bind to p:MHC. In some embodiments, the antigen includes a monomeric peptide-MHC complex. In some embodiments, the antigen includes at least two peptide-MHC complexes. Each peptide-MHC complex may include the same MHC, but the peptide of each peptide-MHC complex may be different. In some embodiments, the antigen includes a peptide-MHC Class I complex (p:MHCI) or a peptide-MHC Class II complex (p:MHCII). In some embodiments, the method includes immunizing a subject with a composition including an antigen including one peptide-MHC complex and subsequently immunizing the subject with a composition including an antigen including another peptide-MHC complex.

In some embodiments, excluding cells that do not bind to p:MHC includes excluding cells that bind to a peptide not bound to an MHC complex and/or to an MHC complex not bound to a peptide.

In some embodiments, enriching a subpopulation of cells includes enriching a subpopulation of cells capable of binding to a multimeric form of the antigen. The multimeric form of the antigen may include at least one of a biotin, a desthiobiotin, and a fluorescent biotin derivative. When a multimeric form of the antigen includes at least one of a marker and a photosynthetic pigment, excluding cells that do not bind to p:MHC may include excluding cells that bind to the marker or the photosynthetic pigment.

In some embodiments, enriching a subpopulation of cells includes excluding cells that bind to a second peptide-MHC complex, wherein the second peptide-MHC complex includes the same MHC complex as the p:MHC of the antigen used to immunize the subject, and further wherein the second peptide-MHC complex includes a different peptide than the p:MHC of the antigen used to immunize the subject.

In some embodiments, enriching the subpopulation of the cells includes using flow cytometric identification and/or sorting.

In some embodiments, enriching a subpopulation of cells further includes at least one of increasing the proportion of B cells in the population that bind the antigen, identifying expression of a lymphocyte marker, identifying mononuclear cells, identifying expression of a B cell marker, testing for viability, and testing for antigen specificity.

In some embodiments, the composition including an antigen further includes an adjuvant. When the composition includes an adjuvant, excluding cells that do not bind to p:MHC may include excluding cells that bind to the adjuvant.

In some embodiments, the method further includes screening the hybridoma for production of an antibody specific for the p:MHC.

In some embodiments, the subject is a mammal including, for example, a mouse, a humanized mouse, a rat or a rabbit.

In another aspect, this disclosure describes a monoclonal antibody. In some embodiments, the monoclonal antibody includes a heavy chain variable region of FS1, W6, or XRI1 and/or a light chain variable region polypeptide sequence of FS1, W6, or XRI1. In some embodiments, the monoclonal antibody includes a heavy chain variable region as disclosed in FIG. 23 and/or a light chain variable region polypeptide sequence as disclosed in FIG. 23.

In some embodiments, the monoclonal antibody includes a heavy chain variable region including a CDR of FS1, W6, or XRI1 and/or a light chain variable region including a CDR of FS1, W6, or XRI1. In some embodiments, the monoclonal antibody includes a heavy chain variable region including a CDR as disclosed in FIG. 23 and/or a light chain variable region including a CDR as disclosed in FIG. 23.

In a further aspect, this disclosure describes methods of using the monoclonal antibodies described herein.

The term "antibody" as used herein refers to a molecule that contains at least one antigen binding site that immunospecifically binds to a particular antigen target of interest. The term "antibody" thus includes but is not limited to a full length antibody and/or its variants, a fragment thereof, peptibodies and variants thereof, monoclonal antibodies (including full-length monoclonal antibodies), polyclonal antibodies, multispecific antibodies (e.g., bispecific antibodies) formed from at least two intact antibodies, human antibodies, humanized antibodies, and antibody mimetics that mimic the structure and/or function of an antibody or a specified fragment or portion thereof, including single chain antibodies and fragments thereof. Binding of an antibody to a target can cause a variety of effects, such as but not limited to where such binding modulates, decreases, increases, antagonizes, agonizes, mitigates, alleviates, blocks, inhibits, abrogates and/or interferes with at least one target activity or binding, or with receptor activity or binding, in vitro, in situ, and/or in vivo. The present disclosure, thus, encompasses antibody fragments capable of binding to a biological molecule (such as an antigen or receptor) or portions thereof, including but not limited to Fab, Fab' and F(ab')$_2$, pFc', Fd, a single domain antibody (sdAb), a variable fragment (Fv), a single-chain variable fragment (scFv) or a disulfide-linked Fv (sdFv); a diabody or a bivalent diabody; a linear antibody; a single-chain antibody molecule; and a multispecific antibody formed from antibody fragments. The antibody can be of any type (e.g., IgG, IgE, IgM, IgD, IgA and IgY), class (e.g., IgG1, IgG2, IgG3, IgG4, IgA1 and IgA2), or subclass.

The term "monoclonal antibody" as used herein refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which typically include different antibodies directed against different determinants (epitopes), each monoclonal antibody is directed against a single determinant on the antigen. The monoclonal antibodies can be synthesized by hybridoma cells uncontaminated by other immunoglobulin producing cells. Alternatively, the monoclonal antibody can be produced by cells stably or transiently transfected with the heavy and light chain genes encoding the monoclonal antibody.

The modifier "monoclonal" indicates the character of the antibody as being obtained from a substantially homogeneous population of antibodies, and is not to be construed as requiring engineering of the antibody by any particular method. In some embodiments, the term "monoclonal" is used herein to refers to an antibody that is derived from a clonal population of cells, including any eukaryotic, prokaryotic, or phage clone, and not the method by which the antibody was engineered.

As used herein, "isolated" refers to material removed from its original environment (e.g., the natural environment if it is naturally occurring), and thus is altered "by the hand of man" from its natural state.

As used herein "in vitro" is in cell culture and "in vivo" is within the body of a subject.

As used herein "sequence identity" between two polypeptides is determined by comparing the amino acid sequence of one polypeptide to the sequence of a second polypeptide. When discussed herein, whether any particular polypeptide is at least 40 percent (%), at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

Herein, "room temperature" is 62° F. to 78° F. or, more preferably, 65° F. to 75° F.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1 shows the MHC II peptide sequence groove position of two T cell activating mimotopes, peptide 31 (p31) (SEQ ID NO:6) and peptide 63 (p63) (SEQ ID NO:5), and WE14, a cleavage product of Chromogranin A (SEQ ID NO:16).

FIG. 2A shows an immunization and antigen-specific boost scheme to generate a cross-reactive monoclonal antibody using bound peptide 31 (p31)-IA$^{g7}$ monomer in complete Freund's adjuvant (CFA) and peptide 63 (p63)-IA$^{g7}$ monomer. FIG. 2B shows an exemplary bound peptide-MHCII (p:MHCII) monomer tagged with biotin and 6×His.

FIG. 7A shows flow cytometric analysis of p:MHCII-specific B cells before and 7 days post-immunization with p:MHCII monomer. Splenocytes from naïve and immunized mice were collected and stained for specific immunogen p:MHCII-PE and decoy p:MHCII APC tetramers and magnetically enriched using anti-PE and anti-APC magnetic beads. Germinal center B cells (GL7$^+$ and Intracellular Ig$^-$) and plasma cells (GL7$^-$ and intracellular Ig$^+$) were then identified from the various p:MHCII-specific B-cell populations binding these distinct tetramer reagents. p:MHCII-specific B cells were gated from streptavidin, APC and PE binding cells using SA-APC-DYLIGHT 755 or SA-PE-AF647 20. FIG. 7B shows a representative flow cytometric analysis of p63:IA$^{g7}$-enriched antigen-specific B cells obtained before myeloma fusion. Germinal center B cells (GL7$^+$ and Intracellular Ig$^-$) and plasma cells (GL7$^-$ and intracellular Ig$^+$) were then identified within the p63:IA$^{g7}$-PE tetramer specific B cells. Data are representative of two independent experiments with 2-5 mice per group.

FIG. 8(A-E) shows screening and functional validation of the FS1 MAb.

FIG. 9(A-C) shows functional validation of W6 (2W:IA$^b$) MAbs.

FIG. 10(A-B) shows in vivo blockade of T-cell proliferation and prevention of T-cell tolerance following FS1 administration.

FIG. 11(A-C) shows in vivo blockade of T-cell proliferation and prevention of bacterial clearance following W6 administration.

FIG. 11(B-C). Wild type 129 S1 mice were infected with *Salmonella Typhimurium* expressing 2W, and 14 days following infection mice were treated with blocking W6 MAb.

FIG. 17(A-B) shows validation of p:MHCII tetramers for B cell pulldown. NOD mice were immunized with 10 μg of InsB p8E:IA$^{g7}$ in CFA. After 14 days, secondary lymphoid organs were dual tetramer stained with InsB p8E:IA$^{g7}$-PE and p31:IA$^{g7}$-APC.

FIG. 18 (A-C) shows in vitro staining of Ins 4G8 hybridoma with IA$^{g7}$ tetramers. FIG. 18A and FIG. 18B show Ins 4G8 hybridomas bind both InsB p8G:IA$^{g7}$ and InsB p8E:IA$^{g7}$ tetramers. FIG. 18C shows Ins 4G8 hybridomas bind HEL:IA$^{g7}$ and hCLIP:IA$^{g7}$ with much lower affinity than p8G:IA$^{g7}$ and InsB p8E:IA$^{g7}$ tetramers.

20B) peptide stimulation with isotype control antibody treatment at days 0 and 2 (left panels of FIG. 20A and FIG. 20B) or XRI1 (4G8) treatment at days 0 and 2 (right panels of FIG. 20A and FIG. 20B).

FIG. 21 shows heavy chain XRI1 DNA (SEQ ID NO:1) and protein (SEQ ID NO:2) sequences (produced by clone Ins 4G8).

FIG. 22 shows light chain XRI1 DNA (SEQ ID NO:3) and protein (SEQ ID NO:4) sequences (produced by clone Ins 4G8).

FIG. 23 shows light chain and heavy chain DNA and protein sequences for the antibodies produced by clones of FIG. 14. FIG. 23A shows the light chain DNA sequence (SEQ ID NO:19), the light chain protein sequence (SEQ ID NO:20), the heavy chain DNA sequence (SEQ ID NO:21), and the heavy chain protein sequence (SEQ ID NO:22) of the antibody produced by Clone 1 of FIG. 14. FIG. 23B shows the light chain DNA sequence (SEQ ID NO:23), the light chain protein sequence (SEQ ID NO:24), the heavy chain DNA sequence (SEQ ID NO:25), and the heavy chain protein sequence (SEQ ID NO:26) of the antibody produced by Clone 4 of FIG. 14. FIG. 23C shows the light chain DNA sequence (SEQ ID NO:27), the light chain protein sequence (SEQ ID NO:28), the heavy chain DNA sequence (SEQ ID NO:29), and the heavy chain protein sequence (SEQ ID NO:30) of the antibody produced by Clone 5 of FIG. 14.

DETAILED DESCRIPTION OF ILLUSTRATIVE EMBODIMENTS

Figure 3:
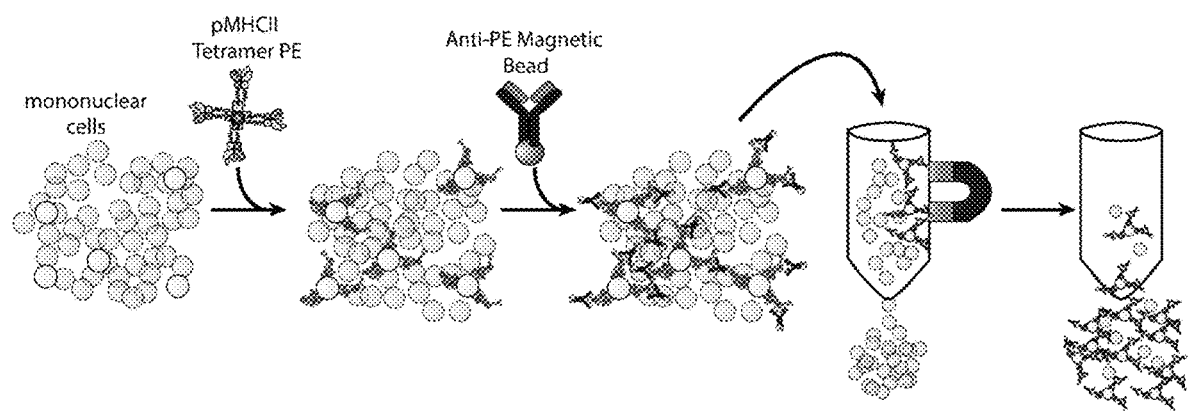
FIG. 3 shows magnetic enrichment and isolation of antibody-expressing cells produced according to the immunization scheme of FIG. 2. Briefly, a single cell suspension was made from splenocytes and cells from pooled lymph nodes (inguinal, brachial, cervical and axillary) from the immunized animal, and cells were labeled with a phycoerythrin (PE)-conjugated peptide:MHCII tetramer. After washing, cells were labeled with anti-PE microbeads, and a magnetic column system was used to enrich and isolate antibody-expressing cells bound to the microbeads.

This disclosure describes phycoerythrin (PE) and peptide:MHCII (p:MHCII) reactive MAbs and methods to generate monoclonal antibodies including, for example, peptide:MHC (p:MHC) reactive MAbs.

The monoclonal antibodies described herein recognize an antigen. In some embodiments, the antigen may include a peptide and/or a hapten. In some embodiments, the peptide and/or hapten may be conjugated to a carrier molecule. In some embodiments, the monoclonal antibodies described herein preferably recognize a peptide-MHC complex.

In some embodiments, the antigen may include a foreign antigen (e.g., a bacterial and/or viral antigen from an infected cell), an allogeneic antigen (e.g., an antigen recognized after transplantation), a tumor neo-antigen, and/or a self-antigen (e.g., a self-protein targeted during autoimmunity).

In some embodiments, the monoclonal antibodies described herein may recognize an antigen that includes a peptide-MHC complex (also referred to herein as peptide:MHC and/or p:MHC). In some embodiments, a peptide-MHC complex may include a foreign peptide. In some embodiments, a peptide-MHC complex may include an allogeneic peptide. In some embodiments, a peptide-MHC complex may include a self peptide. In some embodiments, a peptide-MHC complex may include a hybrid self-peptide. In some embodiments, a peptide-MHC complex may include a tumor antigen or a tumor neo-antigen.

In some embodiments, the MHC complex may be an MHC Class I complex. In some embodiments, the MHC complex may be an MHC Class II complex. In some embodiments, the MHC complex may be mammalian. In some embodiments, the mammal may include a human, a mouse, a dog, a rabbit, a non-human primate, a sheep, a cat, a horse, a cow, a chicken, etc. In some embodiments, the MHC complex may be non-mammalian including, for example, from an amphibian or a reptile. In some embodiments, the MHC complex may be human. For example, a human MHC Class I complex may include HLA-A, HLA-B, or HLA-C; a human MHC class II complex may include HLA-DP, HLA-DM, HLA-DOA, HLA-DOB, HLA-DQ, or HLA-DR. In some embodiments, the MHC complex may be murine. For example, a murine MHC Class I complex may include H-2D, H-2K, H-2L, H-2Q, H-2M, or H-2T. For example, a murine MHC Class II complex may include H-2A, H-2E, H-2M, or H-2O. Murine MHC may further include a haplotype. (See, e.g., Kuby Immunology, 4$^{th}$ Ed., 2000, Chapter 7 (providing a general description of MHC complexes in humans and mice); Mouse Alloantigens, BioLegend Resource page, available on the world wide web at biolegend.com/media_assets/support_resource/BioLegend Mouse_Alloantigens.pdf (providing commonly used laboratory mouse haplotypes and alloantigens).)

In some embodiments, including when the antigen includes a peptide-MHC complex, the peptide may be covalently linked to the MHC complex.

In some embodiments, an algorithm may be used predict peptide register binding leading to selection of p:MHC for use as an antigen. (See, e.g., Muraille et al. *PLoS pathogens* 6:1001154 (2010).)

In some embodiments, high throughput generation may be used to produce p:MHC monomers by peptide exchange (Day et al. *J Clin Invest* 112:831-842 (2003)).

In some embodiments, as described, for example, in Example 1, the antigen may include a peptide-MHC complex including p31:IA$^{g7}$ and/or p63:IA$^{g7}$. In an exemplary embodiment, as described, for example, in Example 2, the antigen may include a peptide-MHC complex including p31:IA$^{g7}$ or 2W:IA$^{b}$. As described, for example, in Examples 2 and 4, the antigen may include a peptide-MHC complex including p8G:IA$^{g7}$ or p8E:IA$^{b}$. In some embodiments, the peptide-MHC complex may include a cross reactive peptide MHC target. In some embodiments, the peptide-MHC complex may be specific for a single peptide:MHC target.

In some embodiments, as described, for example, in Example 1, the antigen may include phycoerythrin (PE).

The need for immunotherapeutics in the form of MAbs directed against p:MHCII is expected to increase as new pathways and novel antigens are identified during disease. As these targets are identified, there will be a great need to limit antigen specific T cell responses and the methodology described here may dramatically improve this capability over conventional methods.

In some embodiments, a method of making a monoclonal antibody as described herein includes immunizing a subject with a composition including the antigen. In some embodiments, the subject is a mammal. In some embodiments, a mammalian subject may include a human, a mouse, a dog, a rabbit, a rat, a non-human primate, a sheep, a cat, a horse, a cow, a chicken, etc. In some embodiments, the non-human mammal may be humanized; for example, a non-human mammal may include a humanized mouse. In some embodiments, the subject is a non-mammal including, for example, an amphibian or a reptile. Immunization may be performed using any suitable method or combination or methods known to one of skill in the art.

In some embodiments, immunization may include exposing the subject to at least one antigen one time, two times, three times, four times, or more than four times.

In some embodiments, immunization may include exposing the subject to multiple antigens. For example, in some embodiments, immunization may include exposing the subject to one antigen and boosting with a second antigen. Such an immunization scheme may be used to develop a cross-reactive target.

In some embodiments, immunization may preferably include exposing the subject to a monomeric form of the antigen. In some embodiments, immunization may include exposing the subject to a multimeric form of the antigen.

In some embodiments, a composition including the antigen may also include an adjuvant. In some embodiments, an adjuvant may include Monophosphoryl Lipid A (MPLA) complete Freund's adjuvant (CFA), incomplete Freund's adjuvant (IFA), alum, etc. In some embodiments, including, for example, when the adjuvant is MPLA, a composition including the antigen and adjuvant may preferably be introduced using dose escalation. (See for example, Tam et al., *Proc Natl Acad Sci USA* 113(43), E6639-E6648 (2016)). Additionally or alternatively, a composition may include whole cells which, in the absence of adjuvant, have been found to be highly immunogenic.

In some embodiments, the composition may also include, for example, buffering agents to help to maintain the pH in an acceptable range or preservatives to retard microbial growth. A composition may also include, for example, carriers, excipients, stabilizers, chelators, salts, or antimicrobial agents. Acceptable carriers, excipients, stabilizers, chelators, salts, preservatives, buffering agents, or antimicrobial agents, include, but are not limited to, buffers such as phosphate, citrate, and other organic acids; antioxidants including ascorbic acid and methionine; preservatives, such as sodium azide, octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; polypeptides; proteins, such as serum albumin, gelatin, or non-specific immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zinc (Zn)-protein complexes); and/or non-ionic surfactants such as TWEEN, PLURONICS, or polyethylene glycol (PEG).

In some embodiments, immunization may preferably include immunization with a peptide-MHC complex (p:MHC). The MHC complex may include an MHC Class I complex (MHCI) or an MHC Class II complex (MHCII). Immunization with p:MHC may induce a B cell response specific for that peptide in the context of MHC. For example, immunization with p:MHCII may induce a B cell response specific for that peptide in the context of MHCII.

In some embodiments, immunization may include immunizing with an antigen that comprises at least two peptide-MHC complexes. In some embodiments, the peptide-MHC complexes may include the same MHC, but the peptide of each peptide-MHC complex may be different. In some embodiments, the at least two peptide-MHC complexes may be introduced at different times.

In some embodiments, including for example, when the antigen is used to immunize a subject, the antigen may preferably be in a monomeric form. In some embodiments, when the antigen is used to immunize a subject, the antigen may be in a multimeric form.

In some embodiments, including for example, when the antigen is used to for select a subpopulation of cells capable of binding the antigen, the antigen may be in a monomeric or a multimeric form. In some embodiments, when the antigen is used to select for a subpopulation of cells capable of binding the antigen, the antigen is preferably in a multimeric form. A multimeric form of the antigen may include, for example, a dimeric antigen, a trimeric antigen, a tetrameric antigen, an octomeric antigen, a dodecamer antigen, or a higher order multimer of antigens.

For example, in some embodiments, the antigen may be linked to (e.g., conjugated to) a biotin, a desthiobiotin, and/or a fluorescent biotin derivative. Avidin and other biotin-binding proteins, including streptavidin and NeutrAvidin Protein, have the ability to bind up to four biotin molecules, allowing for the formation of a multimeric antigen. In some embodiments, a p:MHC may be linked to biotin, and an avidin-biotin interaction may be used to form a p:MHC multimer including, for example, a tetramer. In some embodiments the MHC complex of a p:MHC may be linked to biotin.

In some embodiments, a p:MHC may be linked to a histidine tag including, for example, 6×His. In some embodiments the MHC complex of a p:MHC may be linked to a histidine tag.

In some embodiments, the use of a multimeric antigen may allow for the enrichment of B cells reactive to the antigen by enabling the capture and enrichment of antigen-specific B cells. For example, in some embodiments, a subject may be immunized with a composition comprising an antigen, wherein the antigen comprises a monomeric peptide-MHC complex (p:MHC); a population of cells may be isolated from the subject; and a subpopulation of cells may be enriched from the population of cells by excluding cells that do not bind to a multimeric form of the antigen.

In some embodiments, a multimeric antigen may be further linked to a marker and/or a photosynthetic pigment including, for example, Phycoerythrin (PE), Allophycocyanin (APC), a BRILLIANT Violet fluorochrome, an ALEXA FLUOR dye, Fluorescein isothiocyanate (FITC), nanocrystals, synthetic derivatives of fluorescent dyes or molecules, etc.

In some embodiments, the methods described herein further include isolating a population of cells from the subject after immunization. The population of cells may include mononuclear cells. In some embodiments, the population of cells preferably includes a B cell. The population of cells may be isolated from, for example, the subject's blood, spleen, and/or lymph nodes. In some embodiments, the method may include making a single cell suspension that includes peripheral blood mononuclear cells (PBMCs), splenocytes, and/or a lymphocyte population.

In some embodiments, a method of making a monoclonal antibody as described herein includes enriching (e.g., selecting) a subpopulation of cells from the population of cells isolated from an immunized subject. In some embodiments, enriching the subpopulation of cells occurs prior to hybridoma formation. In some embodiments, enriching the subpopulation of cells includes increasing the proportion of a subpopulation of cells by at least 1%, at least 5%, at least 10%, at least 20% at least 30%, at least 40%, at least 50%, at least 60%, at least 70%, at least 80%, or at least 90%. In some embodiments, enriching the subpopulation of cells comprises increasing the proportion of B cells in the population that bind an antigen including, for example, the antigen (or antigens) used for immunization. In some embodiments, enrichment may provide significant time and cost saving because, for example, fewer colonies are required for screening and/or a higher percentage of selected hybridomas produce MAb against the antigen of choice (e.g., a p:MHCII).

In some embodiments, enriching the subpopulation of cells includes excluding cells that do not bind to the antigen. For example, if the antigen includes a peptide-MHC complex (p:MHC), enriching the subpopulation of cells includes excluding cells that do not bind to p:MHC. Alternatively or additionally, if the antigen includes a peptide-MHC complex (p:MHC), enriching the subpopulation of cells can include excluding cells that bind to the MHC complex not bound to the peptide or to the peptide not bound to the MHC complex. In some embodiments, excluding cells that bind to the MHC complex not bound to the peptide may include identifying cells that bind to an antigen that includes the same MHC and a different peptide. In some embodiments, excluding cells that bind to the peptide not bound to the MHC complex may include identifying cells that bind to the peptide bound to a different MHC complex and/or to unbound peptide. In some embodiments, excluding cells that do not bind to the antigen may include identifying cells that bind to a structural component of the antigen (e.g., a linker, a marker, etc.) other than the MHC and the peptide.

In embodiments where a composition including the antigen also includes an adjuvant, excluding cells that do not bind to the antigen may include excluding cells that bind to the adjuvant.

In some embodiments, enriching the subpopulation of cells includes enriching a subpopulation of cells capable of binding to a multimeric form of the antigen. A multimeric antigen may be used, for example, to confirm the expansion of a population of antigen-specific-B cells.

In some embodiments, enriching a subpopulation of cells includes increasing the proportion of B cells in the population that bind the antigen. In other words, the population of cells may include B cells specific for the antigen of interest (that is, an antigen-specific B cell), and these cells may be selected for. Enriching B cells specific for the antigen of interest prior to myeloma fusion may significantly reduce the screening required after fusion.

In some embodiments, enrichment of the subpopulation of cells may include magnetic enrichment for a B cell that binds to a multimeric antigen. In some embodiments, magnetic enrichment may include the use of a magnetic bead. In some embodiments, the magnetic bead may bind to a marker and/or a photosynthetic pigment. In some embodiments, a multimeric antigen may preferably include a p:MHC multimer.

In some embodiments, a multimeric antigen may include a marker and/or a photosynthetic pigment. In some embodiments, a B cell bound to a multimeric antigen may be enriched for using a reagent specific to the marker and/or a photosynthetic pigment including, for example, a magnetic bead. The marker and/or photosynthetic pigment may include, for example, Phycoerythrin (PE), Allophycocyanin (APC), a BRILLIANT Violet fluorochrome, an ALEXA FLUOR dye, Fluorescein isothiocyanate (FITC), nanocrystals, synthetic derivatives of fluorescent dyes or molecules, etc. For example, when a multimeric antigen includes PE, a B cell bound to the PE-multimeric antigen may be selected by using an anti-PE magnetic bead; when a multimeric antigen includes APC, a B cell bound to the APC-multimeric antigen may be selected by using an anti-APC magnetic bead.

In some embodiments, as described in an exemplary embodiment in Example 2, a multimeric antigen may include a p:MHC tetramer PE including, for example, p63:IA$^{g7}$ tetramer:PE.

In some embodiments, enrichment the subpopulation of cells may include using a non-specific antigen, that is, a different antigen than the antigen used to immunize the subject (e.g., a decoy antigen). In some embodiments, the non-specific antigen may be multimeric. For example, a non-specific antigen may be used determine if a B cell binds to a non-specific antigen.

For example, when the subject has been immunized with a peptide-MHC complex (p:MHC), the cells may be screened for binding to a second p:MHC, where the second p:MHC includes a different MHC complex or a different antigen, and cells that bind to the second p:MHC may be excluded. In some embodiments, the second p:MHC may preferably be multimeric. In some embodiments, the second p:MHC preferably includes the same MHC complex as the p:MHC of the antigen used to immunize the subject but a different peptide than the p:MHC of the antigen used to immunize the subject.

In some embodiments, enriching the subpopulation of cells using a multimeric antigen may reduce the number of cells compared to the starting population by at least 2-fold, at least 5-fold, at least 10-fold, at least 15-fold, at least 20-fold, or at least 23-fold.

In some embodiments, enriching the subpopulation of cells may include flow cytometric identification of cells. In some embodiments, identification of cells includes identification of mononuclear cells. In some embodiments, enriching the subpopulation of cells may further include sorting. For example, mononuclear cells may be identified and/or sorted by identifying expression of a lymphocyte marker (e.g., CD45) including, for example, identifying expression of a B cell marker (e.g., CD220); identifying a plasma cell marker (e.g., CD138); by testing for viability (e.g., using a GHOST DYE including, for example, GHOST DYE Violet 510; propidium iodide; 7 Amino-Actinomycin D (7AAD), etc.); and/or by testing for antigen specificity. In some embodiments, enriching the subpopulation of cells may include flow cytometric identification of undesired cell types. Enriching the subpopulation of cells may further include excluding the undesired cell types (e.g., by flow cytometric sorting). For example, in some embodiments, it may be desirable to exclude T cells (e.g., cells expressing CD90), macrophages (e.g., cells expressing F4/80), dendritic cells (e.g., cells expressing CD11c), and/or granulocytes (e.g., cells expressing GR-1) from a subpopulation of cells. In some embodiments, testing for antigen specificity may include determining if a cell is capable of binding to an antigen. In some embodiments, an antigen may include a p:MHC. In some embodiments, an antigen may include a multimeric antigen.

In some embodiments, enriching the subpopulation of cells using sorting may reduce the number of cells compared to the starting population by at least 5-fold, at least 10-fold, at least 20-fold, at least 30-fold, at least 40-fold, at least 50-fold, at least 100-fold, at least 200-fold, or at least 500-fold.

In some embodiments, enriching the subpopulation of cells using sorting may provide a population of cells that is at least 80%, at least 85%, at least 90%, at least 95%, at least 96%, at least 97%, at least 98%, or at least 99% cells identified by a marker or combination of markers. For example, the marker or combination of markers may be used to identify a B cell and/or a plasma cell.

In some embodiments, the methods described herein may be used to generate additional p:MHCII targeted MAbs. At the time of the invention, few p:MHCII targeted MAbs existed. The most well-known p:MHCII targeted MAb is the Y-Ae antibody (anti-Eα:IA$^b$), which recognizes Eα$_{52-68}$ bound to IA$^b$ MHCII molecules and was used to understand central tolerance and alloreactive antigen presentation. The efficiency of Y-Ae generation has not been described in the literature, however, the generation of MAbs specific for two different peptides of hen egg lysozyme (HEL) provides insight into the inefficiency of the process. Specifically, two HEL$_{46-61}$:IA$^k$ (clones B6G and C4H) MAb were identified by screening 500 clones (Zhong et al. *Proc Natl Acad Sci USA* 94, 13856-13861 (1997)). An additional clone specifically recognizing HEL$_{116-129}$:IA$^k$ (D8H) was identified by screening 500 different colonies. However, these clones were found to also weakly stain cells expressing IA$^k$ in an HEL-independent manner (Zhong et al. *Proc Natl Acad Sci USA* 94, 13856-13861 (1997)). In a separate report, a clone specific for HEL$_{48-62}$:IA$^k$ (Aw3.18) was generated by screening 1000 colonies (Dadaglio et al. *Immunity* 6, 727-738 (1997)). Thus, the efficiency of generating a MAb clone using conventional approaches has been reported to range from 1:250 to 1:1000 or (0.1 to 0.4%). In contrast, the methods described herein, as exemplified by Table 1, describe a range of 1:18 to 1:115 (0.9 to 13.5%). That is, the success rate of the methods described herein may be at least 2.25 to 33.75 fold higher than traditional approaches. Moreover, because fewer clones are required for positive identification, fewer hours and resources are required for hybridoma screening.

In some embodiments, a method of making a monoclonal antibody as described herein includes forming a hybridoma. In some embodiments, forming a hybridoma includes forming a hybridoma from a cell selected from the subpopulation of cells enriched as described herein. In some embodiments, the cell selected from the subpopulation of cells enriched as described herein is preferably a B cell. A hybridoma may be obtained by methods known to those skilled in the art. In some embodiments, the cell selected from the subpopulation of cells enriched as described herein is fused with another cell. In some embodiments, forming a hybridoma may include hypoxanthine-aminopterin-thymidine (HAT) selection.

In some embodiments, a method of making a monoclonal antibody as described herein includes screening a hybridoma for production of an antibody specific to an antigen of interest including, for example, and an antibody that binds the antigen used for immunization. In some embodiments, screening a hybridoma may include determining if it produces an antibody that binds a non-specific antigen and/or a decoy antigen. In some embodiments, when the antigen includes a p:MHC, a decoy antigen may include a different peptide bound to the same MHC complex as the p:MHC. A hybridoma may be screened by methods known to those skilled in the art.

Surprisingly, in contrast to traditional methods that typically yield fewer than 1% hybridomas specific for a protein target antigen, the methods described herein produce a much higher yield of hybridomas specific for a protein target. The methods provide herein are unexpectedly efficient at generating a monoclonal antibody that recognizes a peptide-MHC complex.

In some embodiments, a hybridoma may include, for example, the following hybridomas of Example 2: A1, A3, A5, B3, C5, C6, C8, F2, F7, and/or G8. In some embodiments, the hybridoma may preferably express an antibody that recognizes p63:IA$^{g7}$. In some embodiments, the hybridoma may preferably express an antibody that recognizes 2W:IA$^b$. In some embodiments, a hybridoma may include, for example, Ins 4G8 (also referred to herein as 4G8). In some embodiments, the hybridoma may preferably express an antibody that recognizes p8E: IA$^{g7}$ and/or p8G: IA$^{g7}$.

This disclosure also describes monoclonal antibodies that recognize peptide:MHCII (p:MHCII) (also referred to herein as an anti-p:MHCII MAb).

An intact antibody molecule has two heavy (H) chain variable regions (abbreviated herein as V$_H$) and two light (L) chain variable regions (abbreviated herein as V$_L$). The V$_H$ and V$_L$ regions may be further subdivided into regions of hypervariability, termed "complementarity determining regions" ("CDRs"), interspersed with regions that are more conserved, termed "framework regions" ("FRs"). The extent of the FRs and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al., *J. Mol. Biol.* 1987; 196: 901-917). Each V$_H$ and V$_L$ is composed of three CDRs and four FRs, arranged from amino-terminus to carboxy-terminus in the following order: FR1, CDR1, FR2, CDR2, FR3, CDR3, FR4.

In some embodiments, an anti-p:MHCII MAb may include, for example, antibody FS1. In some embodiments, FS1 may be produced by hybridoma A1. In some embodiments, a monoclonal antibody includes a monoclonal antibody having the same heavy chain as FS1. In some embodiments, a monoclonal antibody includes a monoclonal antibody having the same light chain as FS1. In some embodiments, a monoclonal antibody may contain one, two, three, four, five, six, or more amino acid substitutions in the heavy and/or the light chains of FS1 wherein the amino acid substitutions do not substantially affect binding of the antibody to p63:IA$^{g7}$. In some embodiments, a monoclonal antibody includes a monoclonal antibody having the same V$_H$ domain as FS1. In some embodiments, a monoclonal antibody includes a monoclonal antibody having the same V$_L$ domain as FS1. In some embodiments, a monoclonal antibody includes a monoclonal antibody having the same V$_H$ domain and the same V$_L$ domain as FS1. In some embodiments, a monoclonal antibody can contain one, two, three, four, five, six, or more amino acid substitutions in the V$_H$ domains and/or the V$_L$ domains identified above which do not substantially affect binding of the antibody to p63:IA$^{g7}$. In some embodiments, a monoclonal antibody includes a monoclonal antibody having at least one CDR region of the V$_H$ domain of FS1, at least two CDR regions of the V$_H$ domain of FS1, or at least three CDR regions of the V$_H$ domain of FS1. Additionally or alternatively, in some embodiments, a monoclonal antibody includes a monoclonal antibody having at least one CDR region of the V$_L$ domain of FS1, at least two CDR regions of the V$_L$ domain of FS1, or at least three CDR regions of the V$_L$ domain of FS1. In some embodiments, a monoclonal antibody may contain one, two, three, four, five, six, or more amino acid substitutions in one or more CDR regions identified above which do not substantially affect binding of the antibody to p63:IA$^{g7}$.

In some embodiments, an anti-p:MHCII MAb may include, for example, antibody W6. In some embodiments, W6 may be produced by hybridoma A1. In some embodiments, a monoclonal antibody includes a monoclonal antibody having the same heavy chain as W6. In some embodiments, a monoclonal antibody includes a monoclonal antibody having the same light chain as W6. In some embodiments, a monoclonal antibody may contain one, two, three, four, five, six, or more amino acid substitutions in the heavy and/or the light chains of W6 wherein the amino acid substitutions do not substantially affect binding of the antibody to 2W:IA$^b$. In some embodiments, a monoclonal antibody includes a monoclonal antibody having the same $V_H$ domain as W6. In some embodiments, a monoclonal antibody includes a monoclonal antibody having the same $V_L$ domain as W6. In some embodiments, a monoclonal antibody includes a monoclonal antibody having the same $V_H$ domain and the same $V_L$ domain as W6. In some embodiments, a monoclonal antibody can contain one, two, three, four, five, six, or more amino acid substitutions in the $V_H$ domains and/or the $V_L$ domains identified above which do not substantially affect binding of the antibody to 2W:IA$^b$. In some embodiments, a monoclonal antibody includes a monoclonal antibody having at least one CDR region of the $V_H$ domain of W6, at least two CDR regions of the $V_H$ domain of W6, or at least three CDR regions of the $V_H$ domain of W6. Additionally or alternatively, in some embodiments, a monoclonal antibody includes a monoclonal antibody having at least one CDR region of the $V_L$ domain of W6, at least two CDR regions of the $V_L$ domain of W6, or at least three CDR regions of the $V_L$ domain of W6. In some embodiments, a monoclonal antibody may contain one, two, three, four, five, six, or more amino acid substitutions in one or more CDR regions identified above which do not substantially affect binding of the antibody to 2W:IA$^b$.

In some embodiments, an anti-p:MHCII MAb may include, for example, antibody XRI1. In some embodiments, XRI1 may be produced by hybridoma Ins 4G8 (also referred to herein as 4G8). In some embodiments, a monoclonal antibody includes a monoclonal antibody having the same heavy chain as XRI1. In some embodiments, a monoclonal antibody includes a monoclonal antibody having the same light chain as XRI1. In some embodiments, a monoclonal antibody may contain one, two, three, four, five, six, or more amino acid substitutions in the heavy and/or the light chains of XRI1 wherein the amino acid substitutions do not substantially affect binding of the antibody to p8E:IA$^{g7}$ and/or p8G:IA$^{g7}$. In some embodiments, a monoclonal antibody includes a monoclonal antibody having the same $V_H$ domain as XRI1. In some embodiments, a monoclonal antibody includes a monoclonal antibody having the same $V_L$ domain as XRI1. In some embodiments, a monoclonal antibody includes a monoclonal antibody having the same $V_H$ domain and the same $V_L$ domain as XRI1. In some embodiments, a monoclonal antibody can contain one, two, three, four, five, six, or more amino acid substitutions in the $V_H$ domains and/or the $V_L$ domains identified above which do not substantially affect binding of the antibody to p8E:IA$^{g7}$ and/or p8G:IA$^{g7}$. In some embodiments, a monoclonal antibody includes a monoclonal antibody having at least one CDR region of the $V_H$ domain of XRI1, at least two CDR regions of the $V_H$ domain of XRI1, or at least three CDR regions of the $V_H$ domain of XRI1. Additionally or alternatively, in some embodiments, a monoclonal antibody includes a monoclonal antibody having at least one CDR region of the $V_L$ domain of XRI1, at least two CDR regions of the $V_L$ domain of XRI$_1$, or at least three CDR regions of the $V_L$ domain of XRI1. In some embodiments, a monoclonal antibody may contain one, two, three, four, five, six, or more amino acid substitutions in one or more CDR regions identified above which do not substantially affect binding of the antibody to p8E:IA$^{g7}$ and/or p8G:IA$^{g7}$.

In some embodiments, a monoclonal antibody can contain one, two, three, four, five, six, or more amino acid substitutions in one or more framework regions (FRs). In some embodiments, the substitutions or substitutions in the framework regions (FRs) do not substantially affect binding of the antibody to PE.

This disclosure also describes monoclonal antibodies that recognize phycoerythrin (PE).

Figure 14:
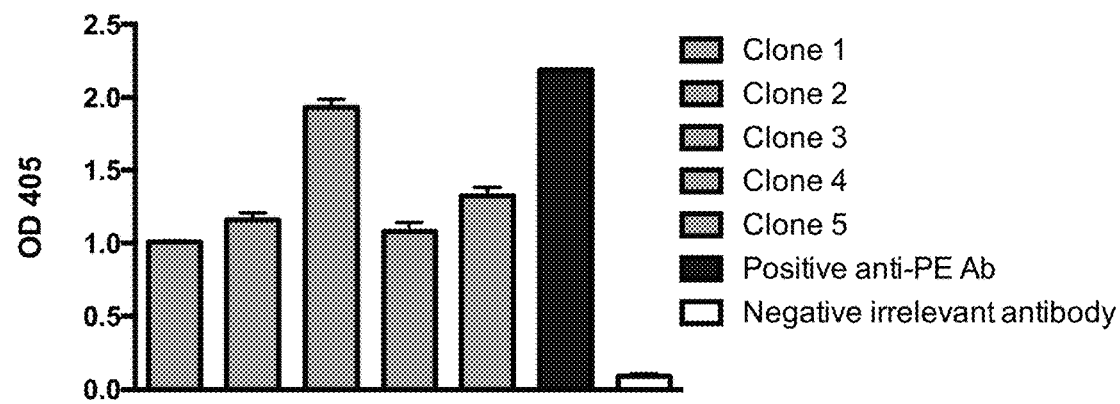
FIG. 14 shows indirect ELISA screening of hybridoma supernatants as described in Example 3.

In some embodiments, an antibody that recognizes PE is produced by a clone described in Example 3 and FIG. 14. In some embodiments, an antibody that recognizes PE includes an antibody of FIG. 23. In some embodiments, an antibody that recognizes PE includes a monoclonal antibody having the same heavy chain as a heavy chain of FIG. 23. In some embodiments, an antibody that recognizes PE includes a monoclonal antibody having the same light chain as a light chain of FIG. 23. In some embodiments, a monoclonal antibody may contain one, two, three, four, five, six, or more amino acid substitutions in the heavy and/or the light chains of an antibody of FIG. 23 wherein the amino acid substitutions do not substantially affect binding of the antibody to PE. In some embodiments, a monoclonal antibody includes a monoclonal antibody having the same $V_H$ domain as a $V_H$ domain of FIG. 23. In some embodiments, a monoclonal antibody includes a monoclonal antibody having the same $V_L$ domain as a $V_L$ domain of FIG. 23. In some embodiments, a monoclonal antibody includes a monoclonal antibody having the same $V_H$ domain and $V_L$ domain as a $V_H$ domain and $V_L$ domain of FIG. 23. In some embodiments, a monoclonal antibody can contain one, two, three, four, five, six, or more amino acid substitutions in the $V_H$ domains and/or the $V_L$ domains identified above which do not substantially affect binding of the antibody to PE.

In some embodiments, an antibody that recognizes PE includes a monoclonal antibody having at least one CDR, at least two CDRs, or at least three CDRs of a $V_H$ domain of FIG. 23. In some embodiments, an antibody that recognizes PE includes a monoclonal antibody having at least one CDR, at least two CDRs, or at least three CDRs of a $V_L$ domain of FIG. 23. In some embodiments, a monoclonal antibody can contain one, two, three, four, five, six, or more amino acid substitutions in one or more CDRs identified above which do not substantially affect binding of the antibody to PE.

In some embodiments, any of the monoclonal antibodies described herein can contain one, two, three, four, five, six, or more amino acid substitutions in one or more framework regions (FRs). In some embodiments, the substitutions or substitutions in the framework regions (FRs) do not substantially affect binding of the antibody to the corresponding antigen.

In another aspect, this disclosure describes an isolated polynucleotide molecule. In some embodiments, the isolated polynucleotide molecule includes a nucleotide sequence encoding a monoclonal antibody. In some embodiments, the isolated polynucleotide molecule includes a nucleotide sequence that has at least 75%, at least 80%, at least 85%, at least 90%, at least 95%, at least 96%, at least 97%, at least 98%, or at least 99% sequence identity to a nucleotide sequence encoding a monoclonal antibody described herein or a portion of a monoclonal antibody described herein.

The antibody may be an antibody from any suitable species. In some embodiments, the antibody may be a mouse antibody. In some embodiments, the antibody may be a rat antibody. In some embodiments, the antibody may be a rabbit antibody.

In some embodiments, the antibodies described herein (including antibodies produced by the methods described herein) may be humanized. An antibody can be humanized by any suitable method. Techniques for producing humanized monoclonal antibodies can be found, for example, in Jones et al., *Nature* (1986) 321:522 and Singer et al., *J. Immunol.*, (1993) 150:2844. For example, humanization of the antibody can include changes to the antibody to reduce the immunogenicity of the antibody when used in humans. In some embodiments, a humanized antibody can include at least a portion of an immunoglobulin constant region (Fc) of a human immunoglobulin. A humanized antibody can include, in some embodiments, a human immunoglobulin (recipient antibody) in which residues from one or more complementary determining regions (CDRs) of the recipient antibody are replaced by residues from one or more CDRs of a non-human species antibody (donor antibody), such as mouse, rat, or rabbit antibody. In some embodiments, Fv framework residues of a human immunoglobulin can be replaced by corresponding non-human residues.

In some embodiments, the antibody is an IgG antibody. In some embodiments, the antibody may be an antibody or an IgG subclass including, for example, IgG1, IgG2, IgG3 or IgG4. In some embodiments, the antibody may be a mouse IgG of one of the following sub-classes: IgG1, IgG2A, IgG2B, IgG2C and IgG3. In some embodiments, the antibody may be a rat IgG of one of the following sub-classes: IgG1, IgG2A, IgG2B, or IgG2C.

In some embodiments, the antibody may include a kappa light chain. In some embodiments, the antibody may include a lambda light chain.

In some embodiments, the monoclonal antibody includes an antigen-binding fragment including an Fab fragment, an Fab' fragment, an $F(ab)_2$ fragment, and/or an Fv fragment.

The antibodies described herein (including antibodies produced by the methods described herein) and compositions including the antibodies described herein may be used for any suitable use.

For example, in some embodiments, the antibodies may be used to block antigen presentation to T or B cells during bacterial or viral pathogenesis and/or to provide mechanistic insight for immunity and regulation.

In some embodiments, the antibodies including, for example, an MAb specific for p:MHC, may be used to study specific subsets of antigen presenting cells during immune recognition (e.g., from immune homeostasis to defining novel roles for multiple subsets of antigen presenting cells responding to vaccination and infection).

In some embodiments, the antibodies can be used to treat a disorder including, for example, an autoimmune-related disorder. In some embodiments, the disorder could include diabetes. For example, in some embodiments, the antibodies described herein including, for example, XRI1, a humanized version of XRI1, or an antibody including a component of XRI1 (e.g., a heavy chain, a light chain, a $V_H$ domain, a $V_L$ domain and/or a CDR of XRI1) could be used in an antigen-specific therapeutic approach to treat diabetes.

In some embodiments, this disclosure describes a composition including at least one of the antibodies describes herein.

In some embodiments, the composition may also include, for example, buffering agents to help to maintain the pH in an acceptable range or preservatives to retard microbial growth. A composition may also include, for example, carriers, excipients, stabilizers, chelators, salts, or antimicrobial agents. Acceptable carriers, excipients, stabilizers, chelators, salts, preservatives, buffering agents, or antimicrobial agents, include, but are not limited to, buffers such as phosphate, citrate, and other organic acids; antioxidants including ascorbic acid and methionine; preservatives, such as sodium azide, octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; polypeptides; proteins, such as serum albumin, gelatin, or non-specific immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zinc (Zn)-protein complexes); and/or non-ionic surfactants such as TWEEN, PLURONICS, or polyethylene glycol (PEG).

In some embodiments, the composition is a pharmaceutical composition and includes the monoclonal antibody and a pharmaceutically acceptable carrier, diluent or excipient. In the preparation of the pharmaceutical compositions comprising the antibodies described in the teachings herein, a variety of vehicles and excipients may be used, as will be apparent to the skilled artisan.

The pharmaceutical compositions will generally comprise a pharmaceutically acceptable carrier and a pharmacologically effective amount of an antibody, or mixture of antibodies.

The pharmaceutical composition may be formulated as a powder, a granule, a solution, a suspension, an aerosol, a solid, a pill, a tablet, a capsule, a gel, a topical cream, a suppository, a transdermal patch, and/or another formulation known in the art.

For the purposes described herein, pharmaceutically acceptable salts of an antibody are intended to include any art-recognized pharmaceutically acceptable salts including organic and inorganic acids and/or bases. Examples of salts include but are not limited to sodium, potassium, lithium, ammonium, calcium, as well as primary, secondary, and tertiary amines, esters of lower hydrocarbons, such as methyl, ethyl, and propyl. Other salts include but are not limited to organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. For example, the antibody may be prepared as a formulation in a pharmaceutically acceptable diluent, including for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as a solid formulation in an appropriate excipient.

A pharmaceutical composition will often further comprise one or more buffers (e.g., neutral buffered saline or phosphate buffered saline), carbohydrates (e.g., glucose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, adjuvants (e.g., aluminium hydroxide), solutes that render the formulation isotonic, hypotonic or weakly hypertonic with the blood of a recipient, suspending agents, thickening agents and/or preservatives. Alternatively, compositions of the present invention may be formulated as a lyophilizates.

Any suitable carrier known to those of ordinary skill in the art may be employed in a composition including at least one of the antibodies describes herein. Antibody compositions may be formulated for any appropriate manner of administration, including for example, oral, nasal, mucosal, intravenous, intraperitoneal, intradermal, subcutaneous, and intramuscular administration.

A compositions of the present disclosure may be formulated in a pharmaceutical preparation in a variety of forms adapted to the chosen route of administration. One of skill will understand that the composition will vary depending on mode of administration and dosage unit. For example, for parenteral administration, isotonic saline can be used. For topical administration a cream, including a carrier such as dimethylsulfoxide (DMSO), or other agents typically found in topical creams that do not block or inhibit activity of the peptide, can be used. Other suitable carriers include, but are not limited to alcohol, phosphate buffered saline, and other balanced salt solutions. The compounds of this invention can be administered in a variety of ways, including, but not limited to, intravenous, topical, oral, subcutaneous, intraperitoneal, and intramuscular delivery. In some aspects, the compounds of the present invention may be formulated for controlled or sustained release. In some aspects, a formulation for controlled or sustained release is suitable for subcutaneous implantation. In some aspects, a formulation for controlled or sustained release includes a patch. A compound may be formulated for enteral administration, for example, formulated as a capsule or tablet.

Administration may be as a single dose or in multiple doses. In some embodiments, the dose is an effective amount as determined by the standard methods, including, but not limited to, those described herein. Those skilled in the art of clinical trials will be able to optimize dosages of particular compounds through standard studies. Additionally, proper dosages of the compositions can be determined without undue experimentation using standard dose-response protocols. Administration includes, but is not limited to, any of the dosages and dosing schedules, dosing intervals, and/or dosing patterns described in the examples included herewith.

The composition including an antibody according to the present disclosure can be administered by any suitable means including, but not limited to, for example, oral, rectal, nasal, topical (including transdermal, aerosol, buccal and/or sublingual), vaginal, parenteral (including subcutaneous, intramuscular, and/or intravenous), intradermal, intravesical, intra-joint, intra-arteriole, intraventricular, intracranial, intraperitoneal, intranasal, by inhalation, or intralesional (for example, by injection into or around a tumor).

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparation may be pyrogen-free.

Many suitable formulations are known, including polymeric or protein microparticles encapsulating drug to be released, ointments, gels, or solutions which can be used topically or locally to administer drug, and even patches, which provide controlled release over a prolonged period of time. These can also take the form of implants. Such an implant may be implanted within the tumor.

The compounds of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

As used herein "treating" or "treatment" can include therapeutic and/or prophylactic treatments. "Treating a disorder," as used herein, is not intended to be an absolute term. Treatment may lead to an improved prognosis or a reduction in the frequency or severity of symptoms. A "therapeutically effective" concentration or amount as used herein is an amount that provides some improvement or benefit to the subject. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. Likewise, the term "preventing," as used herein, is not intended as an absolute term. Instead, prevention refers to delay of onset, reduced frequency of symptoms, or reduced severity of symptoms associated with a disorder. Prevention therefore refers to a broad range of prophylactic measures that will be understood by those in the art. In some circumstances, the frequency and severity of symptoms is reduced to non-pathological levels. In some circumstances, the symptoms of an individual receiving the compositions of the invention are only 90%, 80%, 70%, 60%, 50%, 40%, 30%, 20%, 10%, 5%, or 1% as frequent or severe as symptoms experienced by an untreated individual with the disorder.

Therapeutically effective concentrations and amounts may be determined for each application herein empirically by testing the compounds in known in vitro and in vivo systems, such as those described herein, dosages for humans or other animals may then be extrapolated therefrom.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods. Toxicity and therapeutic efficacy of the compositions can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compositions that exhibit high therapeutic indices can be preferred. The data obtained from cell culture assays and animal studies can be used in formulating a range of dosage for use in humans. The dosage of such compositions can preferably lie within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition.

A composition as described herein may be administered at once, or may be divided into a number of smaller doses to be administered at intervals of time. For example, compositions may be administered repeatedly, e.g., at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% compared to the expected reduction in the parameter in an individual not treated with the agent.

In some aspects of the methods of the present disclosure, a method further includes the administration of one or more additional therapeutic agents. One or more additional therapeutic agents may be administered before, after, and/or coincident to the administration of a monoclonal antibody as described herein. An additional therapeutic agent can include, for example, chemotherapy, radiation therapy, etc. Additional therapeutic agents may be administered separately or as part of a mixture or cocktail. In some aspects of the present disclosure, the administration of an antibody may allow for the effectiveness of a lower dosage of other therapeutic modalities when compared to the administration of the other therapeutic modalities alone, providing relief from the toxicity observed with the administration of higher doses of the other modalities.

In some aspects of the methods of the present disclosure, the administration a composition as described herein and the at least one additional therapeutic agent demonstrate therapeutic synergy. In some aspects of the methods of the present disclosure, a measurement of response to treatment observed after administering both an antibody as described herein and the additional therapeutic agent is improved over the same measurement of response to treatment observed after administering either the antibody or the additional therapeutic agent alone.

As used herein, the term "subject" includes, but is not limited to, humans and non-human vertebrates. In some embodiments, a subject is a mammal, particularly a human. A subject may be an individual. A subject may be an "individual," "patient," or "host." Non-human vertebrates include livestock animals, companion animals, and laboratory animals. A non-human subject also may include a non-human primate as well as a rodent, such as, but not limited to, a rat or a mouse. A non-human subject also may include, without limitation, a chicken, a horse, a cow, a pig, a goat, a dog, a cat, a guinea pig, a hamster, a mink, a rabbit, etc.

The present invention is illustrated by the following examples. It is to be understood that the particular examples, materials, amounts, and procedures are to be interpreted broadly in accordance with the scope and spirit of the invention as set forth herein.

EXAMPLES

Example 1

BDC2.5 CD4+ T cells are used in mouse models of Type 1 Diabetes (T1D), as the transfer of activated cells results in rapid diabetes pathogenesis. Chromogranin A has been shown to be the natural ligand of BDC2.5 CD4+ T cells as well as an autoantigen in human studies of T1D. However, the exact role of this autoantigen is unknown due to lack of reagents. Two peptide mimotopes, p31 and p63, share a common amino acid motif with a natural cleavage product of Chromogranin A, WE14. This Example describes the generation of a broadly cross reactive antibody against two BDC2.5 T cell mimotopes by priming and boosting with the two distinct monomers.

BDC2.5 T cells recognize WE14, a cleavage product of Chromogranin A, which shares a common five amino acid motif with two T cell activating mimotopes, peptide 31 (p31) and p63 (FIG. 1). (Stadinski et al. *Nat Immunol.* 11(3):225-31 (2010); Marrack et al. *Cold Spring Hard Perspect Med.* 2(9):a007765 (2012).)

Figure 4:
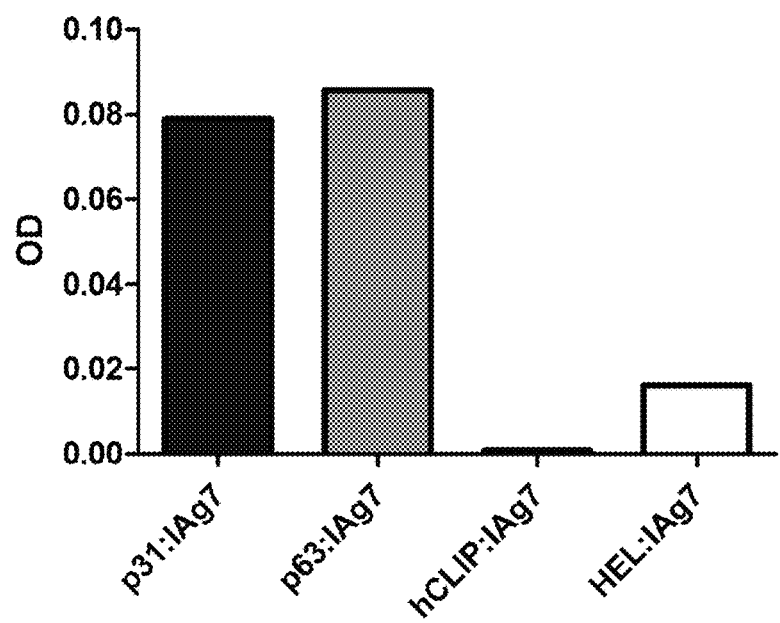
FIG. 4 shows a representative cross-reactive ELISA result showing that an antibody produced according to the methods of Example 1 was cross-reactive to p31:IA$^{g7}$ and p63:IA$^{g7}$.
Figure 5:
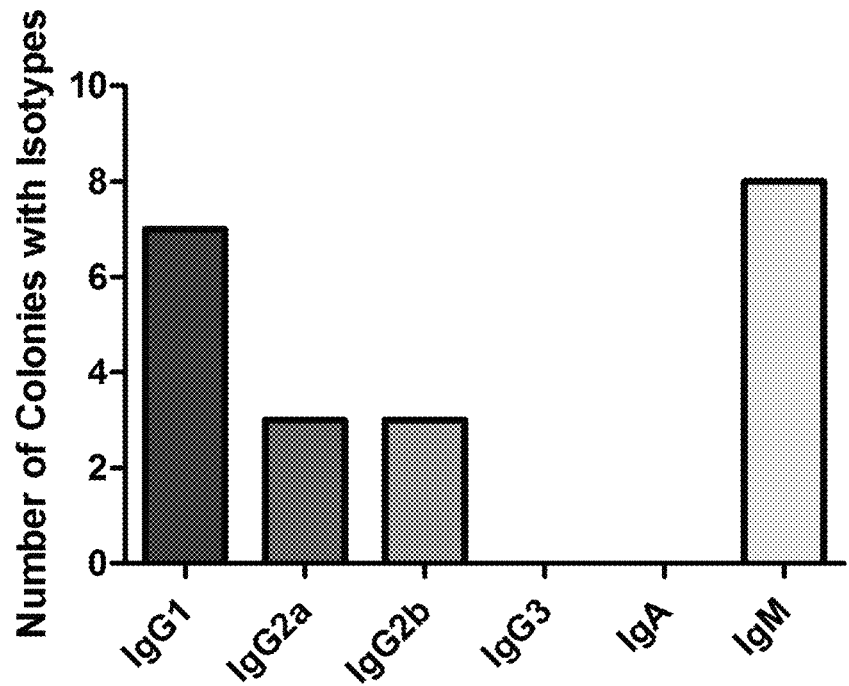
FIG. 5 shows an isotype analysis of antibodies produced according to the methods of Example 1.
Figure 6:
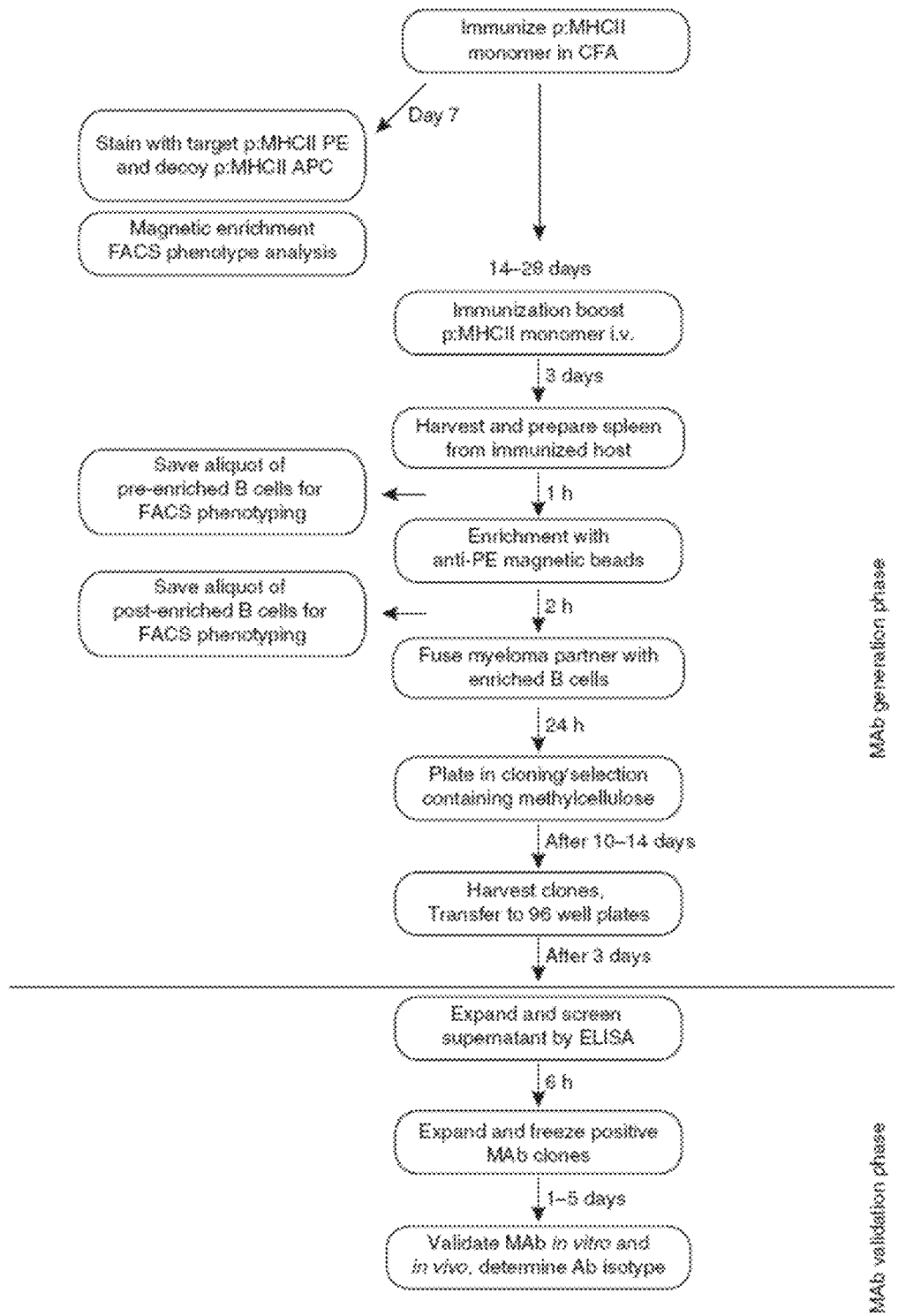
FIG. 6 shows an exemplary scheme for the generation and validation of p:MHCII MAb. As further described in Example 2, mice were immunized with p:MHCII emulsified in complete Freund's adjuvant (CFA). To validate successful priming and expansion, the phenotype of p:MHCII-specific B cells in naïve mice was compared to the phenotype on day 7 post immunization. After 7 days, splenocytes from naïve and immunized mice were collected and stained for specific immunogen p:MHCII-PE and decoy p:MHCII APC, streptavidin-PE-AF647, streptavidin-APC-DYLIGHT 755, magnetically enriched using anti-PE and anti-APC magnetic beads and analyzed by flow cytometry (Taylor et al. *J. Exp. Med.* 209:2065-2077 (2012)). p:MHCII-specific B cells were gated from streptavidin, APC and PE binding cells (Taylor et al. *J. Exp. Med.* 209:2065-2077 (2012). Germinal center B cells (GL7$^+$ and Intracellular Ig$^-$) and plasma cells (GL7$^-$ and intracellular Ig$^+$) were then identified from the various B-cell populations binding these distinct tetramer reagents to demonstrate successful priming. After 28 days, mice were boosted with a second immunization of p63:IA$^{g7}$ monomeric protein intravenously. Three days following the immune boost, magnetic B-cell enrichment for splenic B cells binding to the p63:IA$^{g7}$ tetramer:PE reagent were performed. Enriched cells were fused with myeloma fusion partners, expanded and screened for in vitro and in vivo validation.

Mice were immunized according to the immunization scheme shown in FIG. 2. Antibody-expressing cells were isolated according to the scheme shown in FIG. 3. 480 hybridomas were generated by fusion of antibody-expressing cells with parental myeloma cells, and antibodies were harvested and screened for reactivity with monomers using ELISA. 14 clones were found to be reactive to p31:IA$^{g7}$ but not an hCLIP:IA$^{g7}$. 12 of the 14 clones were cross-reactive to p31:IA$^{g7}$ and p63:IA$^{g7}$. A representative cross-reactive ELISA result is shown in FIG. 4. As shown in FIG. 5, a high proportion of detected antibodies were IgM but a diverse array of IgG subtypes were also obtained.

Example 2

This Example describes a methodology that may be used to generate a monoclonal antibody (MAb) including, for example, a MAb against a specific peptide MHCII complex.
Methods
Mice, Female NOD mice (6-8 weeks of age) were purchased from Taconic Biosciences (Hudson, N.Y.). Female C57BL/6 (6-8 weeks of age), female 129 (6-8 weeks of age), and female BALB/c mice (8-10 weeks of age) were purchased from the Jackson Laboratory (Bar Harbor, Me.).

Female (6 week old) NOD.BDC2.5 Thy1.1 transgenic mice were bred under specific pathogen-free, barrier facility at the University of Minnesota. Animals were housed under specific pathogen-free, barrier facility in accordance with NIH guidelines. All animal procedures were approved by the University of Minnesota or Tulane Institutional Animal Care and Use Committee.

Peptides. Peptides used for in vivo immunization and in vitro stimulation and peptide pulsing include p63 (RTR-PLWVRME) (SEQ ID NO:5), p31 (YVRPLWVRME) (SEQ ID NO:6), $OVA_{141-160}$ (CARELINSWVESQTNGIIRN) (SEQ ID NO:7) (Genemed Synthesis, San Antonio, Tex.), 2W (EAWGALANWAVDSA) (SEQ ID NO:8) (Genscript, Piscataway, N.J.).

Peptide:MHCII monomers and tetramers. p63:$IA^{g7}$ (RTR-PLWVRME) (SEQ ID NO:5), $InsB_{10-23}$:$IA^{g7}$ (HLVERLYL-VCGEEG) (SEQ ID NO:9), 2W:$IA^b$ (EAWGALANWAV-DSA) (SEQ ID NO:8) and LLO:$IA^b$ (NEKYAQAYPNVS) (SEQ ID NO:10) was either from the NIH tetramer core facility (Emory University, Atlanta, Ga.) or produced using S2 insect cell expression system (Moon et al. Nat Protoc 4:565-581 (2009); Moon et al. Immunity 27:203-213 (2007) Pauken et al. J Immunol 191:4913-4917 (2013)). Briefly, peptide:$IA^{g7}$ or peptide:$IA^b$ molecules were expressed in Drosophila S2 cells using the DES Drosophila Expression System kit (Invitrogen, Carlsbad, Calif.). The S2 cells were cotransfected using calcium phosphate, with plasmids encoding the alpha chain, the peptide-linked beta chain, BirA ligase and a blasticidin resistance gene at a molar ratio of 9:9:9:1 for $IA^b$ and $IA^{g7}$. Transfected cells were selected in blasticidin-containing Schneider's Drosophila Medium (Invitrogen, Carlsbad, Calif.) with 10% fetal bovine serum, 100 Units per milliliter (U/mL) penicillin/streptomycin (Gibco, ThermoFisher Scientific, Waltham, Mass.), and 20 micrograms per milliliter (g/mL) gentamycin (Invitrogen, Carlsbad, Calif.) for 1 week at 28° C., passaged into serum-free media containing 25 µg/mL blasticidin (Invitrogen, Carlsbad, Calif.), and scaled to 0.5 liter (L) cultures in 2 L shaker flasks maintained at 150 rotations per minute (rpm). When cell densities reached $5\times10^6$/mL, monomer expression was induced by the addition of 0.8 millimolar (mM) copper sulfate. Peptide:$IA^b$ or $IA^{g7}$ heterodimers were purified from supernatants 8 days later by immobilized metal ion affinity chromatography using a His-Bind purification kit (EMD Millipore, Billerica, Mass.) and eluted using 1 molar (M) imidazole. The biotinylated pMHCII heterodimers in the eluate were then affinity purified using Monomeric Avidin UltraLink (Pierce, ThermoFisher Scientific, Waltham, Mass.). Bound peptide:$IA^b$ or $IA^{g7}$ molecules were eluted with 2 mM biotin in phosphate buffered saline (PBS) and excess free biotin was removed by centrifugation and 4 washes with 12 milliliters (mL) PBS using a 30KD cut-off AMICON Ultra-15 filter (EMD Millipore, Billerica, Mass.). Tetramers were produced by incubating pMHCII monomers with streptavidin-APC (#PJ27S, Prozyme, Inc., Hayward, Calif.) or streptavidin-PE (#PJRS27, Prozyme, Inc., Hayward, Calif.) at a 4:1 molar ratio. For the detection of streptavidin (SA) and fluorochrome specific B cells, ALEXA FLUOR 647 (AF647) was conjugated to SA-PE (Prozyme, Inc., Hayward, Calif.) for 60 minutes at room temperature using an antibody labeling kit (ThermoFisher Scientific, Waltham, Mass.) and free AF647 was removed by centrifugation in a 30 kilodalton (KD) molecular weight cut off filter. The concentration was then adjusted to 1 µM PE based on the absorbance at 565 nanometers (nm) using a nandrop spectrophotometer (ThermoFisher Scientific, Waltham, Mass.). Similarly, SA-APC (Prozyme, Inc., Hayward, Calif.) was conjugated to DYLIGHT 755 using an antibody labeling kit (ThermoFisher Scientific, Waltham, Mass.) and the concentration was adjusted to 1 µM APC based on the absorbance at 650 nm.

Antigen specific B cell enrichment and phenotyping. BALB/c mice were immunized with 50 micrograms (µg) total of pMHCII emulsified in complete Freund's adjuvant (CFA, Sigma-Aldrich, St. Louis, Mo.) subcutaneously in the flank and in the base of the tail. Seven days post immunization single-cell suspensions from spleen and pooled lymph nodes (inguinal, brachial, cervical, and axillary) were prepared by forcing the tissue through a 100 micrometer (µm) cell strainer using the plunger end of a 1 mL syringe, washed with RPMI containing 2% fetal bovine serum, and resuspended in 100 microliter (µL) Fc block (2.4G2, 0.05% sodium azide). The cells were next incubated with 5 nanomolar (nM) SA-PE-AF647, and SA-APC-DYLIGHT 755 for 10 minutes at 25° C., followed by peptide:MHCII conjugated PE and APC tetramers at 10 nM for 25 minutes on ice in a final staining volume of 200 µL. The cells were then washed with 12 milliliters (mL) PBS+2% fetal bovine serum, resuspended in 150 mL of PBS+2% fetal bovine serum, mixed with 25 µL anti-PE and anti-APC MicroBeads (Miltenyi Biotec, Bergisch Gladbach, Germany) and incubated for 25 minutes at 4 degrees Celsius (° C.). The cells were then washed with 12 mL PBS+2% Fetal Bovine Serum (FBS), resuspended in 3 mL PBS+2% FBS and applied to a magnetized LS column (Miltenyi Biotec, Bergisch Gladbach, Germany). The column was washed 3 times with 3 mL PBS+2% FBS, removed from the magnet, and the cells were eluted in 5 mL PBS+2% FBS. All the eluted cells and $\frac{1}{20}^{th}$ of the flowthrough were then centrifuged and stained with surface antibodies IgM-PerCp-Cy5.5 (11/41, eBioscience, ThermoFisher Scientific, Waltham, Mass.), B220-PE-Cy7 (RA3-6B2, Tonbo Biosciences, San Diego, Calif.), CD38-AF700 (90, eBioscience, ThermoFisher Scientific, Waltham, Mass.), GL7-FITC (GL7, eBioscience, ThermoFisher Scientific, Waltham, Mass.), IgD-BV786 (11-26c.2a, BD Biosciences, Franklin Lakes, N.J.), CD11b-BV510 (M1/70, BD Biosciences, Franklin Lakes, N.J.), CD11c-BV510 (N418, BioLegend, San Diego, Calif.), F4/80-BV510 (BM8, BioLegend, San Diego, Calif.), CD90.2-BV510 (53-2.1, Biolegend, San Diego, Calif.), Live/Dead Ghost 510 dye (Tonbo Biosciences, San Diego, Calif.) for 30 minutes at 4° C. Next, the cells were fixed with CYTOFIX/CYTOPERM solution (BD Biosciences, Franklin Lakes, N.J.) for 20 minutes at 4° C., washed twice with permeabilization buffer, and stained with intracellular antibodies IgG (H+L)-AF350 (polyclonal, ThermoFisher Scientific, Waltham, Mass.) for 30 minutes at 4° C. in permeabilization buffer prior to flow cytometry analysis on a LSRII Fortessa instrument (Becton Dickinson, Franklin Lakes, N.J.) equipped with 5 laser lines (355 nm, 405 nm, 488 nm, 561 nm, and 640 nm). All antibodies were used at a 1:100 dilution for staining, except CD90.2 which was diluted 1:500. The data were analyzed using FlowJo software (v.10) (FlowJo, LLC, Ashland, Oreg.).

Isolation and fusion of antibody producing B cells. BALB/c mice were immunized subcutaneously in the flank and in the base of the tail with 50 micrograms (µg) of p:MHCII monomer emulsified in complete Freunds' adjuvant. Twenty eight days later each mouse was boosted by intravenous injection of 100 µL total volume containing 25 µg of p:MHCII in PBS. Three days after boost, mice were euthanized and a single cells suspension was made from pooled spleens and draining lymph nodes. Cells were stained in 150 µL of complete media (DMEM, 10% Fetal Calf Serum (FCS), β-ME, pen/strep, nonessential amino acids) containing 13.3 nM PE-conjugated p:MHCII/mouse and incubated on ice for 25 minutes. Cells were washed with complete media and resuspended in 200 µL of complete media containing 50 µL of anti-PE microbeads (Miltenyi Biotec, Bergisch Gladbach, Germany)/mouse and incubated on ice for 25 minutes. Cells were washed with complete media and resuspended in 5 mL of complete media/spleen. The cell suspension was then applied to a pre-equilibrated LS magnetic column (Miltenyi Biotec, Bergisch Gladbach, Germany) and washed 2 times with 3 mL of complete media. The cells were eluted from the column in 5 mL Medium A (StemCell Technologies, Vancouver, Canada), centrifuged, and enumerated. The enriched B cells were fused with SP2/0 mouse myeloma cells using the HY Hybridoma Cloning Kit according the manufacturer's protocol using Method A (StemCell Technologies, Vancouver, Canada). A small portion of the enriched cells and flow through was stained as described above to determine antigen specific B cell purity and phenotype prior to hybridoma fusion.

Hybridoma selection and specificity screening. Twelve days post-hypoxanthine-aminopterin-thymidine (HAT) selection, individual colonies were handpicked and transferred to 96-well plates containing Medium E (StemCell Technologies, Vancouver, Canada). Four days later hybridoma supernatants were transferred to 96-well plates and fresh medium E was added to the cells. To test the specificity of hybridoma supernatants for MHCII and p:MHCII, a decoy screening approach was employed. ELISA plates were coated with 50 nanograms (ng)/well either p63:IA$^{g7}$ or InsB$_{10\text{-}23}$:IA$^{g7}$ (for p63:IA$^{g7}$ antibodies), or 2W:IA$^b$ or LLO:IA$^b$, and then blocked with 1% BSA in PBS for 1 hour. Hybridoma supernatants were mixed 1:1 with ELISA wash buffer (PBS+0.05% Tween20) and added to the p:MHCII coated plates and incubated at 37° C. for 2 hours. Media alone was used as a negative control while anti-IA$^{g7}$ (clone 10-2.16[28], Bio X Cell, West Lebanon, N.H.) or anti-IA$^b$ (Y3P[29], ATCC, Manassas, Va.) were used as a positive control. For antibody detection the wells were incubated with HRP conjugated goat anti-mouse IgG (BioLegend, San Diego, Calif.) diluted to 1:2000 at room temperature for 2 hours followed by addition of ABTS substrate solution (KPL, SeraCare Life Sciences, Milford, Mass.) and detection by absorbance at 405 nm. Antibodies reacting to both p:MHCII monomers were considered specific for MHCII independent of peptide, while antibodies reacting with only p63:IA$^{g7}$ or 2W:IA$^b$ were considered p:MHCII specific.

Antibody affinity measurements and sequencing. The affinity of the two novel MAb generated (FS1 and W6) were directly compared with known IA$^{g7}$ or IA$^b$ specific antibodies (10-2.16[28] (Bio X Cell, West Lebanon, N.H.), Y3P[29] (ATCC, Manassas, Va.), Y-Ae[3] (eBioscience, ThermoFisher Scientific, Waltham, Mass.), and AF6-120.1[30] (Biolegend, San Diego, Calif.)) by Bio-Layer Interferometry by Precision Antibody (Columbia, Md.). Antibody sequences were obtained using the SMARTer RACE cDNA Amplification Kit (Clontech, Mountain View, Calif.) according to the manufactures instructions. Primers used for reverse transcription were GATTACGCCAAGCTTTATGCAAGGCT-TACAACCACA (heavy chain) (SEQ ID NO:11), GAT-TACGCCAAGCTTCACAATTTTCTTGTCCACCTTGGT-GC (heavy chain nested) (SEQ ID NO:12), GATTACGC-CAAGCTTCTCATTCCTGTTGAAGCTCTTGACAAT (kappa light chain) (SEQ ID NO:13), GATTACGC-CAAGCTTACACTCAGCACGGGACAAACTCTTCTC (lambda light chain 1, 4) (SEQ ID NO:14), GATTACGC-CAAGCTTACACTCTGCAGGAGACAGACTCTTTTC (lambda 2,3) (SEQ ID NO:15).

Proliferation and cytokine production. Cells were isolated from spleen and peripheral lymph nodes of NOD.BDC2.5 transgenic mice, the red blood cells were lysed by Tris-buffered ammonium chloride, and the cells were labeled with CFSE (ThermoFisher Scientific, Waltham, Mass.). Labeled cells were resuspended in complete DMEM media at a final concentration of 4×10$^6$ cells/mL and p63 or p31 peptide was added to a final concentration of 0.05 µM. Purified monoclonal antibody or 50 µL of hybridoma supernatant was added to each well containing 200 µL of cells in a 96-well plate, and incubated for 4 days at 37° C. with 5% CO$_2$. Cells were harvested, resuspended in 2.4G2 Fc block for 10 minutes at 4° C., and stained at 1:100 dilution for 30 minutes at 4° C. with antibodies against CD4-BV510 (RM4-5, BD Biosciences, Franklin Lakes, N.J.), CD8α-BV650 (53-6.7, BD Biosciences, Franklin Lakes, N.J.), CD3e-PerCp-Cy5.5 (KT4, BD Biosciences, Franklin Lakes, N.J.), B220-ef450 (RA3-6B2, eBioscience, ThermoFisher Scientific, Waltham, Mass.), CD11c-ef450 (N418, eBioscience, ThermoFisher Scientific, Waltham, Mass.), CD11b-ef450 (M1/70, eBioscience, ThermoFisher Scientific, Waltham, Mass.), T cell receptor (TCR) Vβ4-PE (KT4, BD Biosciences, Franklin Lakes, N.J.) and dead cells were gated out using a viability ghost red dye (Tonbo Biosciences, San Diego, Calif.), and run on a LSRII Fortessa X-20 flow cytometer (Becton Dickinson, Franklin Lakes, N.J.) and analyzed using FlowJo software (v10). For antibody dose response curves, cells were isolated from NOD.BDC2.5 transgenic mice, labeled with CFSE as described above, and cultured with p31 or p63 (0.05 µM) with varying doses of FS1 MAb, or isotype control (Bio X Cell, West Lebanon, N.H.). After a 4 day incubation at 37° C. with 5% CO$_2$, cells were harvested for flow cytometry, while supernatants were analyzed using ProcartaPlex Assay kit EPX170-26087-901 (eBioscience, ThermoFisher Scientific, Waltham, Mass.).

Antibody staining of peptide pulsed antigen presenting cells. Purified monoclonal antibody was directly conjugated to ALEXA-FLUOR-488 (AF488) by protein labeling kit (ThermoFisher Scientific, Waltham, Mass.) according to the manufacturer's protocol. Splenocytes were isolated from NOD mice, red blood cells (RBCs) lysed, and resuspended at in complete DMEM at 6×10$^6$ cells/mL. p63 or OVA$_{141\text{-}160}$ was added to the media at a final concentration of 40 µM and the cells were incubated for 1.5 hours at 37° C. with 5% CO$_2$. Cells were harvested incubated in 2.4G2 for 10 minutes on ice and stained at 1:100 dilution for 30 minutes at 4° C. with FS1-AF488 and antibodies against CD4-BUV395 (GK1.5, BD Biosciences, Franklin Lakes, N.J.), CD8α-APC-ef780 (53-6.7, eBioscience, ThermoFisher Scientific, Waltham, Mass.), CD3F-BV650 (145-2C11, BD Biosciences), B220-PE (RA3-6B, Tonbo Biosciences, San Diego, Calif.), CD11c-PE-Cy (N418, eBioscience, ThermoFisher Scientific, Waltham, Mass.), CD11b-PerCp-Cy5.5 (M1/70, Tonbo Biosciences, San Diego, Calif.), F4/80-APC (BM8.1, Tonbo Biosciences, San Diego, Calif.), IA$^{g7}$-biotin (10.2-16, Bio X Cell, West Lebanon, N.H.),SA-BV421 (Biolegend, San Diego, Calif.) and dead cells were gated out using GHOST DYE Violet 510 (Tonbo Biosciences, San Diego, Calif.), and run on a LSRII Fortessa X-20 flow cytometer (Becton Dickinson, Franklin Lakes, N.J.) and analyzed using FlowJo software (v10).

In vivo blockade of T cell activation. NOD mice were administered 50 micrograms (µg) acetylated-p63 peptide with either 250 µg FS1 or Y-Ae MAb in PBS containing 2 µg lipopolysaccharide (Sigma-Aldrich, St. Louis, Mo.) by intravenous injection in the tail vein. Four days post-injection mice were euthanized and splenocytes were isolated and RBCs lysed as above. Cells were stained with both APC and PE-conjugated p63:IA$^{g7}$ tetramers followed by magnetic enrichment of double tetramer positive cells as previously described (Pauken et al. *J Immunol* 191:4913-4917 (2013); Tubo et al. *Cell* 153:785-796 (2013)). Enriched cells were incubated with 2.4G2 Fc block for 10 minutes at 4° C. and stained with surface antibodies at 1:100 dilution for 30 minutes at 4° C. against CD3e-APC-ef780 (17A2, eBioscience, ThermoFisher Scientific, Waltham, Mass.), CD4-BUV395 (GK1.5, BD Biosciences, Franklin Lakes, N.J.), CD8α-BV650 (53-6.7, BD), CD44-BV786 (IM7, BD Biosciences, Franklin Lakes, N.J.), B220-PerCp-Cy5.5 (RA3-6B2, eBioscience, ThermoFisher Scientific, Waltham, Mass.), CD11b-PerCp-Cy5.5 (M1/70, Tonbo Biosciences, San Diego, Calif.), CD11c-PerCp-Cy5.5 (N418, eBioscience, ThermoFisher Scientific, Waltham, Mass.), and GHOST DYE Violet 510 (Tonbo Biosciences, San Diego, Calif.) for 30 minutes at 4° C. The cells were then fixed using the Foxp3 staining buffer kit (eBioscience, ThermoFisher Scientific, Waltham, Mass.) and stained with anti-Ki67-PE-Cy7 (SolA15, eBioscience, ThermoFisher Scientific, Waltham, Mass.) antibodies for 1 hour at 4° C., and run on a LSRII Fortessa X-20 flow cytometer (Becton Dickinson, Franklin Lakes, N.J.) and analyzed using FlowJo software (v10).

Infections. C57BL/6 mice were injected intravenously with 10$^7$ actA-deficient *Listeria monocytogenes* expressing 2W protein (Ertelt et al. *J Immunol* 182:3032-3038 (2009)) and on the same day injected intravenously with 500 μg of W6 (anti-2W:IA$^b$) blocking antibody. Seven days later, splenocytes were isolated, and stained as above and magnetically enriched for 2W:IA$^b$-PE tetramer. Cells were run on a LSRII Fortessa X-20 flow cytometer (Becton Dickinson, Franklin Lakes, N.J.) and analyzed using FlowJo software (v10).

Foot pad immunization, antigen presenting cell isolation and staining. NOD hind limb foot pads were injected with 100 μL total volume containing 200 μg of p63 or OVA$_{141-160}$ peptide in PBS. One and half hours later the popliteal lymph nodes were removed, minced, and digested in RPMI containing 2% FCS, collagenase D (40 U/mL), and DNase I (250 μg/mL) for 30 minutes at 4° C. Cells were then washed with Hanks balanced salt solution containing 5 mM EDTA and 2% FCS, centrifuged, and stained with surface antibodies and analyzed by flow cytometry as described above using the FS1 AF488 antibody.

Ear pinna immunization, antigen presenting cell isolation and staining. C57BL/6 mice were immunized intradermally in the ear pinna with 10 μg either Ovalbumin (OVA) or 2W-GFP plus 1 μg double mutant labile toxin (Norton et al. *Vaccine* 33:1909-1915 (2015)) or 10 μg CpG (Sigma-Aldrich, St. Louis, Mo.). After 24 hours, the cervical lymph nodes were removed, dissociated using a 100-micron mesh and mechanically disrupted, and digested with 300 Mand1 U/mL Collagenase D (Roche Applied Sciences) for 30 minutes at 37° C. in 1×PBS+2% FBS. Cells were then washed 1×PBS+2% FBS, centrifuged, and Fc receptors were blocked in 100 μL 2.4G2 hybridoma supernatant containing 2% rat and mouse serum for 10 minutes at room temperature. For surface staining, 1 μg of biotinylated W6 antibody was added to the cells and incubated on ice for 45 minutes, washed with PBS+2% FCS, followed by staining for 30 minutes at 4° C. with antibodies CD11c-PerCpCy5.5 (N418, BioLegend, San Diego, Calif.), CD11b-AF700 (M1/70, BioLegend, San Diego, Calif.), CD19-ef450 (1D3, eBioscience, ThermoFisher Scientific, Waltham, Mass.), MHCII-FITC (M5/114.15.2, BioLegend, San Diego, Calif.), DEC-205-PE (205yekta, eBioscience, ThermoFisher Scientific, Waltham, Mass.), and streptavidin-APC (BioLegend, San Diego, Calif.). All antibodies were used at 1:100 dilution except CD11c and CD19 were used at 1:40 and CD11b was used at 1:200. The cells were then run on a LSRII flow cytometer (Becton Dickinson, Franklin Lakes, N.J.) and analyzed using FlowJo software (v10).

Statistical Analysis. Data display and statistical analysis was conducted using Prism software (GraphPad Prism v6, GraphPad Software, San Diego, Calif.). Statistical significance was analyzed using the two-tailed Student's t-test for comparison of two mean. Values of p≤0.05 were considered significant.

Sequence availability. Sequence data that support the findings of this study have been deposited in GenBank with the primary accession codes: FS1 Heavy chain KU955585 (available on the world wide web at ncbi.nlm.nih.gov/nuccore/KU955585), FS1 Light chain KU955586 (available on the world wide web at ncbi.nlm.nih.gov/nuccore/KU955586), W6 Heavy chain KU955587 (available on the world wide web at ncbi.nlm.nih.gov/nuccore/KU955587), and W6 Light chain KU955588 (available on the world wide web at ncbi.nlm.nih.gov/nuccore/KU955588).

Results

Figure 7A:
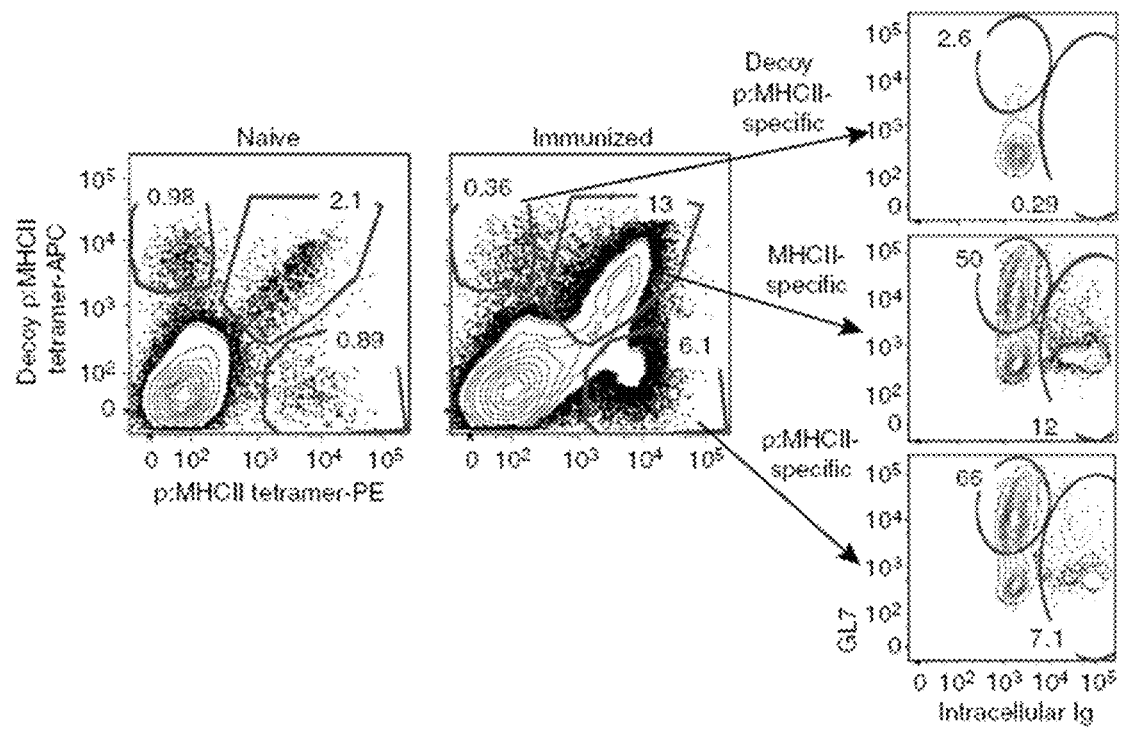
FIG. 7A and FIG. 7B show enrichment and phenotypic analysis of p:MHCII-specific B cells of Example 2.
Figure 7B:
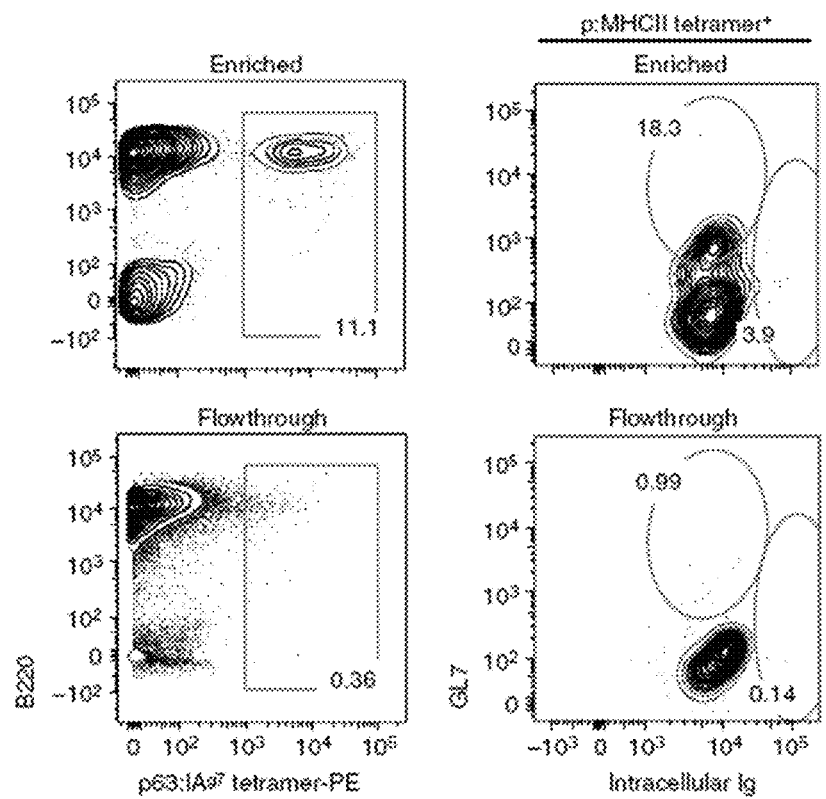

The workflow and the necessary steps for p:MHCII MAb generation as described in this Example are illustrated in FIG. 1. Generation and validation of p:MHCII MAb can be completed in less than 8 weeks. To develop a reagent to block T cell receptor (TCR) recognition of a diabetes-relevant peptide, antibodies against p63 peptide in the context of IA$^{g7}$ MHC II molecule were initially developed, given that p63-activated BDC2.5 CD4$^+$ T cells mediate accelerated autoimmune diabetes when transferred into wild type non-obese diabetic (NOD) hosts. Splenocytes from five p:MHCII (p63:IA$^{g7}$) immunized BALB/c mice were isolated and magnetically enriched for antigen specific B cells using PE conjugated p63:IA$^{g7}$ tetramers followed by anti-PE magnetic beads (Pape et al. *Science* 331:1203-1207 (2011)) To validate successful priming and expansion, the phenotype of p:MHCII-specific B cells was analyzed in naïve mice compared to day 7 post immunization (FIG. 7A). Antigen-specific B cells were identified by p:MHCII tetramer excluding those that bound to SA-PE or SA-APC using SA-PE-AF647 or SA-APC-DYLIGHT 755 from immunized mice, compared to a decoy p:MHCII reagent (FIG. 7A). Three distinct subsets of antigen-specific B cells (p:MHCII specific, MHCII specific, and decoy p:MHCII specific) (Pape et al. *Science* 331:1203-1207 (2011); Taylor et al. *J Exp Med* 209:2065-2077 (2012)) were evaluated for GL7 and intracellular Ig expression associated with mature germinal center B cells. Phenotypic analysis demonstrates the p:MHCII-PE$^+$ population is enriched for mature germinal center B cells (GL7$^+$ and intracellular Ig$^-$) demonstrating successful priming and T cell help (FIG. 7A). The enrichment approach at day 3 post antigen boost was verified, prior to hybridoma fusion. Magnetic enrichment resulted in an increase to 11.1% of the B cells staining positive for p63:IA$^{g7}$-PE tetramer, and phenotypic markers demonstrating the presence of germinal center B cells within this population (FIG. 7B). The enriched fraction contained 2.1×10$^7$ cells, a 23-fold reduced compared to the starting population. These cells were subsequently fused with SP2/0 myeloma cells and plated onto ten 100 millimeter (mm) plates containing semi-solid media under hypoxanthine-aminopterin-thymidine (HAT) selection. Fourteen days after plating, 190 colonies were picked and screened by ELISA. Without enrichment, 50 plates would have been required to screen 5×10⁸ cells, and these 50 plates likely would have contained at least 5000 colonies, most of which could not have been selected or screened for further analysis due to time and reagent constraints. Thus, enrichment allowed screening of every visible colony and saved significant time and reagents.

After expansion of each colony, secreted antibody in the culture supernatant was assessed for binding to p63:IA$^{g7}$ compared to decoy InsB$_{10-23}$:IA$^{g7}$ by ELISA. Thirty-two of the 190 colonies produced antibodies that bound to both p63:IA$^{g7}$ and InsB$_{10-23}$:IA$^{g7}$, indicating specificity for an IA$^{g7}$ epitope (Table 1).

TABLE 1

Efficiency of generating hybridomas producing p:MHCII specific antibodies

| Antigen | # Mice immunized | # Hybridomas screened | # Hybridomas⁺ for MHCII (%)* | # Hybridomas⁺ for peptide:MHCII (%) |
| --- | --- | --- | --- | --- |
| p63:IA$^{g7}$ | 5 | 190 | 32 (16.8) | 11 (5.8)⁺ |
| 2W:IA$^b$ | 2 | 576 | 234 (40.6) | 5 (0.9)⁺ |
| LLO:IA$^b$ | 2 | 576 | 236 (40.9) | 32 (13.5)* |
| Ins:IA$^{g7}$ | 2 | 576 | 22 (3.8) | 11 (1.9)* |
| p31:IA$^{g7}$ | 2 | 480 | 21 (4.4) | 14 (2.9)* |
| mimetope:IA$^{g7}$ | 2 | 480 | 21 (4.4) | 12 (2.5)* |

*Specificity as defined by functional assay blocking T cell proliferation or MAb binding to APCs.
§Specificity as defined by positive ELISA plate compared to decoy pMHCII complex.

Figure 8A:
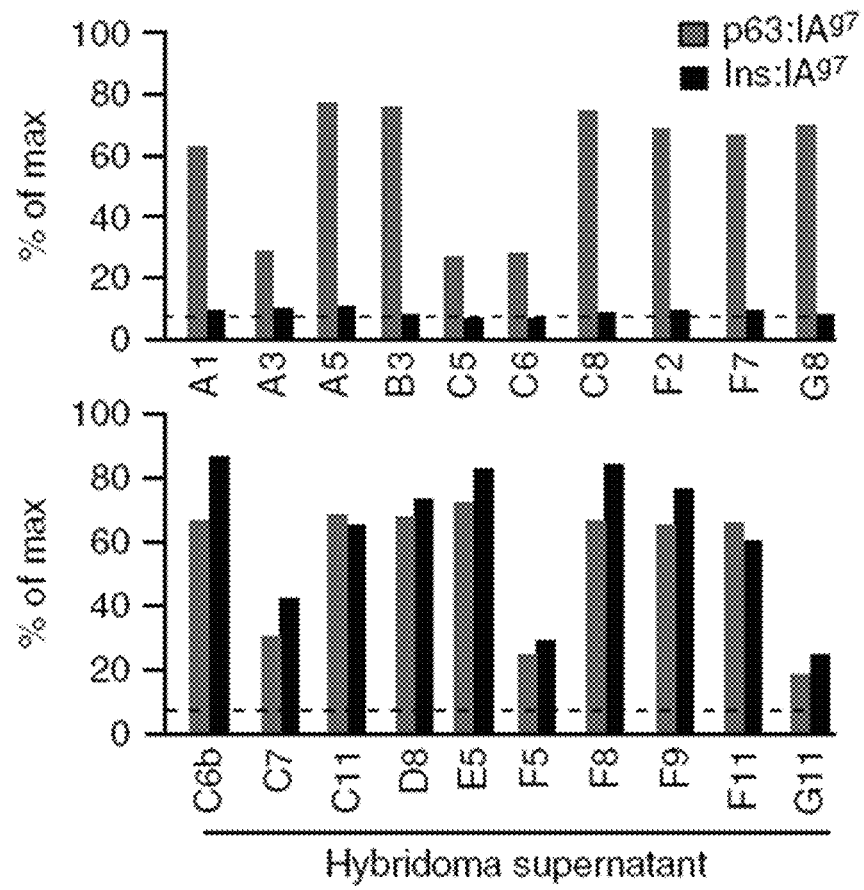
FIG. 8A shows ELISA results from twenty independent hybridomas presented as percent maximum absorbance compared to anti-IA$^{g7}$ mouse hybridoma clone 10-2.16 as positive control. Plates were coated with p63:IA$^{g7}$ monomer and compared to InsB$_{9-23}$:IA$^{g7}$ monomer-coated plates. Supernatant was added and secondary antibody was used to measure binding by ELISA. Media alone was used for a negative control (dashed line).
Figure 8B:
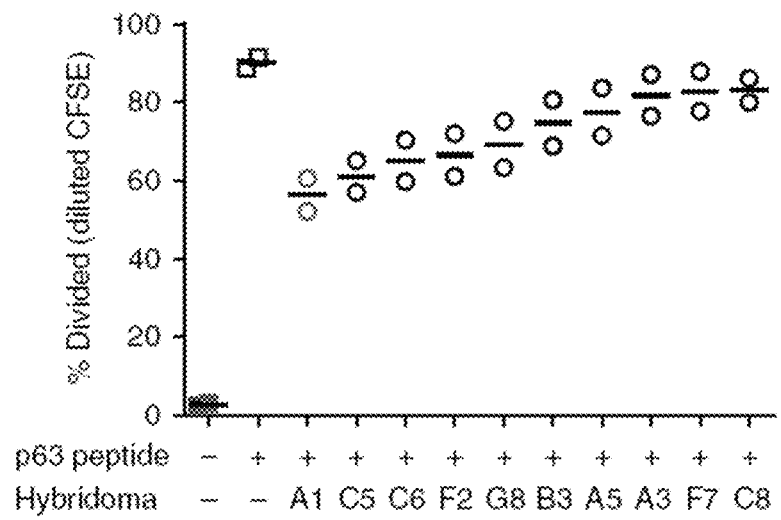
FIG. 8B shows carboxyfluorescein succinimidyl ester (CFSE) proliferation in response to p63 peptide. The assay was performed using splenocytes from BDC2.5 mice. The percent of divided CD4$^+$ T cells is shown with maximum division with peptide alone (87.5%) and inhibition with each hybridoma supernatant screened. Data are representative from two independent experiments.

In contrast, 11 hybridomas produced antibodies that bound only p63:IA$^{g7}$ (34.4% success rate for p:MHC or 5.8% overall), suggesting the desired specificity for this peptide bound to IA$^{g7}$ (Table 1). FIG. 8A illustrates twenty clones, ten that reacted to both p63:IA$^{g7}$ and InsB$_{10-23}$:IA$^{g7}$, and ten that are unique for p63:IA$^{g7}$. The 10 clones that uniquely bound p63:IA$^{g7}$ were further characterized for TCR blocking ability to limit in vitro antigen specific T cell proliferation (FIG. 8B). Splenocytes were isolated from TCR transgenic BDC2.5 mice, labeled with carboxyfluorescein (CFSE) and cultured with p63 peptide in the presence or absence of hybridoma supernatant for four days. BDC2.5 splenocytes incubated with peptide only resulted in 87.5% CD4⁺ T cells proliferating, while T cells incubated with peptide plus hybridoma A1 limited BDC2.5 T cell proliferation to 56% (FIG. 8B). The remaining 9 hybridomas screened had varying degrees of inhibition (FIG. 8B). An isotype specific ELISA was then used to determine that A1 antibody was IgG1.

Figure 8C:
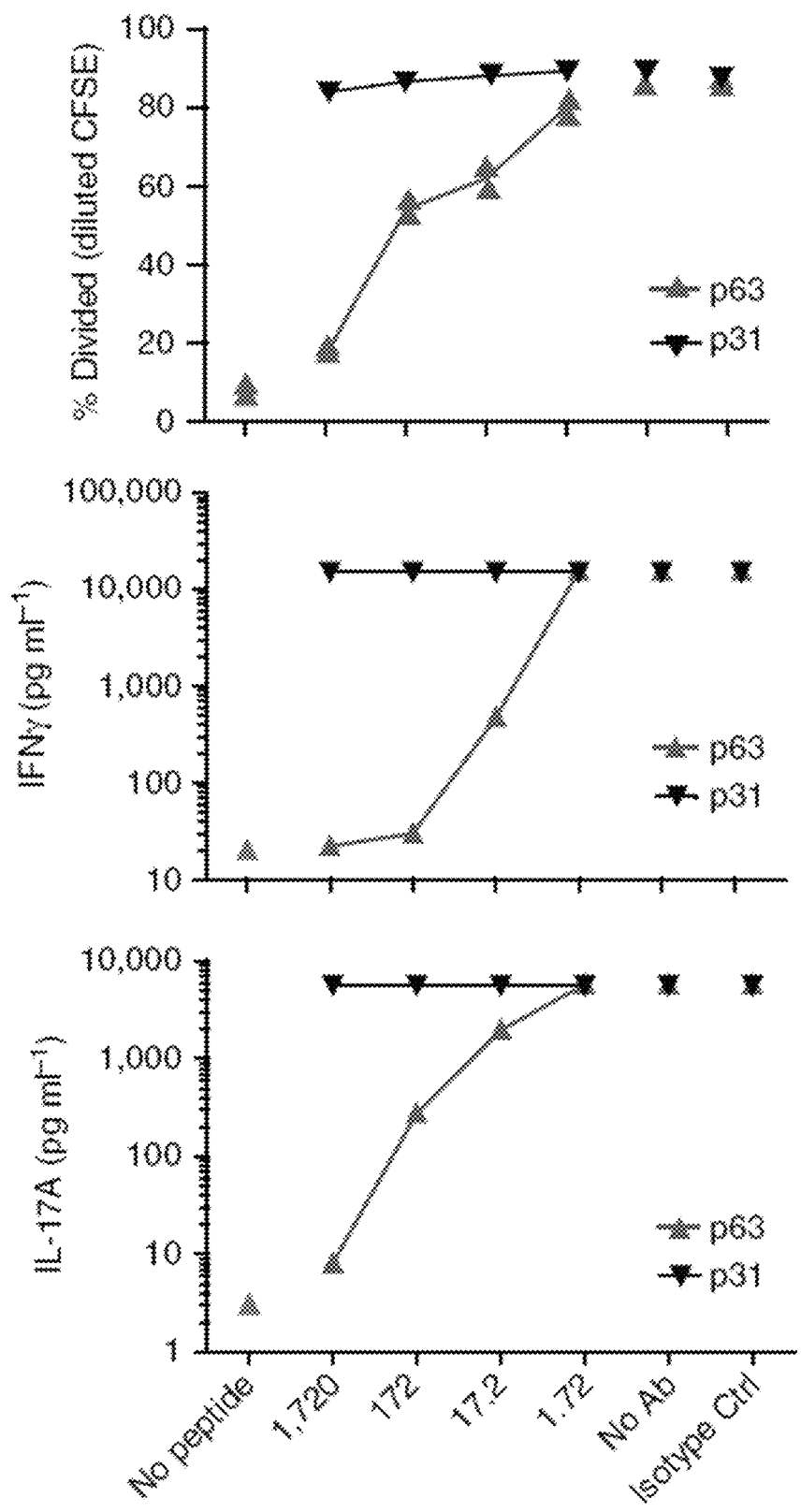
FIG. 8C shows the effect of culturing CFSE-labelled BDC2.5 T cells for 4 days in the presence of p63 or p31 peptide with varied concentrations of FS1 MAb or isotype control IgG1 antibody (1.72 mM). The percent divided CD4$^+$ T cells is shown for each concentration of blocking FS1 MAb compared with maximum proliferation with no antibody (no Ab) or isotype Ab (top panel). FS1 MAb effects on IFNγ cytokine production from the cultured cells (middle panel) and IL-17A cytokine production (bottom panel) are also shown. Data are representative of two independent experiments in duplicate for each antigen concentration.
Figure 8D:
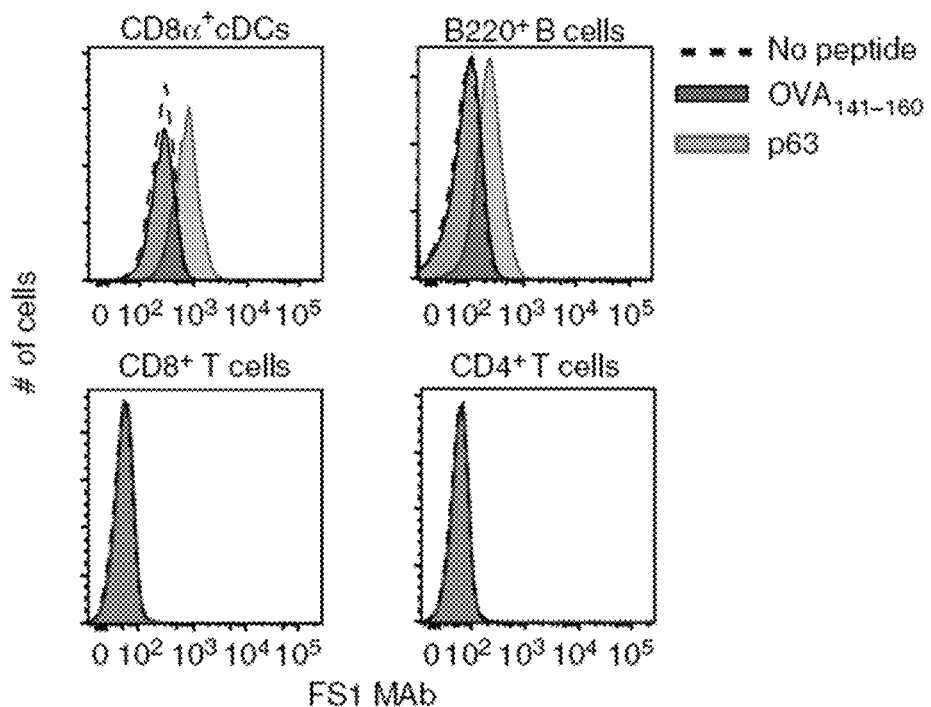
FIG. 8D shows in vitro antibody staining on antigen-presenting cells following peptide pulse with p63 or OVA$_{141-160}$ using purified clone FS1 MAb to detect p63 loaded conventional dendritic cells (cDCs) (CD8α$^+$, CD11c$^+$, MHCII$^+$, CD3ε$^-$, F4/80$^-$), and B cells (B220$^+$, MHCII$^+$, CD11c$^-$, CD3ε$^-$, F4/80$^-$) but not CD4$^+$ or CD8$^+$ T cells (CD3ε$^+$, CD11c$^-$, CD11b$^-$, B220$^-$, F4/80$^-$) compared with no p63 peptide negative control. Data are representative of three independent experiments.
Figure 8E:
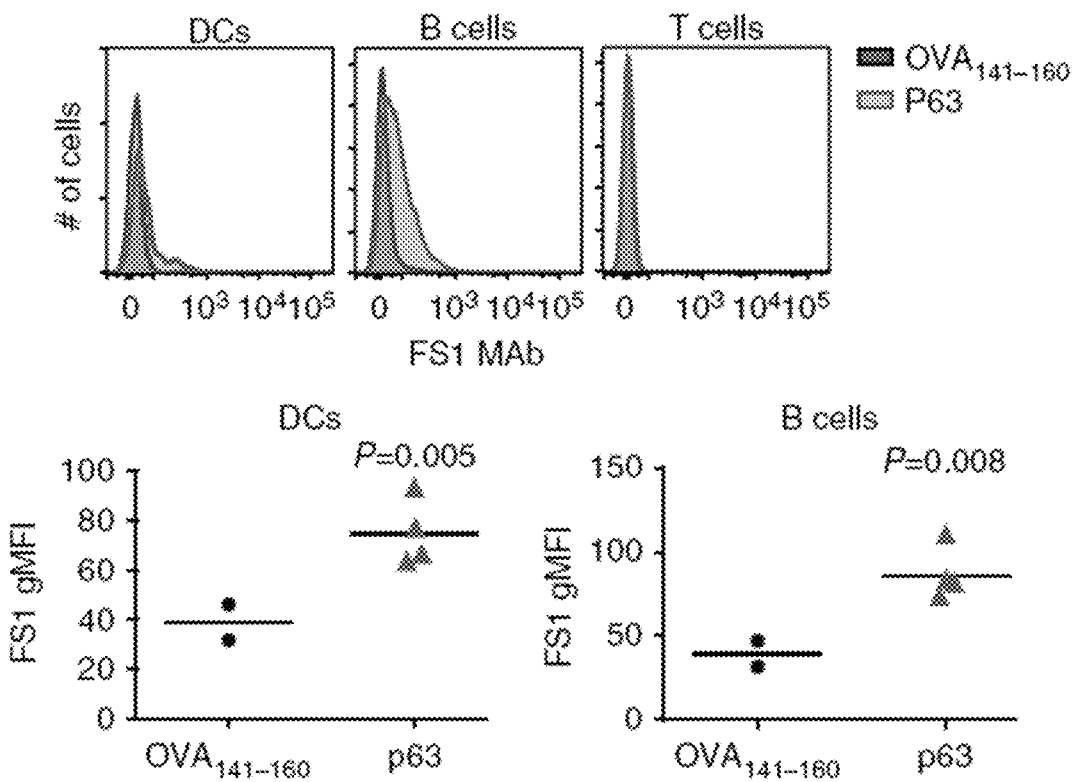
FIG. 8E shows in vivo staining of antigen-presenting cells with FS1 MAb following footpad immunization. NOD mice received p63 or OVA$_{141-160}$ peptide and 1.5 hours following injection the popliteal lymph node was collected and stained for antigen-specific presentation using biotinylated FS1 MAb. FS1 MAb staining was detected on DCs and B cells, but not T cells using fluorochrome-linked streptavidin. Statistical significance was calculated using a two-tailed Student's t-test. Data are representative from two independent experiments with 2-4 mice per group.

A large scale purification was performed to obtain purified MAb from hybridoma A1 (named FS1). Using the FS1 MAb (anti-p63:IA$^{g7}$) an in vitro dose response assay was performed an 80.5% specific reduction in proliferation was demonstrated with 1.72 µM FS1 MAb (FIG. 8C). In contrast, the FS1 MAb only reduced BDC2.5 T cell proliferation to another BDC2.5 mimetope (p31) by 5.6% compared to isotype control (FIG. 3C). p63-activated BDC2.5 T cells demonstrated 99.85% reduction in IFNγ production when cultured with 1.72 µM of FS1 MAb, compared to isotype control (FIG. 8C). Importantly, IFNγ production by p31-activated BDC2.5 T cells was not altered (FIG. 8C). A similar trend with IL-17A was noted (FIG. 3C). Taken together, these findings illustrate the specificity of the FS1 MAb as p31 differs from p63 by two amino acids at positions P-1 and P1 of the MHCII binding pocket (Judkowski et al. *J Immunol* 166:908-917 (2001)). As an extension of specific binding, splenocytes from NOD mice were p63 peptide pulsed and stained with labeled FS1 MAb illustrating CD8α conventional dendritic cells (cDCs) and B220⁺ B cells stained positive for p63 peptide but not ovalbumin peptide (OVA$_{141-160}$) control (FIG. 8D). The uniform histogram shift suggests a large portion of the DCs and B cells stained with varying levels of FS1 MAb demonstrating peptide presentation in vitro (FIG. 8D). CD4⁺ and CD8⁺ T cells did not stain positive for the FS1 MAb (FIG. 8D). Immunostaining was next performed to demonstrate peptide binding to MHCII in vivo. NOD mice were injected with p63 or OVA peptide in the footpad and 1.5 hours later popliteal lymph node cells were stained with FS1 antibody to identify p63 loaded antigen presenting cells (FIG. 8E). Both DCs and B cells had significantly increased FS1 MAb staining in response to p63 peptide pulsed compared to OVA peptide (p=0.005 and p=0.008, respectively), while T cells showed no specific staining (FIG. 8E).

Figure 9A:
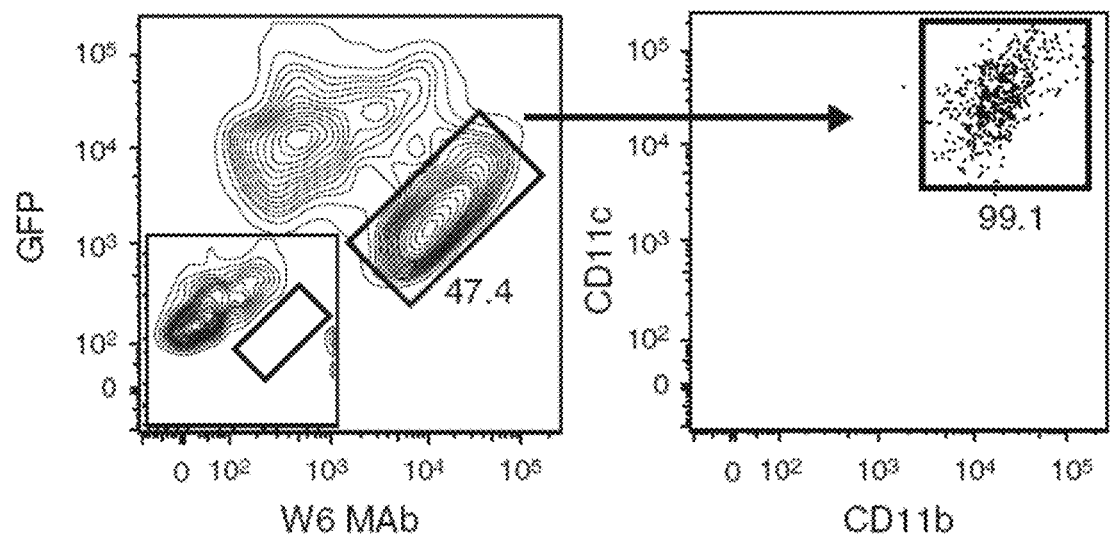
FIG. 9A shows in vitro antigen presentation on bone marrow-derived dendritic cells isolated from C57BL/6 mice. Cells were stained with W6 MAb after 24 hours pulse with GFP covalently linked to 2W peptide. GFP and W6 MAb double-positive cells are shown compared to isotype control (insert). Data are representative of two independent experiments with 3 mice per group.
Figure 9B:
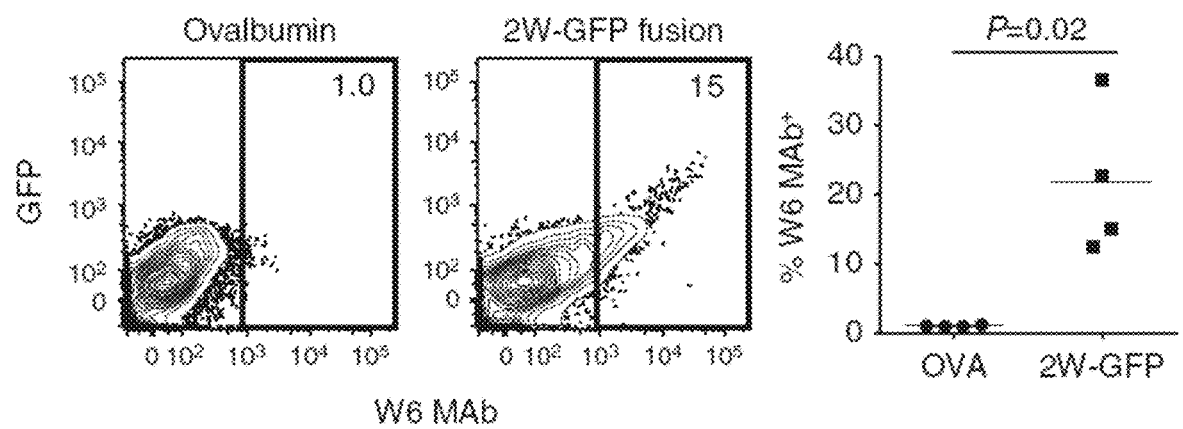
FIG. 9B shows in vivo immunostaining of 2W antigen-presenting cells. Mice were immunized intradermally in the ear with either ovalbumin (OVA) or 2W-GFP. 24 hours post immunization, cervical lymph nodes were collected, dissociated and gated for lymphocyte size, singlets, CD19$^-$ and MHCII$^+$. Statistical significance was calculated using a two-tailed Student's t-test. Data are representative of two independent experiments with four animals per group.
Figure 9C:
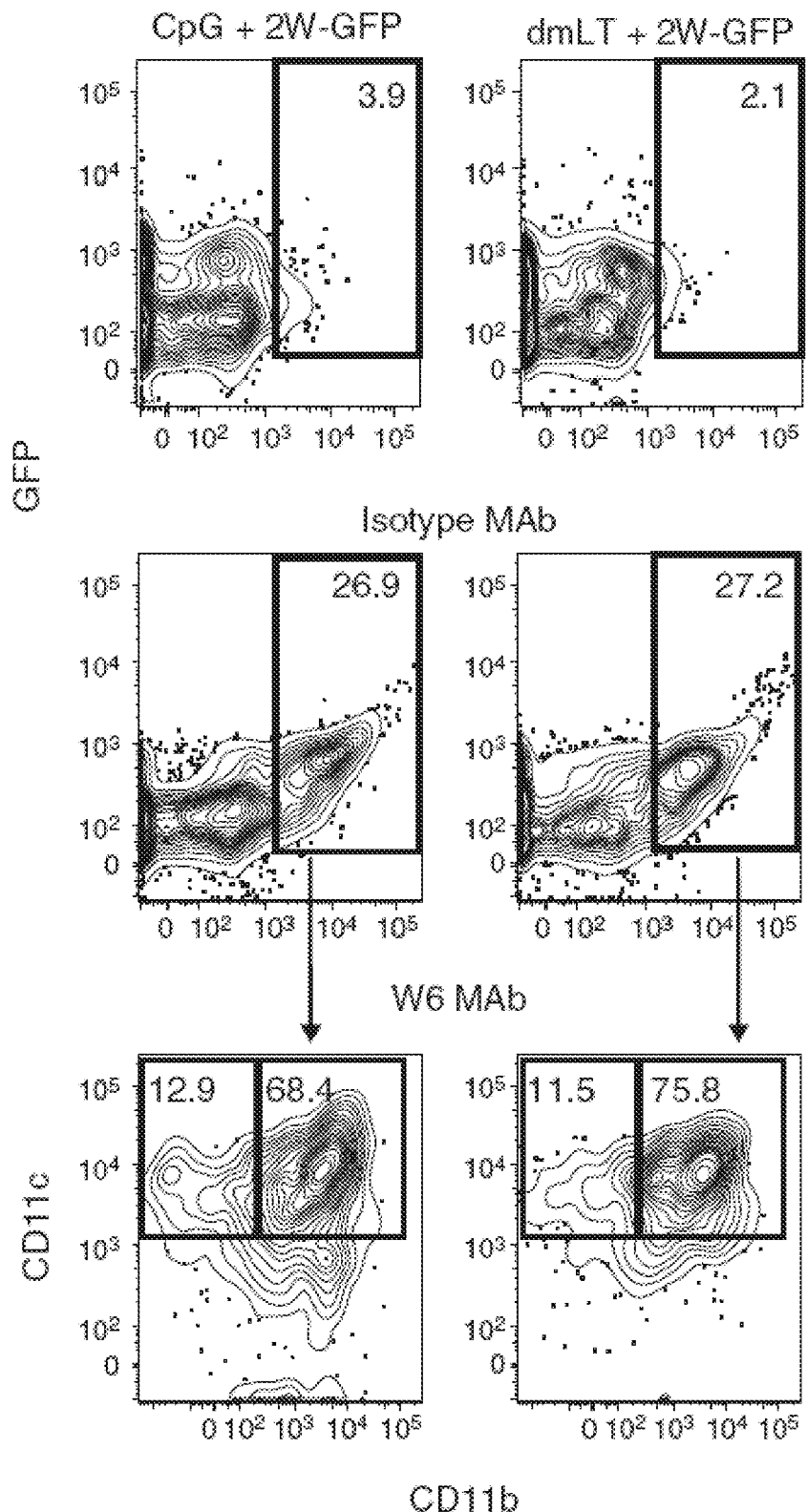
FIG. 9C shows percentages of CD19$^-$, CD11b$^+$, CD11c$^+$ dendritic cells in mice immunized with 2W-GFP and either CpG or dmLT (Norton et al. *Vaccine* 33:1909-1915 (2015)) assayed using W6 MAb. Twenty-four hours after immunization, draining lymph nodes were assayed using W6 MAb. Data are representative of four independent experiments with 2-3 mice per group.

Using this methodology, an antibody specific for the peptide 2W was also generated (Moon et al. *Nat Protoc* 4:565-581 (2009); Rees et al. *Proc Natl Acad Sci USA* 96:9781-9786 (1999)) bound to IA$^b$ (named W6). Using this reagent, in vitro antigen loading and presentation were validated using bone marrow derived dendritic cells that were pulsed with green fluorescent protein (GFP)-linked 2W peptide. Results in FIG. 9A demonstrate that 47% of the GFP positive cells were W6 MAb (anti-2W:IA$^b$) positive and were mostly CD11c⁺CD11b⁺ double positive cells. In vivo antigen loading and presentation were also validated. C57BL/6 mice were immunized intradermally with either ovalbumin protein or 2W-GFP. At 24 hours post injection, MHCII⁺ antigen presenting cells from the draining lymph node had increased W6 MAb reactive populations (15%) compared to 1% of controls (FIG. 9B). In a separate in vivo model, the W6 MAb was used to identify antigen presenting cells immunized with two different adjuvants. C57BL/6 mice were immunized with 2W-GFP and either 5'-cytosine-phosphate-guanine-3' (CpG) or double-mutant heat-labile toxin (dmLT) (Norton et al. *Vaccine* 33:1909-1915 (2015)). Twenty-four hours later, draining lymph nodes were assayed by flow cytometry for antigen-specific presentation using the W6 antibody. Shown in FIG. 9C, the W6 MAb identified 27% of the DCs containing GFP compared to 3% in the isotype control group and all these cells were CD11b⁺CD11c⁺CD19⁻ dendritic cells. These results demonstrate that W6 MAb can identify different subsets of antigen presenting cells in vivo.

Figure 10A:
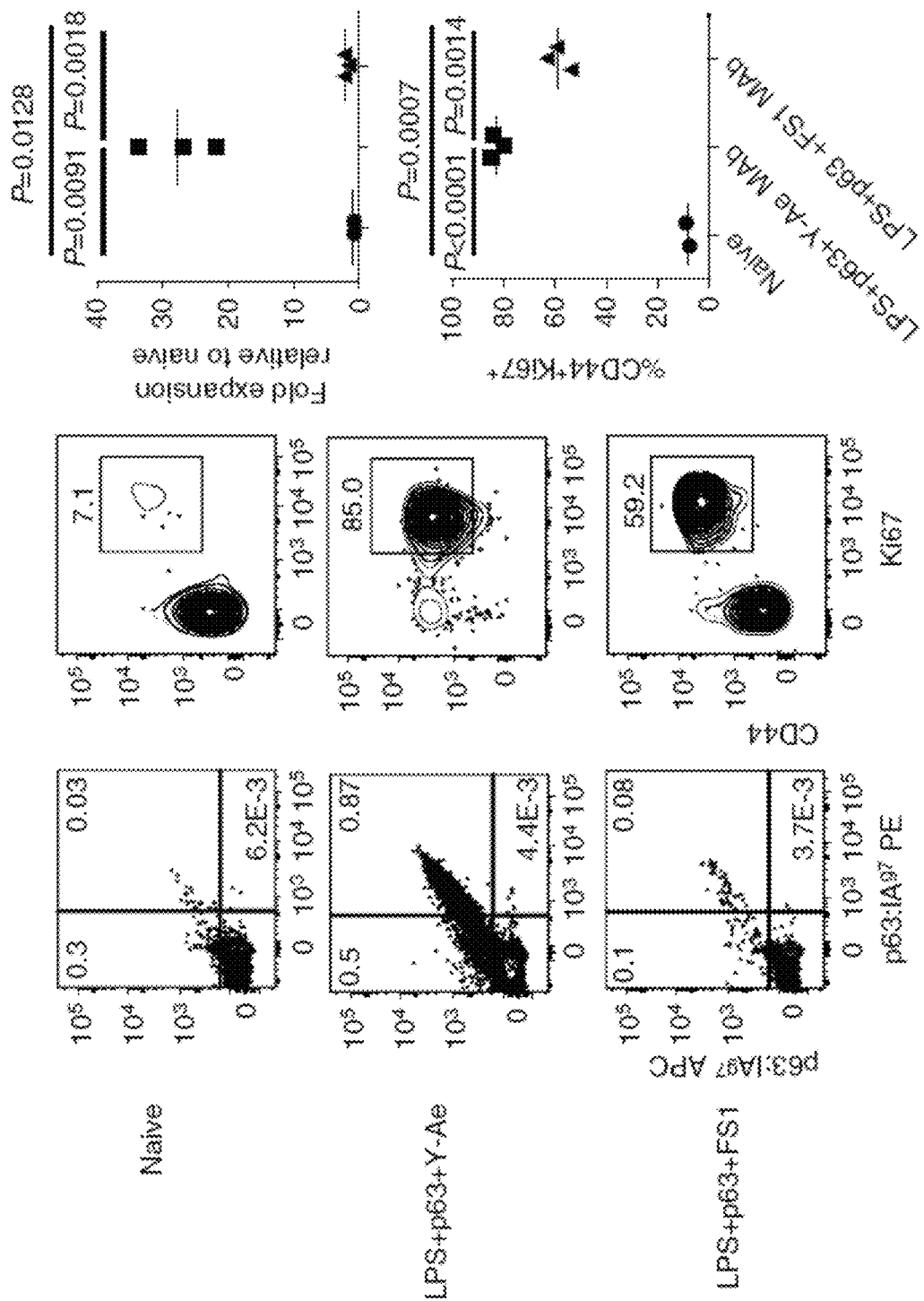
FIG. 10A shows in vivo blockade of antigen-specific proliferation and cell cycle progression 4 days after intravenous (i.v.) administration of FS1 MAb plus p63 and LPS compared to Y-Ae (anti-IEα:IA$^b$), control treatment or untreated naïve mice. p63:IA$^{g7}$ tetramer PE and APC double positive cells from the spleen were enriched and gated on lymphocyte size, singlets, live cells, B220$^-$, CD11c$^-$, CD11b$^-$, CD3ε$^+$, and CD4$^+$. Statistical significance was calculated using a two-tailed Student's t-test. Data are representative of two independent experiments with 2-3 mice per group.
Figure 10B:
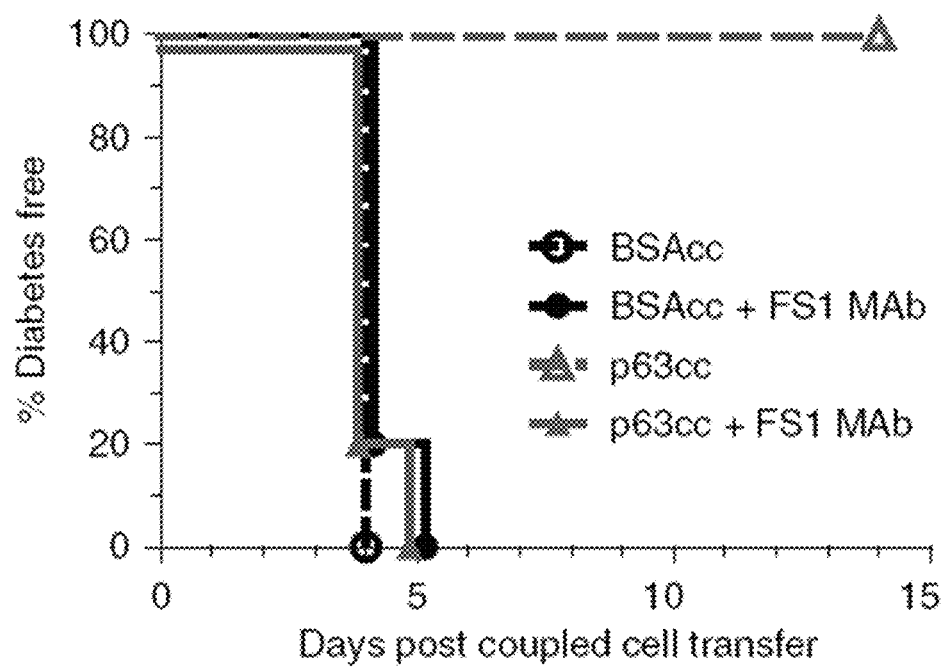
FIG. 10B shows in vivo blockade of antigen-specific tolerance using FS1 MAb to prevent ethylene-carbodiimide antigen-fixed-coupled cell tolerance. NOD mice received activated BDC2.5 TCR transgenic CD4$^+$ T cells to induce diabetes. Ten mice per group received either p63-coupled cells or BSA-coupled cells. Five mice per treatment received FS1 MAb or control. Mice were followed daily for diabetes after day 3 by blood glucose measurements. Data are representative of two independent experiments.

Next, whether MAbs directed against p:MHCII could prevent TCR recognition in vivo to limit T cell proliferation was determined. NOD mice were challenged with p63 peptide plus lipopolysaccharide (LPS) with FS1 MAb or Y-Ae³ (anti-Eα:IA$^b$) as a negative control. Four days post challenge a significant reduction in antigen specific T cell expansion with FS1 MAb administration was measured (FIG. 10A). Using dual fluorochrome tetramer staining and flow cytometry, 30-fold expansion of p63 specific T cells stimulated with p63+LPS+Y-Ae MAb control, compared to only a 2-fold expansion with p63+LPS+FS1 MAb over naïve cells was detected (FIG. 10A). In addition to decreased expansion, the FS1 MAb was observed to decrease activation and cell cycle progression (FIG. 10A). Next, the FS1 MAb was used in vivo to prevent antigen specific tolerance, resulting in rapid autoimmune diabetes. Specifically, activated BDC2.5 T cells were transferred after 4 days in vitro stimulation into wild-type NOD pre-diabetic recipients followed by injection of ethelyene-carbodiimide (ECDI) fixed p63-peptide coupled cells (p63cc) to induce tolerance (Pauken et al. *J Immunol* 191:4913-4917 (2013); Pauken et al. *Diabetes* 62:2859-2869 (2013)) and either control or FS1 MAb and monitored the mice for diabetes. p63cc completely prevented diabetes induction in 100% of the mice, while control bovine serum albumin coupled cells (BSAcc)-treated mice develop severe diabetes (FIG. 10B). Mice given p63cc and FS1 MAb developed diabetes, indicating the FS1 MAb prevented the induction of antigen specific tolerance in vivo.

Figure 11A:
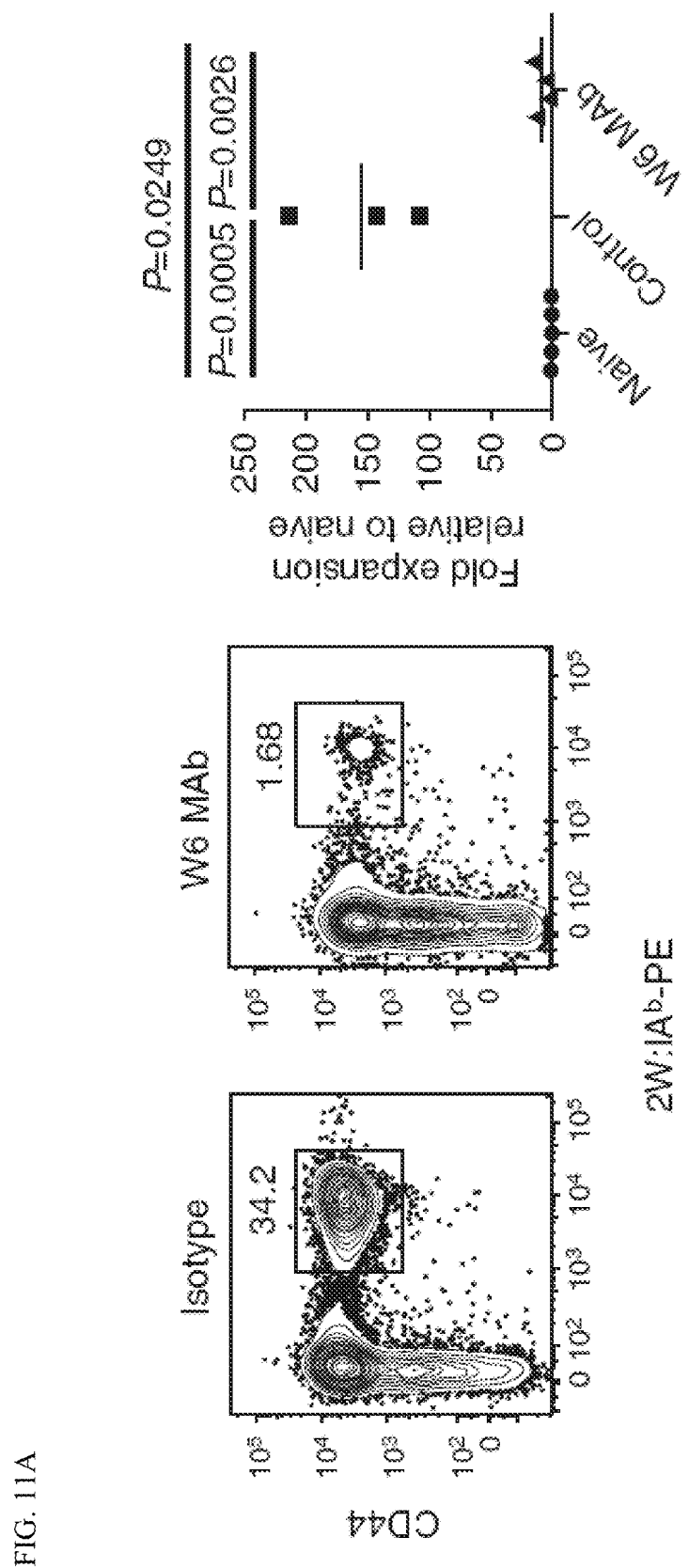
FIG. 11A. C57BL/6 mice were infected with *Listeria monocytogenes* expressing 2W. Seven days post infection and W6 antibody treatment, 2W-specific cells were magnetically enriched from the spleen. Cells were gated on lymphocyte size, singlets, CD19$^-$, F4/80$^-$, CD11c$^-$, CD11b$^-$, CD3ε$^+$, and CD4$^+$. Shown are representative FACS plots for CD44$^{hi}$ versus 2W:IA$^b$ tetramer PE$^+$ cells and fold expansion of antigen-specific cells relative to uninfected mice. Data are representative of two independent experiments with 3-5 mice per group.
Figure 11B:
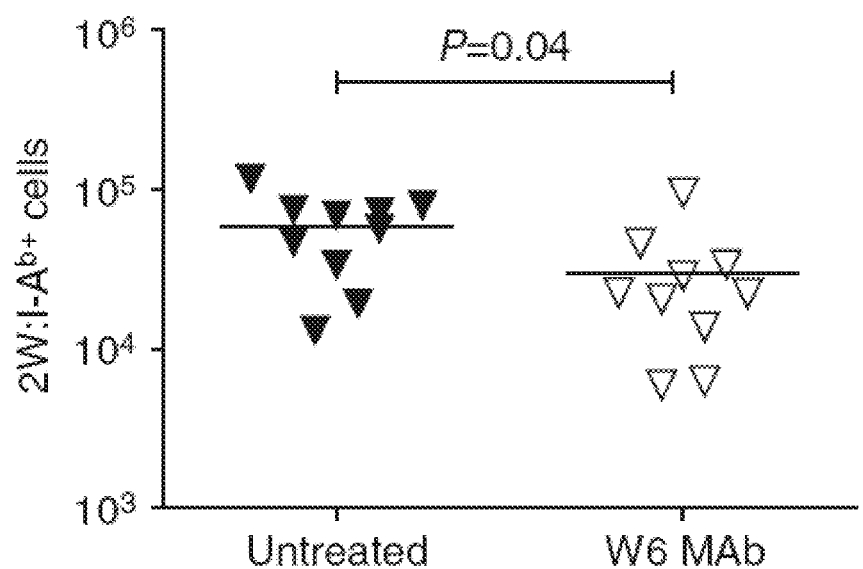
FIG. 11B. At day 35 post infection (21 days following MAb administration), the number of 2W-specific T cells was determined from the spleen as described in FIG. 11A.
Figure 11C:
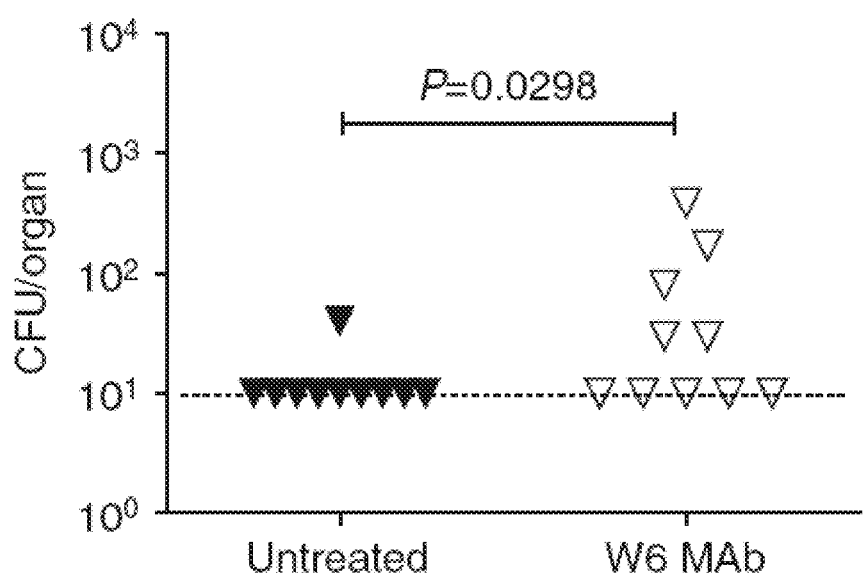
FIG. 11C. At day 35 post infection (21 days following MAb administration), the colony forming units for the spleen were determined. Statistical significance was calculated using a two-tailed Student's t-test. Data include 10 mice from two independent experiments.

The W6 MAb was next evaluated for its ability to block 2W specific in vivo expansion of antigen specific T cells in response to an acute or chronic bacterial infection. C57BL/6 mice were administered W6 MAb and infected with *Listeria monocytogenes* expressing 2W (Ertelt et al. J Immunol 182:3032-3038 (2009)). Seven days later, the number of activated 2W specific cells was decreased by 146 fold in response to W6 MAb compared to no antibody control (FIG. 11A). To test in vivo 2W specific CD4+ T cell responses and their contribution to bacterial clearance in a chronic infection, 129 mice were infected with $10^8$ *Salmonella typhimurium* expressing 2W peptide (Uzzau et al. *Proc Natl Acad Sci USA* 98:15264-15269 (2001); Nelson et al. *J Immunol* 190:2828-2834 (2013)). The mice received a single dose of W6 blocking antibody fourteen days post infection and were sacrificed at day 35 to evaluate antigen specific T cell proliferation and colony forming units (CFU). Infected mice treated with the W6 MAb have significantly lower 2W specific CD4+ T cells, higher bacterial burden, and do not clear the *salmonella* infection (FIG. 11B and FIG. 11C). These data highlight the importance of a single antigen-specific T cell population and the blocking ability of the W6 MAb to prevent in vivo pathogen clearance.

To compare the affinity of the FS1 and W6 MAb with previously published reagents, a direct side-by-side comparison with known $IA^{g7}$ or $IA^b$ specific antibodies was performed. The results are shown in Table 2, and illustrate that the FS1 MAb (anti-p63:$IA^{g7}$) has 100 fold higher affinity ($1.7 \times 10^{11}$) than the 10-2.16 MAb[28] (anti-$IA^{g7}$) ($2.9 \times 10^{-9}$ $K_D$ (M)). The W6 MAb (anti-2W:$IA^b$) had an affinity comparable to known $IA^b$ antibodies (Y3P[29], Y-Ae[3], and AF6-120.1[30]). These results suggest that the two MAb generated had comparable or higher affinity than conventional approaches used to develop MAb.

TABLE 2

Comparison of anti-p:MHCII antibody affinities

| Antibody clone | Antigen | $K_D$(M) |
| --- | --- | --- |
| FS1 | p63:$IA^{g7}$ | $1.7 \times 10^{-11}$ |
| 10-2.16 (ref. 28) | p63:$IA^{g7}$ | $2.9 \times 10^{-9}$ |
| W6 | 2W:$IA^b$ | $3.4 \times 10^{-9}$ |
| AF6-120.1 (ref. 30) | 2W:$IA^b$ | $7.1 \times 10^{-9}$ |
| Y3P (ref. 29) | 2W:$IA^b$ | $1.9 \times 10^{-9}$ |
| Y-Ae (ref. 3) | $E\alpha_{52-68}$:$IA^b$ | $4.8 \times 10^{-10}$ |

Discussion

Using this methodology hybridomas producing six novel anti-peptide:MHCII MAb were generated, and for two of these presented here, the high affinity and biological capacity to limit TCR engagement, prevent subsequent T cell activation, label antigen presenting cells, and in vivo use to prevent tolerance induction and bacterial pathogen clearance were demonstrate. This novel methodology is highly efficient in part due to pre-screening and enrichment, saving both time and resources (see, e.g., Table 1).

Recently, an antibody against insulin B peptide$_{9-23}$ in $IA^{g7}$ (anti-InsB$_{9-23}$:$IA^{g7}$) was generated and shown to inhibit diabetes in NOD mice (Zhang, L. et al. *Proc Natl Acad Sci USA* 111, 2656-2661 (2014)). In the current study, the FS1 MAb was generated as a diabetes relevant peptide in the context of $IA^{g7}$. Here, successful blockade of antigen specific tolerance using FS1 MAb and rapid diabetes were demonstrate (FIG. 10B). The W6 reagent was generated to understand T cell responses during both homeostasis and bacterial pathogenesis, as the 2W peptide can be engineered into a pathogen of interest.

Example 3

Except as otherwise indicated, the reagents used in Example 3 were obtained from the same source as the reagents in Example 2 and the methods of Example 3 are as further described in Example 2.

Three C57BL/6 mice were immunized with phycoerythrin (PE) (Prozyme, Hayward, Calif.) by subcutaneous injection of 100 μL of complete Freund's adjuvant (CFA) (Sigma-Aldrich, St. Louis, Mo.) emulsion containing 25 μg of PE in the hind flank. After 3 weeks, mice were boosted intravenously with 50 μg of PE. Three days later, the spleen and pooled lymph nodes (inguinal, brachial, cervical, and axillary) were harvested. Single-cell suspensions from spleen and pooled lymph nodes (inguinal, brachial, cervical and axillary) were prepared by forcing the tissue through a 100 μm cell strainer using the plunger end of a 1 mL syringe, washed with RPMI containing 2% FBS and resuspended in 100 μL with RPMI containing 2% FBS. The cells were next incubated with 1 μg PE to each sample (spleen and pooled lymph nodes per mouse for 30 min at 4° C., followed by 25 μL anti-PE microbeads (Miltenyi Biotec, Bergisch Gladbach, Germany) and incubated for 15 min at 4° C. The cells were then washed with 12 mL with PBS 2% FBS, resuspended in 3 mL PBS with 2% FBS and applied to a magnetized LS column (Miltenyi Biotec, Bergisch Gladbach, Germany). The column was washed three times with 3 mL PBS with 2% FBS, removed from the magnet and the cells were eluted in 5 mL PBS with 2% FBS. The magnetically labeled cells were pelleted and re-suspended in 100 μL PBS with 2% BSA followed by staining with BRILLIANT violet 421 (BV421)-anti-CD138 (a plasma cell marker), BV650-anti-B220 (a B cell marker), GHOST DYE Violet 510 (a viability marker), and BRILLIANT violet 510

Figure 12:
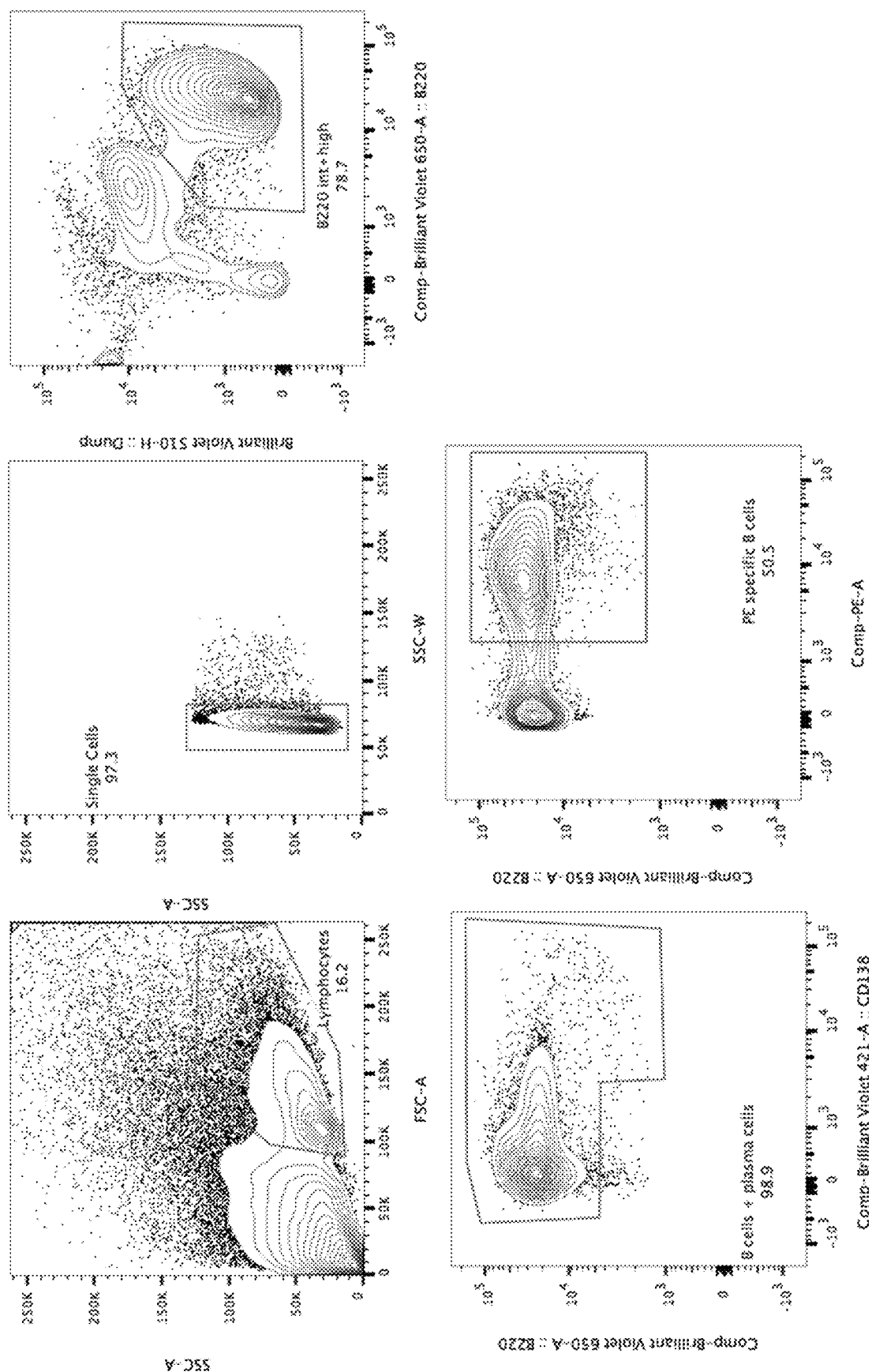
FIG. 12 shows a flow cytometry gating strategy used in Example 3.
Figure 13:
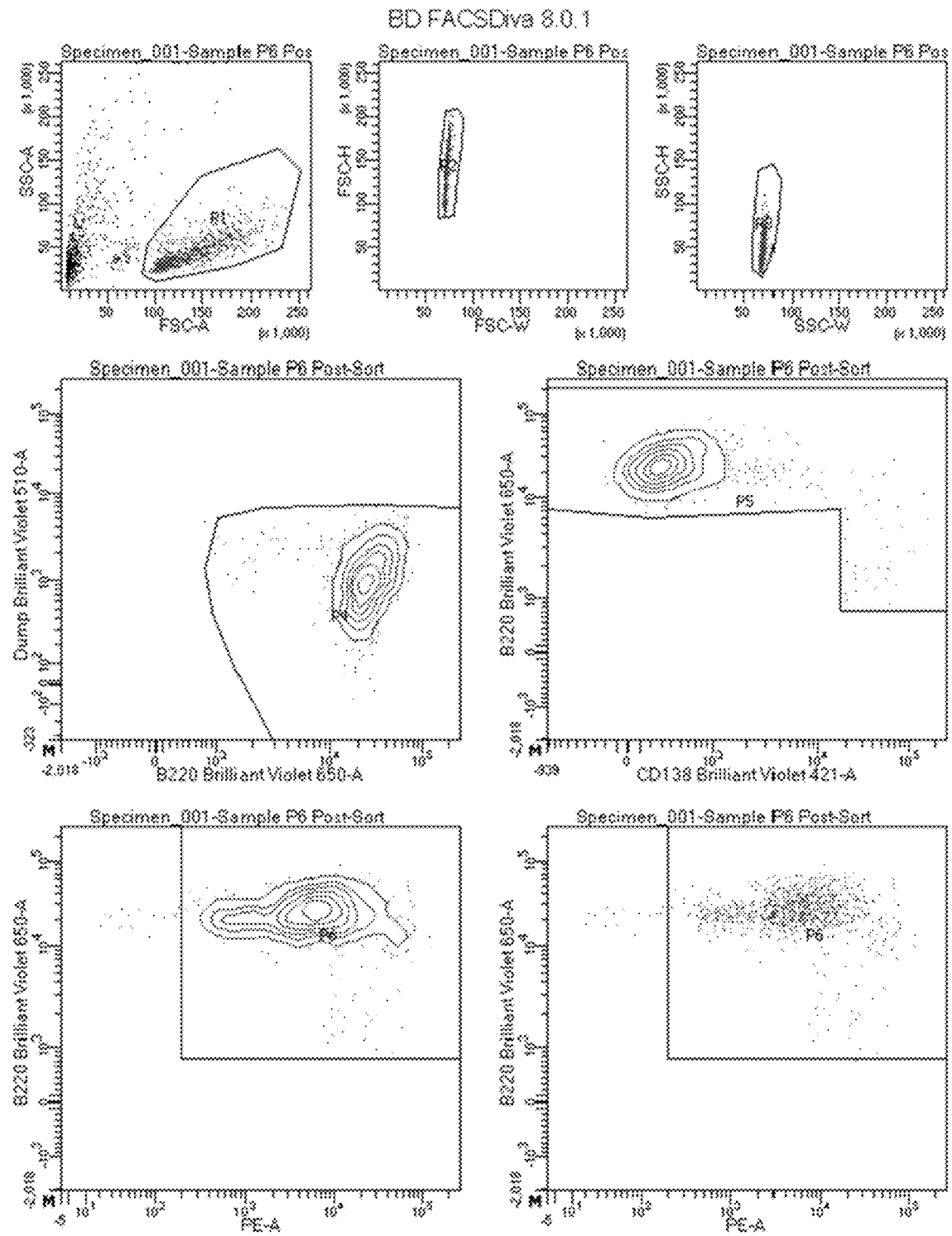
FIG. 13 shows a flow cytometry gating strategy used in Example 3.

(BV510)-anti-CD90.2, anti-CD11c, anti-F4/80, and anti-GR-1 (FIGS. 12-13). PE-specific cells were determined by negative staining using a dump gate to exclude T cells (CD90), macrophage (F4/80), dendritic cells (CD11c) and granulocytes (GR-1). B220 intermediate B cells or B220 high B cells or CD138 positive and PE positive cells were sorted on a BD FACSAria II. Approximately 400,000 PE-specific B cells were obtained with 98% purity (FIG. 12). All antibodies were used at a 1:100 dilution for staining, except CD90.2 which was diluted 1:500. The data were analyzed using FlowJo software (v.10) (FlowJo, LLC, Ashland, Oreg.).

The enriched B cells were fused with SP2/0 mouse myeloma cells using the HY Hybridoma Cloning Kit according the manufacturer's protocol using method A (Stem Cell Technologies, Vancouver, Canada) and plated out into semi-solid methylcellulose-based HAT media as described in Example 2. Fourteen days later, 5 visible colonies were harvested from the plates and grown in hypoxanthine-thymidine (HT) containing media until ELISA screening.

Supernatants from each hybridoma clone were screened for PE binding via indirect ELISA. Supernatant was incubated in a 96-well plate previously coated with 20 µg/mL PE and blocked with 1% BSA. PE binding antibodies were detected by incubating with HRP-conjugated goat anti-mouse IgG (BioLegend, San Diego, Calif.) diluted to 1:2000 at room temperature for 45 minutes followed by addition of ABTS substrate solution (KPL, SeraCare Life Sciences, Milford, Mass.) and detection by absorbance at 405 nm. Results are shown in FIG. 14. Sequences for Clones 1, 4, and 5 are shown in FIG. 23. The sequences for Clone 1 and Clone 2 are the same.

Example 4

Except as otherwise indicated, the reagents used in Example 4 were obtained from the same source as the reagents in Example 2 and the methods of Example 4 are as further described in Example 2.

Figure 15A:
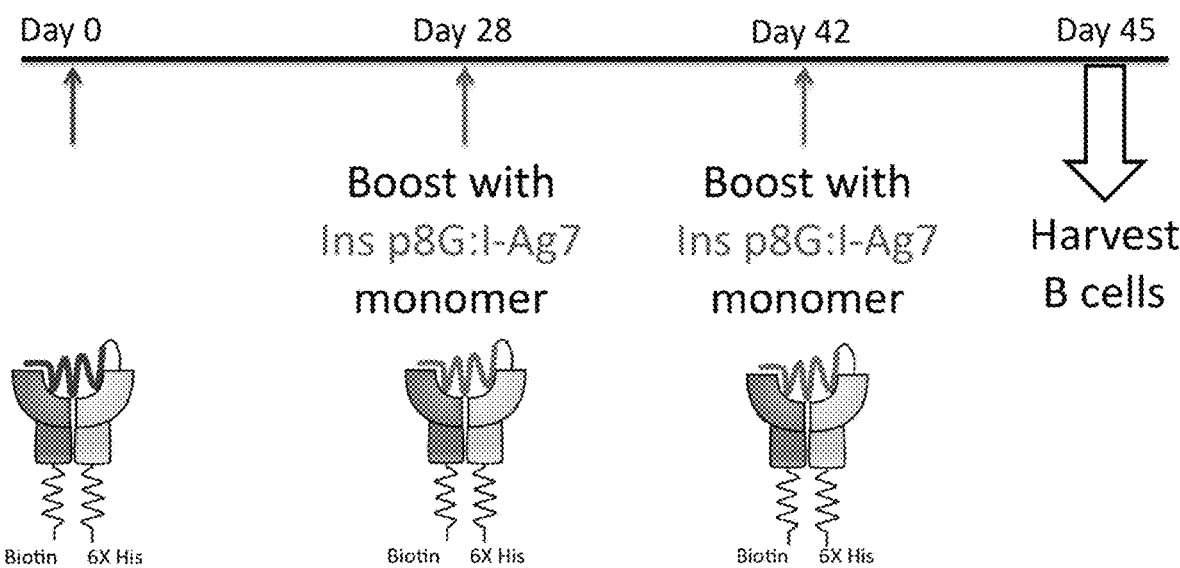
FIG. 15A shows an exemplary immunization scheme as used in Example 4.
Figures 15B, 16:
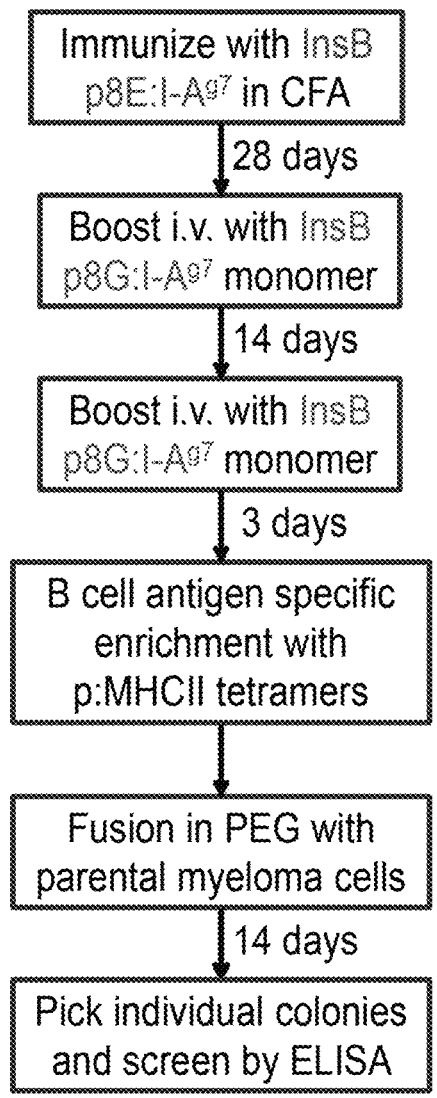
FIG. 15B shows an exemplary scheme for the generation and validation of p:MHCII MAb as used in Example 4.
FIG. 16 shows IA$^{g7}$ groove position for InsB:9-23(wt) (SEQ ID NO:17), InsB:9-23 p8E (SEQ ID NO:9), and InsB:9-23 p8G (SEQ ID NO:18).

Mice were immunized according to the immunization scheme shown in FIG. 15. Two modified $IA^{g7}$ MHCII monomers containing the insulin peptides (InsB p8E, InsB p8G) shown in FIG. 16 were used to make a cross-reactive monoclonal antibody. Two BALB/c mice were immunized subcutaneously in the flank and base of the tail with 50 µg total of Ins p8E:$IA^{g7}$ MHCII monomer emulsified in complete Freunds' adjuvant. Twenty eight days later each mouse was boosted by intravenous injection of 100 µL total volume containing 10 µg of Ins p8G:$IA^{g7}$ MHCII monomer in PBS. Fourteen days later (day 42) each mouse was boosted by intravenous injection of 100 µL total volume containing 10 µg of Ins p8G:$IA^{g7}$ in PBS. Three days after the second boost (day 45), mice were euthanized and a single cell suspension was made from cells from pooled spleens and draining lymph nodes. Cells were stained in 150 µL of complete media (DMEM, 10% Fetal Calf Serum (FCS), β-ME, pen/strep, nonessential amino acids) containing 13.3 nM PE-conjugated p:MHCII/mouse and incubated on ice for 25 minutes. Cells were washed with complete media and resuspended in 200 µL of complete media containing 50 µL of anti-PE microbeads (Miltenyi Biotec, Bergisch Gladbach, Germany) per mouse and incubated on ice for 25 minutes. Cells were washed with complete media and resuspended in 5 mL of complete media per spleen. The cell suspension was then applied to a pre-equilibrated LS magnetic column (Miltenyi Biotec, Bergisch Gladbach, Germany) and washed 2 times with 3 mL of complete media. The cells were eluted from the column in 5 mL Medium A (StemCell Technologies, Vancouver, Canada), centrifuged, and enumerated. The enriched B cells were fused with SP2/0 mouse myeloma cells using the HY Hybridoma Cloning Kit according the manufacturer's protocol using Method A (StemCell Technologies, Vancouver, Canada). A small portion of the enriched cells and flow through was stained as described in Example 2 to determine antigen specific B cell purity and phenotype prior to hybridoma fusion.

Hybridoma selection and specificity screening. Twelve days post-hypoxanthine-aminopterin-thymidine (HAT) selection, 624 individual colonies were handpicked and transferred to 96-well plates containing Medium E (Stem-Cell Technologies, Vancouver, Canada). Four days later hybridoma supernatants were transferred to 96-well plates and fresh medium E was added to the cells. To test the specificity of hybridoma supernatants for MHCII and p:MHCII, a decoy screening approach was employed. ELISA plates were coated with 50 nanograms (ng)/well either $HEL_{11-25}$:$IA^{g7}$ or Ins p8E:$IA^{g7}$, or Ins p8G:$IA^{g7}$, and then blocked with 1% BSA in PBS for 1 hour. Hybridoma supernatants were mixed 1:1 with ELISA wash buffer (PBS+ 0.05% Tween20) and added to the p:MHCII coated plates and incubated at 37° C. for 2 hours. Media alone was used as a negative control while anti-$IA^{g7}$ (clone 10-2.16, Bio X Cell, West Lebanon, N.H.) was used as a positive control. For antibody detection the wells were incubated with HRP conjugated goat anti-mouse IgG (BioLegend, San Diego, Calif.) diluted to 1:2000 at room temperature for 2 hours followed by addition of ABTS substrate solution (KPL, SeraCare Life Sciences, Milford, Mass.) and detection by absorbance at 405 nm. 38 clones were determined to be positive for P8E specificity (~6.1% efficiency), and of these 9 were cross reactive to P8E and P8G. Antibodies reacting to P8E and HEL p:MHCII monomers were considered specific for MHCII independent of peptide, while antibodies reacting with Ins p8E:$IA^{g7}$ and Ins p8G:$IA^{g7}$ were considered insulin B 9-23 cross reactive.

Figure 17A:
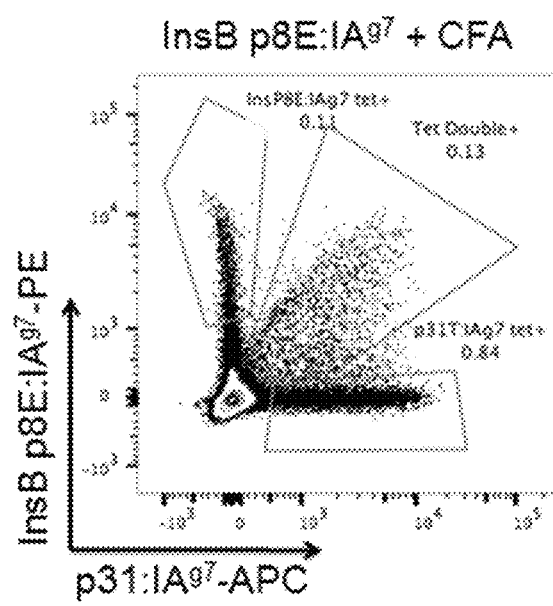
FIG. 17A. InsB p8E:IA$^{g7}$ tetramer positive cells were gated on lymphocytes, singlets, dump-, Ig(H+L) or B220+, SA-PE*AF647 and SA-APC*dy1755- and decoy p31:IA$^{g7}$-APC-.
Figure 17B:
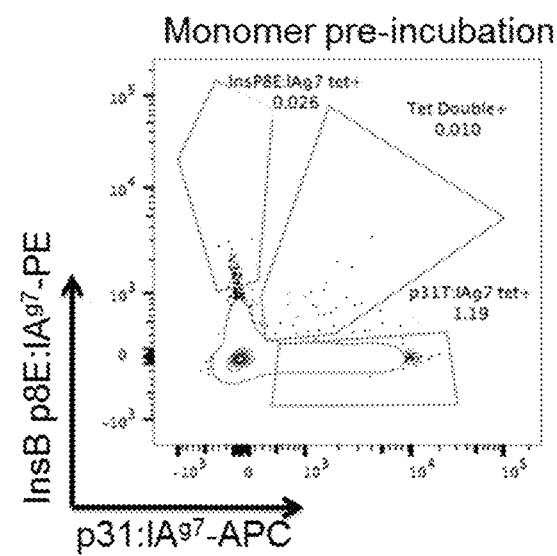
FIG. 17B. After pre-incubation with 16.5 μM 96% of InsB p8E:IA$^{g7}$ tetramer binders were competed off while only 40% of p31:IAg7 binders were competed off.
Figure 19A:
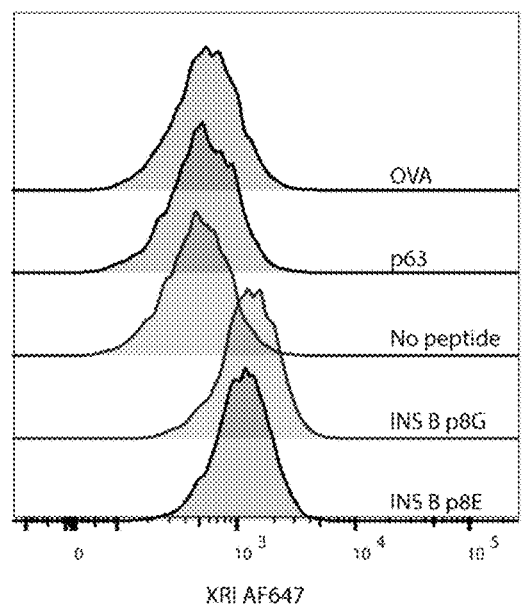
FIG. 19A. B6.G7 BMDCs were pulsed with InsB p8E, InsB p8G or irrelevant peptides and AF647-XRI1 staining was measured FIG. 19B. The geometric mean (gMFI) of the AF647-XRI1 staining of FIG. 19A was determined.
Figure 19B:
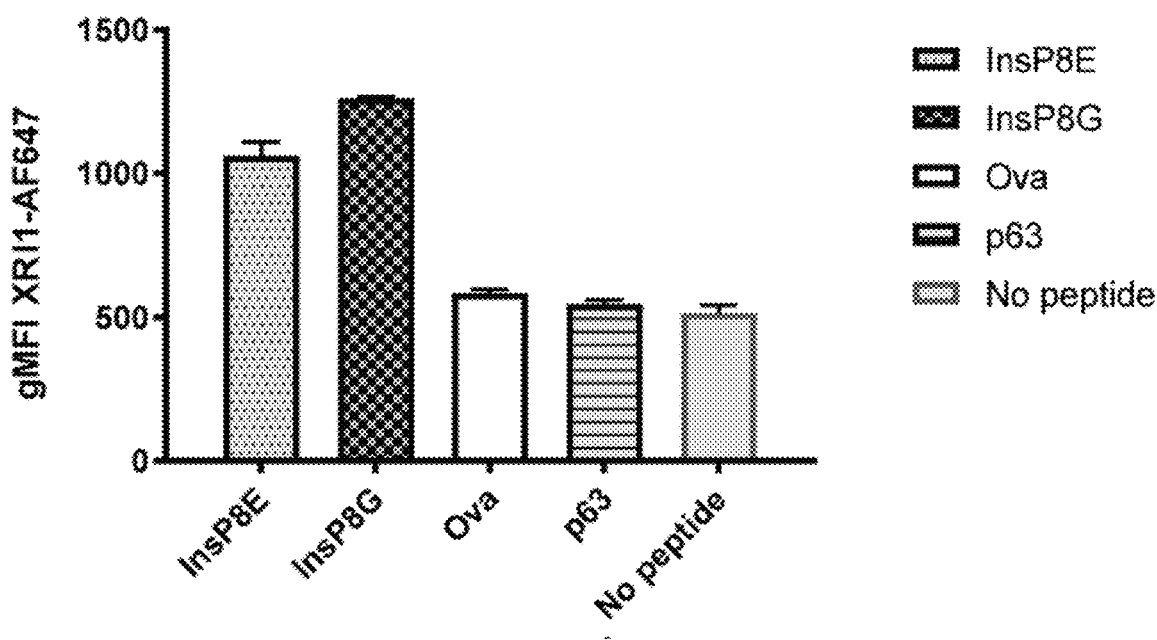
FIG. 19(A-D) shows in vitro staining of peptide pulsed bone marrow derived dendritic cells (BMDCs) with XRI1 directly conjugated to AF647. Bone marrow was harvested and cultured for 9 days in 20 ng/mL GM-CSF. BMDCs were pulsed overnight with 40 μM peptide or no peptide+1 μg/mL LPS and then stained with AF-647-XRI1.
FIG. 19C. BMDCs from NOD, B6, B6.G7 and various NOD IA$^{g7}$ knockouts were pulsed with InsB p8E and AF647-XRI1 staining was measured.
FIG. 19D. The gMFI of the AF647-XRI1 staining of FIG. 19C was determined.
Figure 19C:
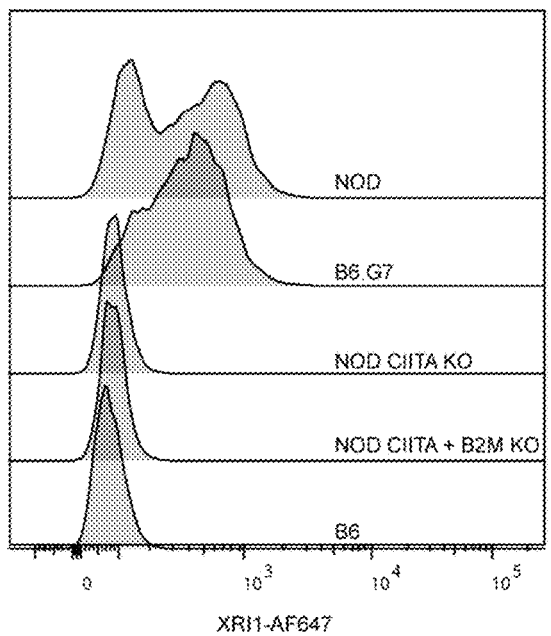
Figure 19D:
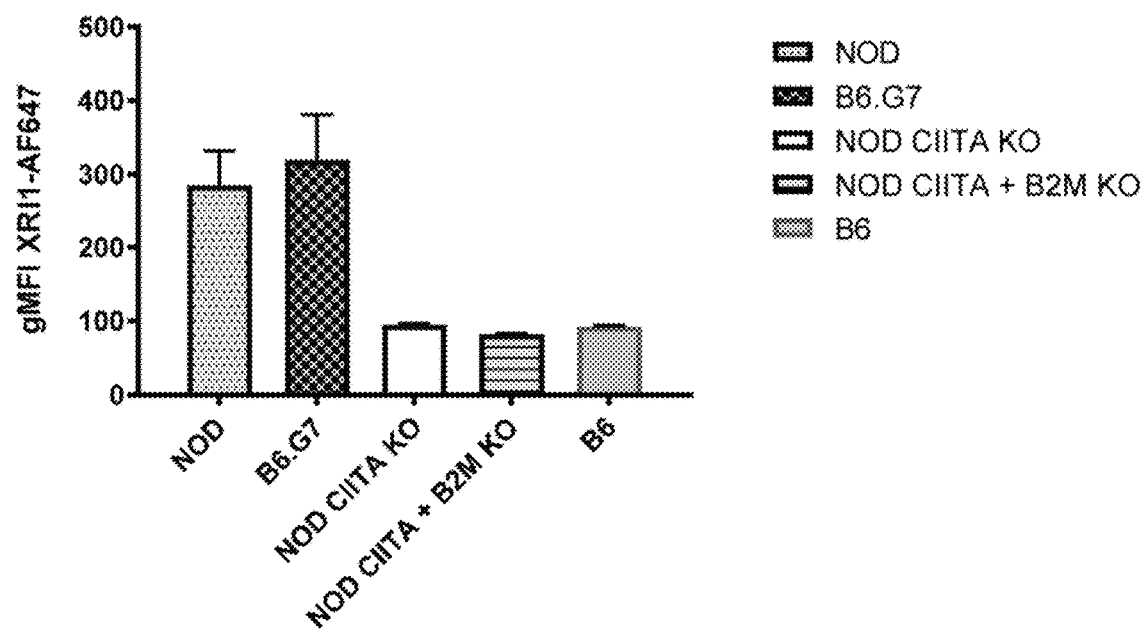
Figure 20A:
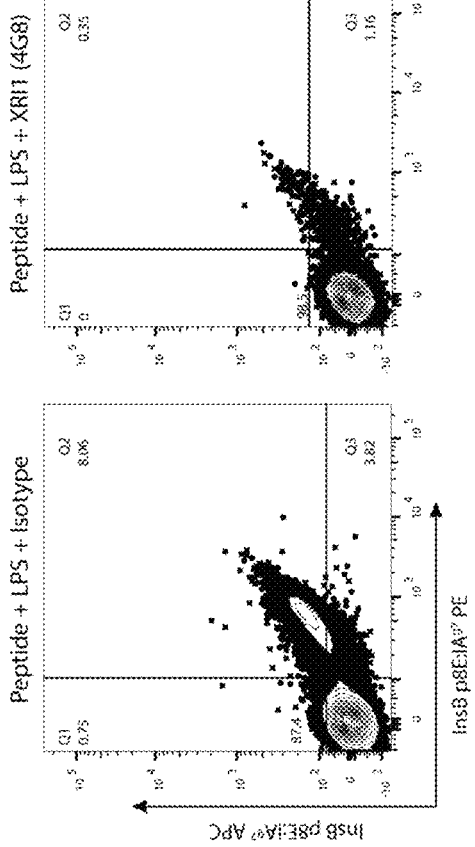
FIG. 20(A-D) shows in vivo validation of XRI1. NOD mice were injected i.p. (intraperitoneally) with 20 μg of either InsB p8E or InsB p8G+50 μg LPS and 500 μg of XRI1 (4G8) or isotype control antibody on day 0 and 500 μg of XRI1 (4G8) or isotype control antibody for a second dose on day +2. Five days later (day 7 after priming), secondary lymphoid organs were collected and dual tetramer staining was performed followed by MACS anti-APC and anti-PE enrichment. Tetramer positive T cells were gated on lymphocytes, single cells, dump-, CD3$^+$, CD4$^+$, dual tetramer$^+$. Representative flow cytometry analysis of CD4 T cell expansion after InsB p8E (FIG. 20A) or InsB p8G (FIG.
FIG. 20C shows quantification of tetramer positive cells of naïve mice compared to mice immunized with peptide+LPS+Isotype control or peptide+LPS+XRI1 treatment for InsB p8E. InsB p8G, or p63 tetramers.
FIG. 20D. Frequency of CD44 high PD-1+ cells within the tetramer+ CD4 gate. N=2-3.
Figure 20B:
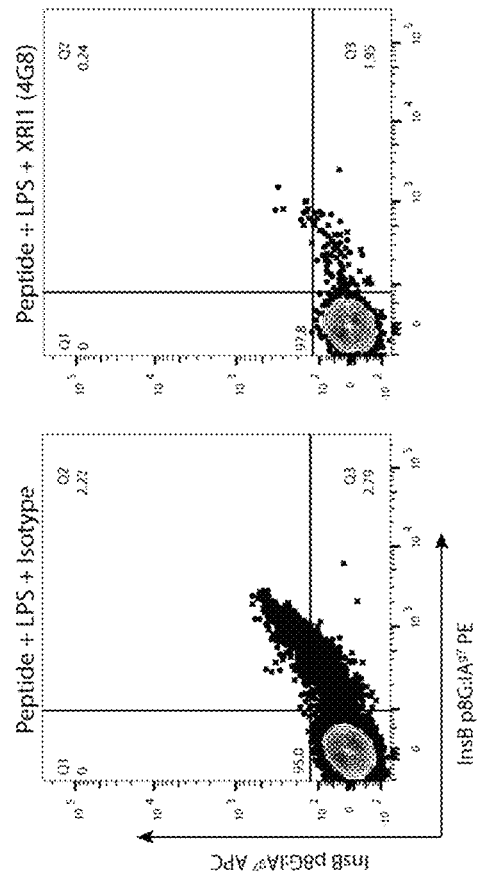
Figure 20C:
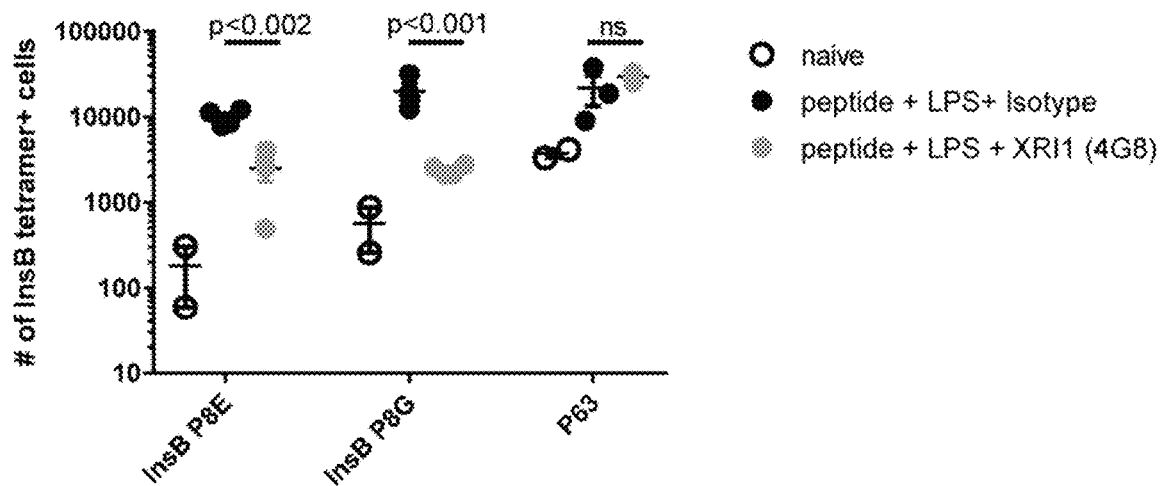
Figure 20D:
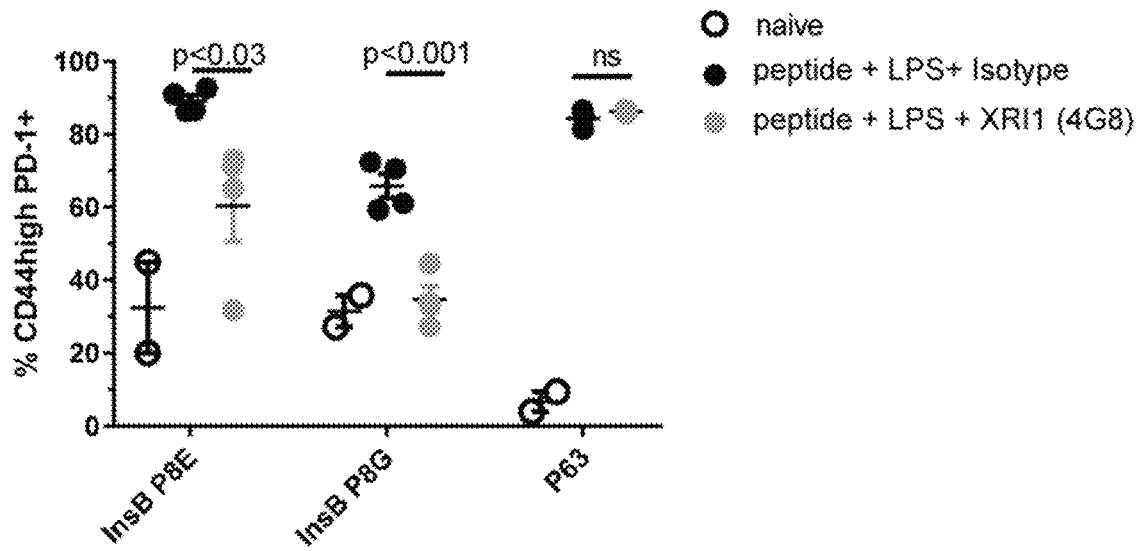

In vitro validation. One clone, Ins 4G8, was selected for further analysis (monoclonal antibodies produced by Ins 4G8 are referred to herein as cross reactive insulin 1 (XRI1)); sequence information for the antibody is provided in FIGS. 21-22). In vitro staining of Ins 4G8 hybridoma with $IA^{g7}$ tetramers. Tetramer validation is shown in FIG. 17. As shown in FIG. 18, Ins 4G8 hybridomas bind both InsB p8E:$IA^{g7}$ and InsB p8G:$IA^{g7}$ tetramers but not HEL:$IA^{g7}$ or hCLIP:$IA^{g7}$.

In vitro staining of peptide pulsed bone marrow derived dendritic cells (BMDCs) with XRI1 directly conjugated to AF647. Bone marrow was harvested from NOD mice and cultured for 9 days in 20 ng/mL GM-CSF. BMDCs were pulsed overnight with 40 µM peptide or no peptide+1 µg/mL LPS and then stained with AF-647-XRI1. As shown in FIG. 19, B6.G7 BMDCs were pulsed with InsB p8E, InsB p8G, OVA323-339 or p63 and geometric mean (gMFI) of AF647-XRI1 staining was determined; BMDCs from NOD, B6, B6.G7 and NOD $IA^{g7}$ CIITA KO or NOD $CIITA^{-/-}\beta 2M^{-/-}$ mice were pulsed with InsB p8E and gMFI was determined.

In vivo validation. FIG. 20 shows in vivo validation of XRI1.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method comprising:
    providing a peptide-MHC complex (p:MHC)
    immunizing a subject with a composition comprising antigen, wherein the antigen comprises the peptide-MHC complex (p:MHC);
    isolating a population of cells from the subject;
    enriching a subpopulation of antibody-producing cells from the population of cells, wherein enriching a subpopulation of antibody-producing cells comprises selecting for cells that bind to the p:MHC, and wherein enriching a subpopulation of cells further comprises at least one of
        identifying expression of a lymphocyte marker,
        identifying mononuclear cells,
        identifying expression of a B cell marker,
        testing for viability, and
        testing for antigen specificity; and
    forming a hybridoma from a cell selected from the subpopulation of antibody-producing cells; and
    wherein the method further comprises excluding cells that bind to a decoy peptide-MHC complex prior to forming the hybridoma, wherein the decoy peptide-MHC complex comprises the same MHC as the p:MHC used to immunize the subject, and further wherein the decoy peptide-MHC complex comprises a different peptide than the p:MHC used to immunize the subject.

2. The method of claim 1, the method of further comprising screening the hybridoma for production of an antibody specific for the p:MHC.

3. The method of claim 1, wherein the antigen comprises a monomeric peptide-MHC complex.

4. The method of claim 1 wherein the antigen comprises a peptide-MHC Class I complex (p:MHCI) or a peptide-MHC Class II complex (p:MHCII).

5. The method of claim 1 wherein the antigen comprises at least two different peptide-MHC complexes, wherein the MHC of each peptide-MHC complex comprises the same MHC and wherein the peptide of each peptide-MHC complex is different.

6. The method of claim 1 further comprising after the step of immunizing a subject with a composition comprising antigen, wherein the antigen comprises the peptide-MHC complex, subsequently immunizing the subject with a second composition comprising a second antigen that comprises the same MHC but a different peptide than in the first peptide-MHC complex.

7. The method of claim 1 wherein enriching the subpopulation of antibody-producing cells comprises enriching a subpopulation of cells capable of binding to a multimeric form of antigen.

8. The method of claim 7 wherein the multimeric form of the antigen comprises a biotin, a desthiobiotin, or a fluorescent biotin derivative, or a combination thereof.

9. The method of claim 7 wherein the multimeric form of the antigen comprises a marker or a photosynthetic pigment or both, and wherein excluding cells that do not bind to p:MHC comprises excluding cells that bind to a decoy peptide-MHC complex prior to forming the hybridoma, and further comprises excluding cells that bind to the marker or the photosynthetic pigment.

10. The method of claim 7 wherein enriching cells capable of binding to a multimeric form of the antigen comprises using a magnetic bead, wherein the magnetic bead binds to a marker or a photosynthetic pigment or both.

11. The method of claim 1 wherein the enriching the subpopulation of the cells or excluding cells that bind to a decoy peptide-MHC complex comprises using flow cytometric identification and/or sorting.

12. The method of claim 1, wherein the step of excluding cells that bind to a decoy peptide-MHC complex prior to forming the hybridoma further comprises excluding cells that bind to a peptide not bound to an MHC complex and/or to an MHC complex not bound to a peptide, wherein the peptide and MHC are the same as that used in the p:MHC complex in the immunizing step.

13. The method of claim 1 wherein the subject is a mammal.

14. The method of claim 1 wherein the subject is a mouse, a humanized mouse, a rat or a rabbit.

15. The method of claim 1 wherein the composition comprising an antigen further comprises an adjuvant.

16. The method of claim 15, wherein excluding cells that do not bind to p:MHC comprises excluding cells that bind to a decoy peptide-MHC complex prior to forming the hybridoma, and further comprises excluding cells that bind to the adjuvant.

17. The method of claim 1, wherein the peptide of the peptide-MHC complex is covalently linked to the MHC complex.

18. The method of claim 15, wherein the adjuvant comprises Monophosphoryl Lipid A (MPLA).

19. The method of claim 1, wherein the composition comprising an antigen is introduced using dose escalation.

20. The method of claim 1, wherein selecting for cells that bind to the p:MHC comprises selecting cells that bind to a tetramer comprising the p:MHC.

* * * * *